United States Patent
Anderson et al.

(10) Patent No.: US 6,932,895 B2
(45) Date of Patent: Aug. 23, 2005

(54) AUTOMATED ELECTROPHORESIS GEL MANIPULATION APPARATUS

(75) Inventors: N. Leigh Anderson, Washington, DC (US); Jack Goodman, Lusby, MD (US); L. Eric Wallgren, Bethesda, MD (US)

(73) Assignee: Large Scale Proteomics Corporation, Vacaville, CA (US)

( * ) Notice: Subject to any disclaimer, the term of this patent is extended or adjusted under 35 U.S.C. 154(b) by 444 days.

(21) Appl. No.: 10/115,431

(22) Filed: Apr. 4, 2002

(65) Prior Publication Data

US 2002/0151076 A1 Oct. 17, 2002

Related U.S. Application Data

(63) Continuation-in-part of application No. 09/978,574, filed on Oct. 18, 2001, now abandoned, which is a continuation-in-part of application No. 09/859,664, filed on May 18, 2001, now Pat. No. 6,652,724, which is a continuation-in-part of application No. 09/783,132, filed on Feb. 15, 2001, which is a continuation-in-part of application No. 09/504,494, filed on Feb. 15, 2000, now abandoned, and a continuation-in-part of application No. 09/504,493, filed on Feb. 15, 2000, now Pat. No. 6,298,874.

(60) Provisional application No. 60/281,000, filed on Apr. 4, 2001.

(51) Int. Cl.[7] ............................................. G01N 27/463
(52) U.S. Cl. ...................... 204/613; 204/606; 204/612; 204/616

(58) Field of Search .................................. 204/606, 607, 204/608, 613, 456, 457, 462, 463, 466, 467

(56) References Cited

U.S. PATENT DOCUMENTS

| | | | |
|---|---|---|---|
| 4,810,348 A | 3/1989 | Sarrine et al. |
| 5,443,791 A | 8/1995 | Cathcart et al. |
| 5,858,189 A | 1/1999 | Williams |
| 5,865,975 A | 2/1999 | Bishop |
| 5,993,627 A | 11/1999 | Anderson et al. |

OTHER PUBLICATIONS

Zapolski et al, Electrophoresis, 1987, 8, pp. 255–261.*

* cited by examiner

*Primary Examiner*—Kaj K. Olsen
(74) *Attorney, Agent, or Firm*—John E. Tarcza; John C. Robbins; Thomas Gallegos

(57) ABSTRACT

An automated, computer controlled assembly is provided for continuously processing a large number of electrophoresis gels. The assembly includes a loading assembly for loading a gel onto a carrier, a gel staining assembly and a scanning and cutting assembly. The staining assembly and the scanning and cutting assembly each include a robotic arm that is able to capture a gel and transfer the gel to selected work stations and can transfer the gel between the respective robotic arms.

35 Claims, 42 Drawing Sheets

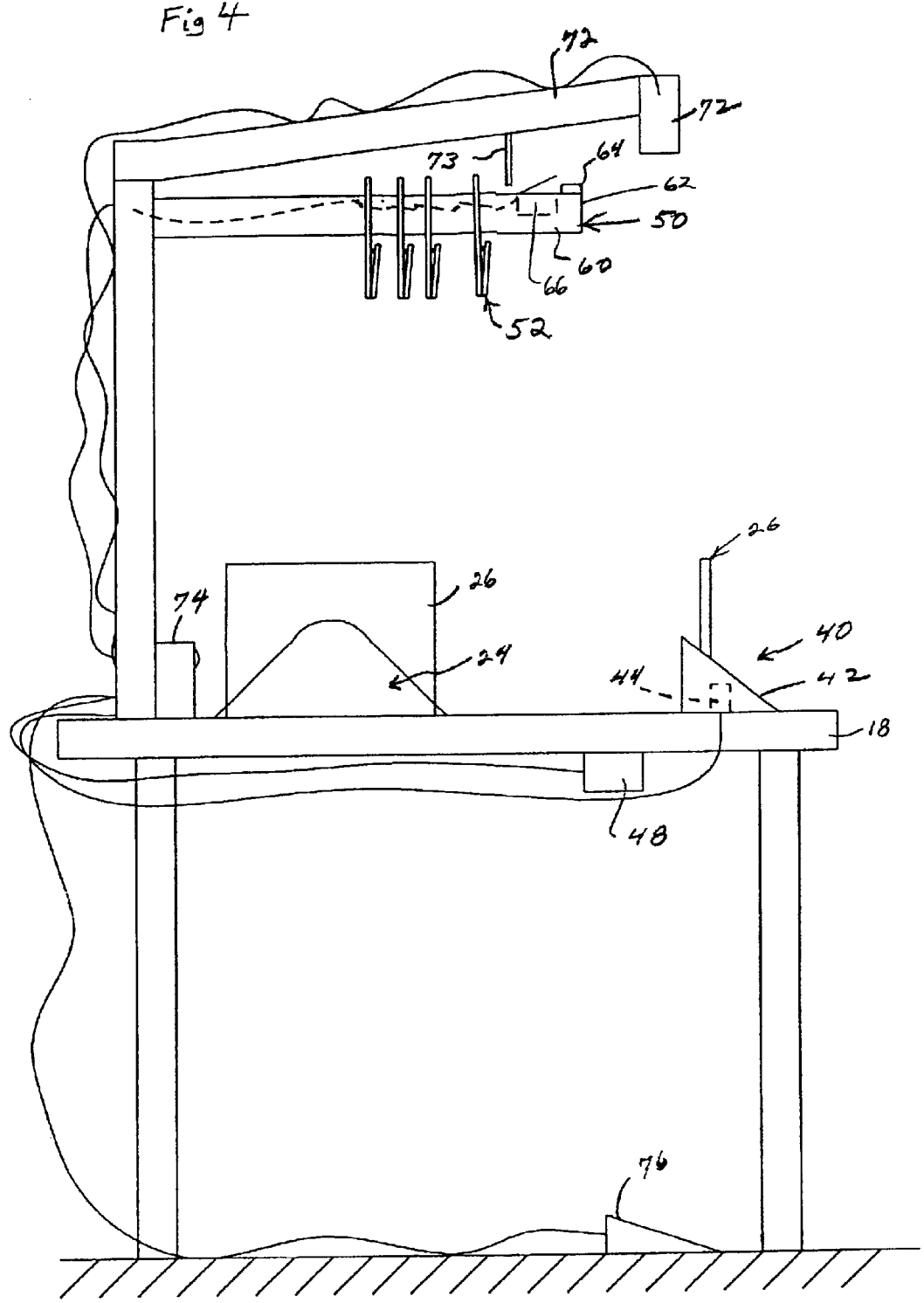

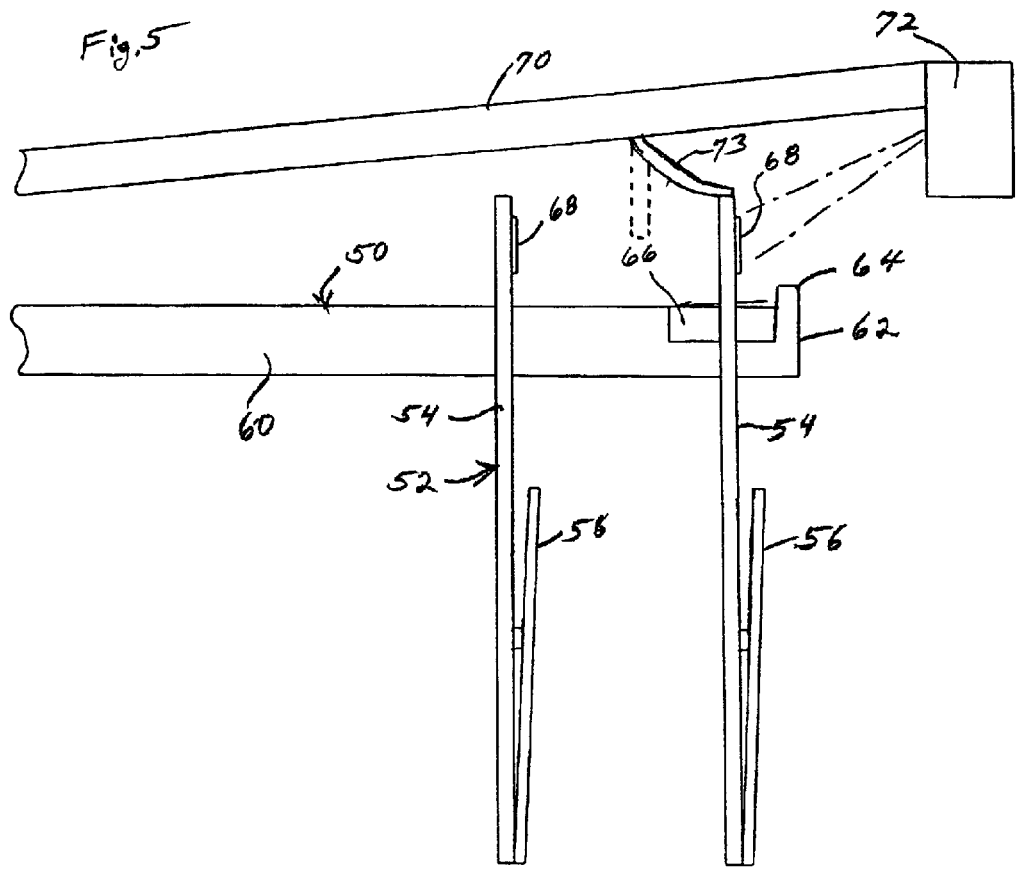
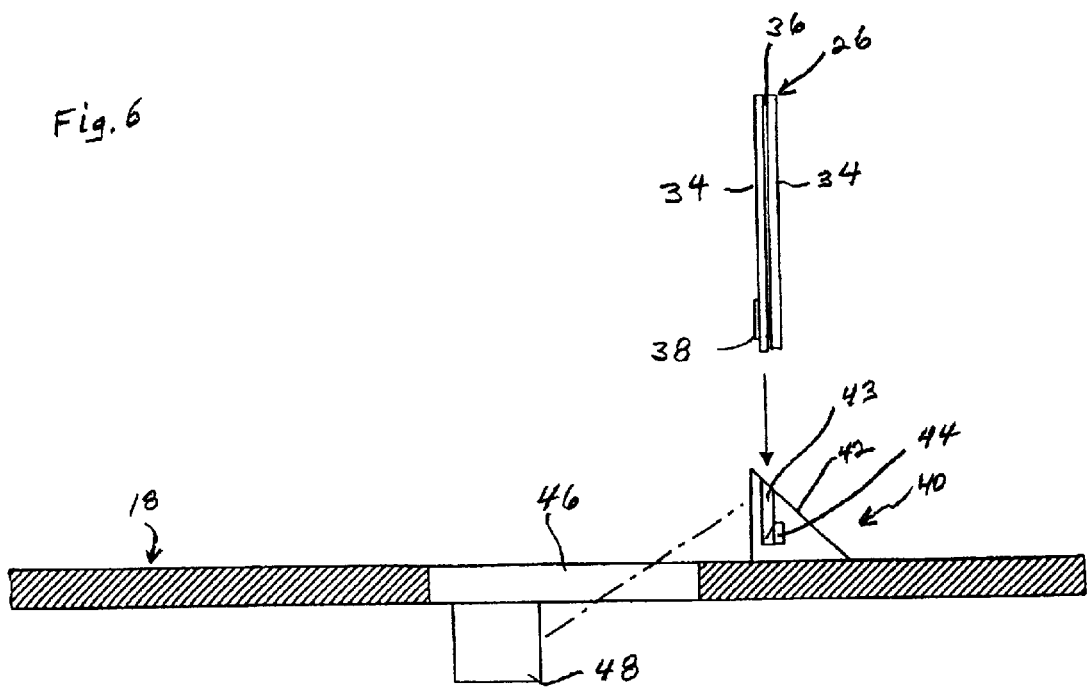

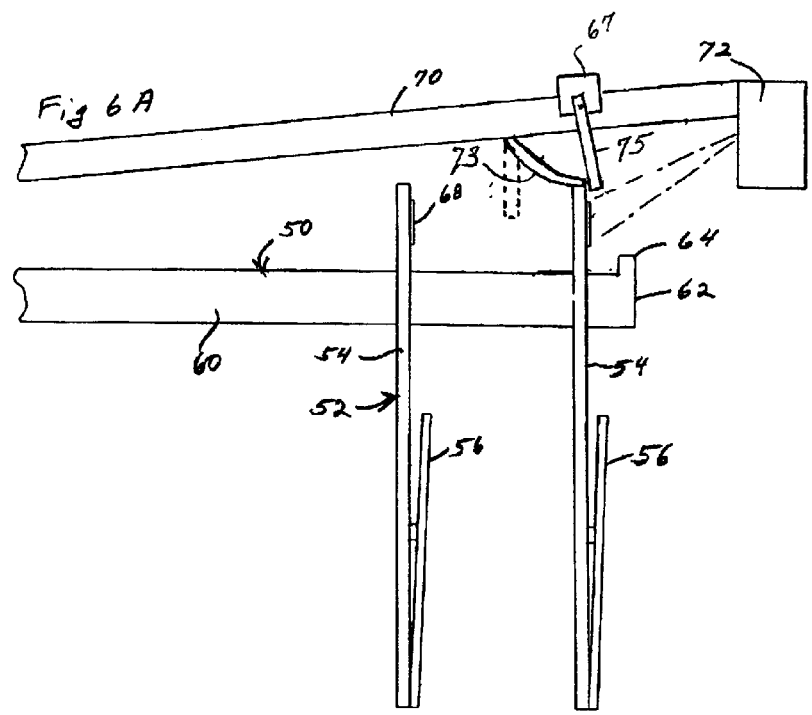
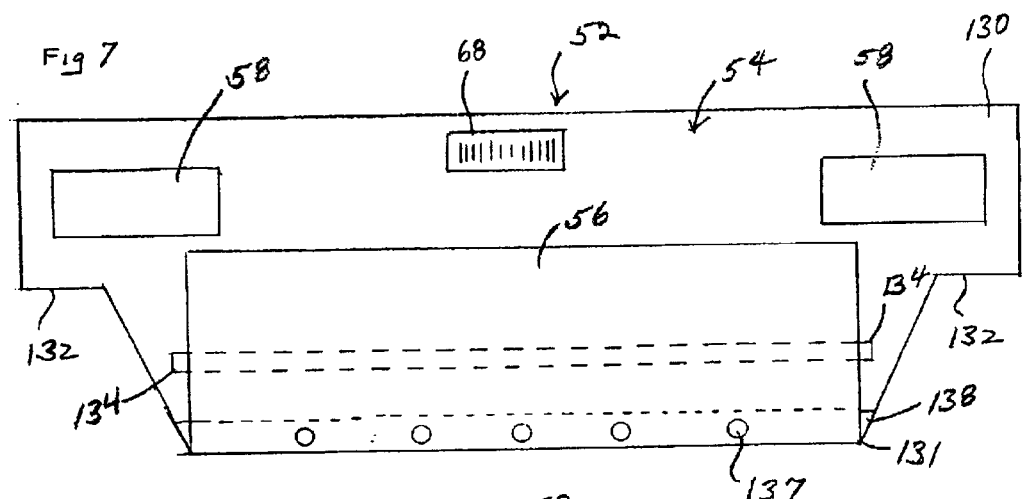
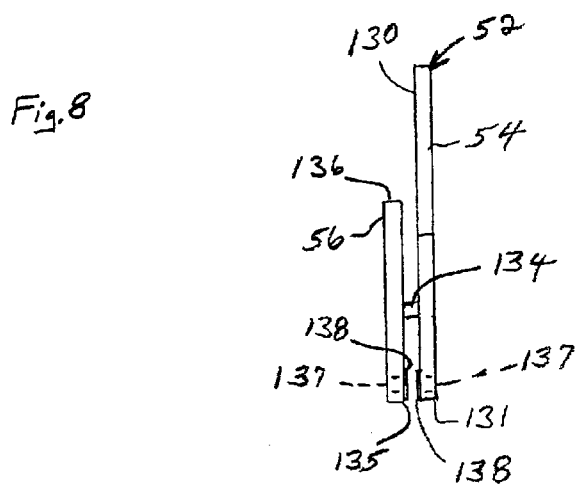

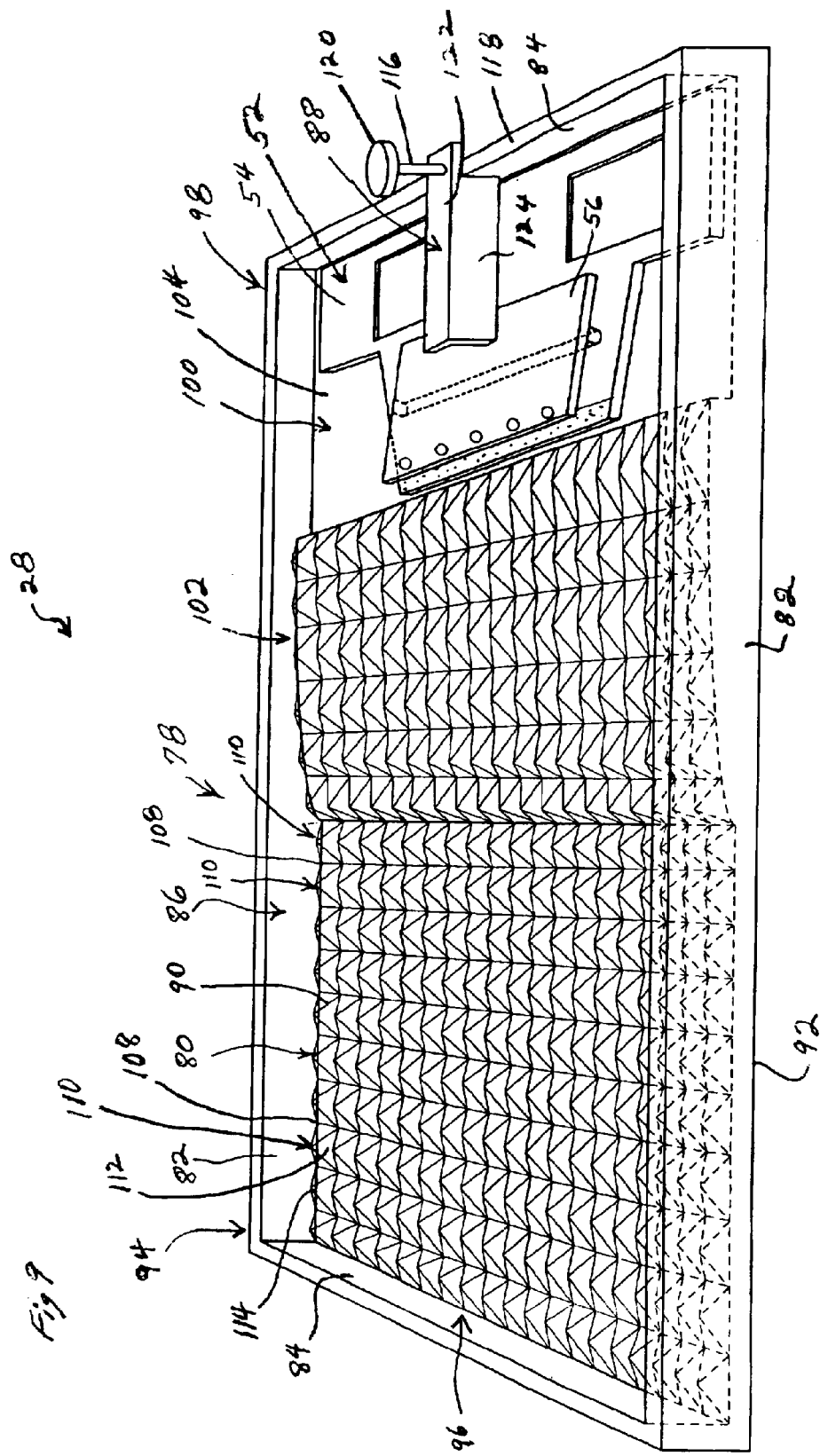

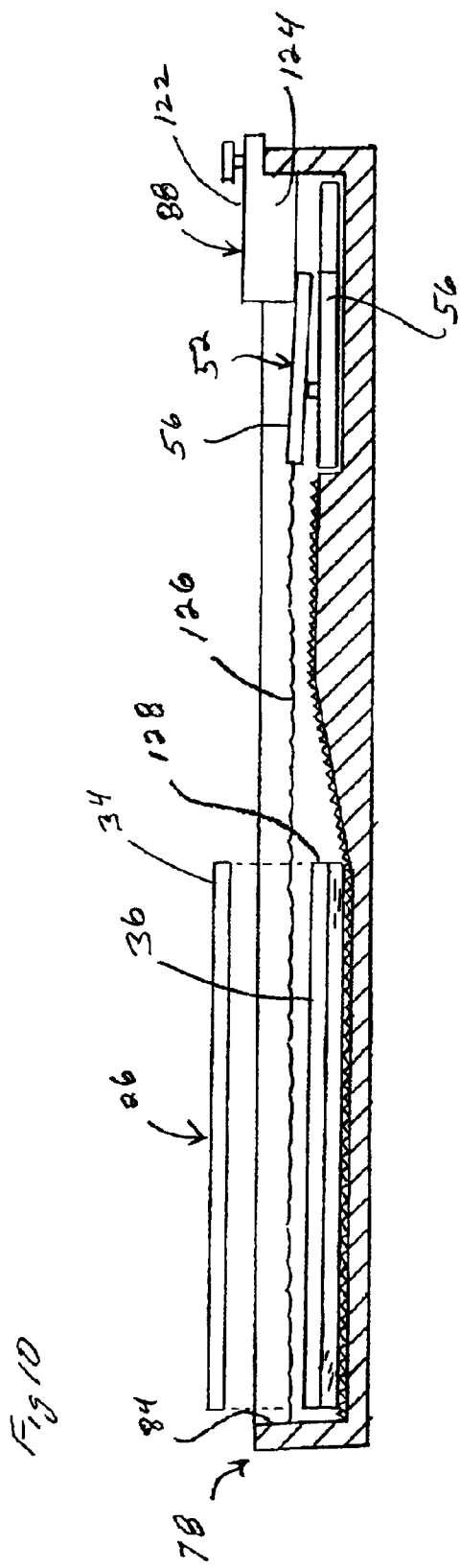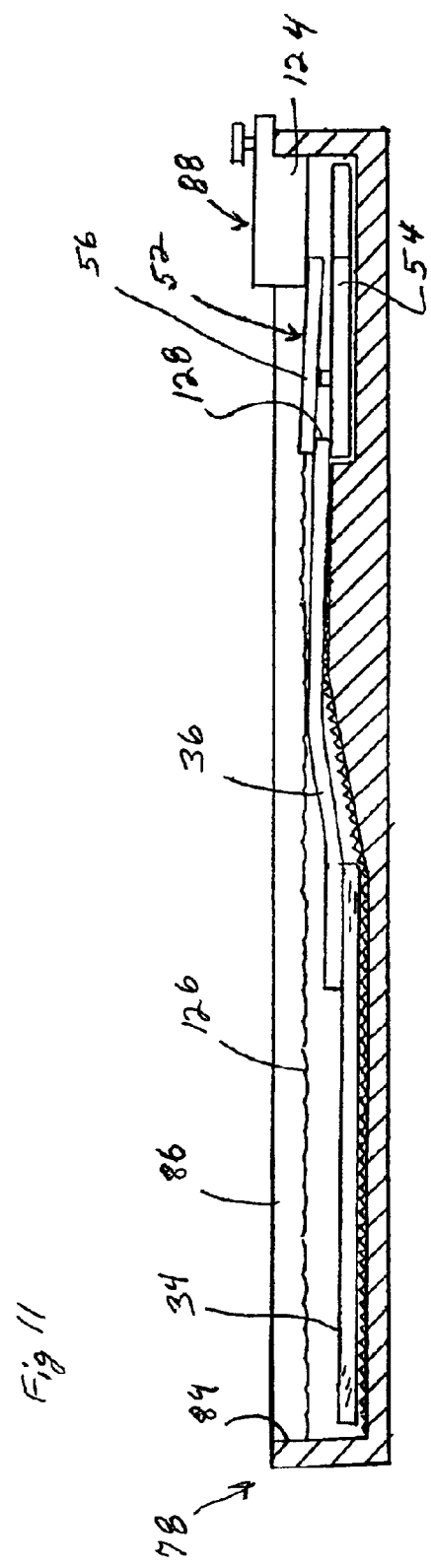

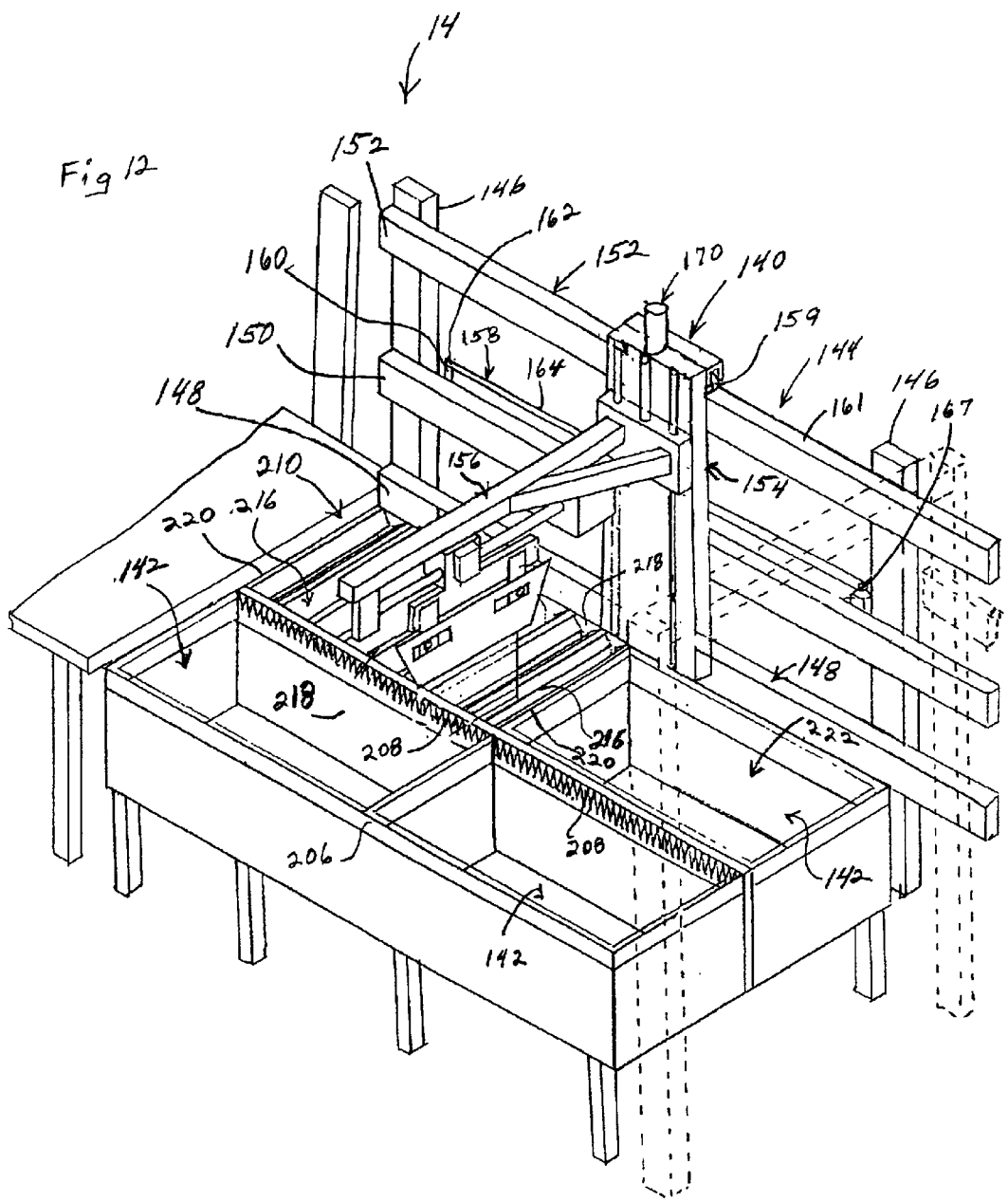

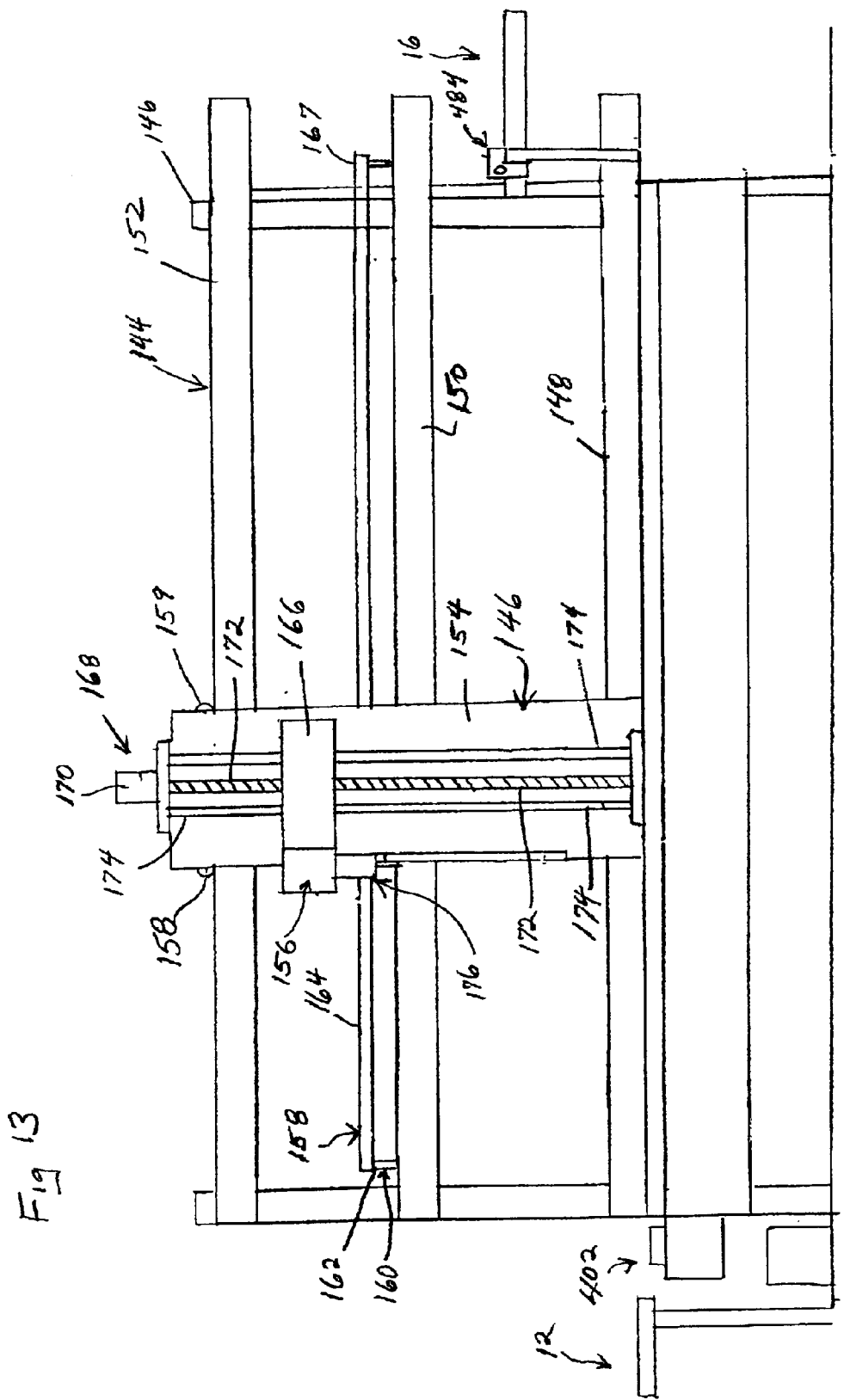

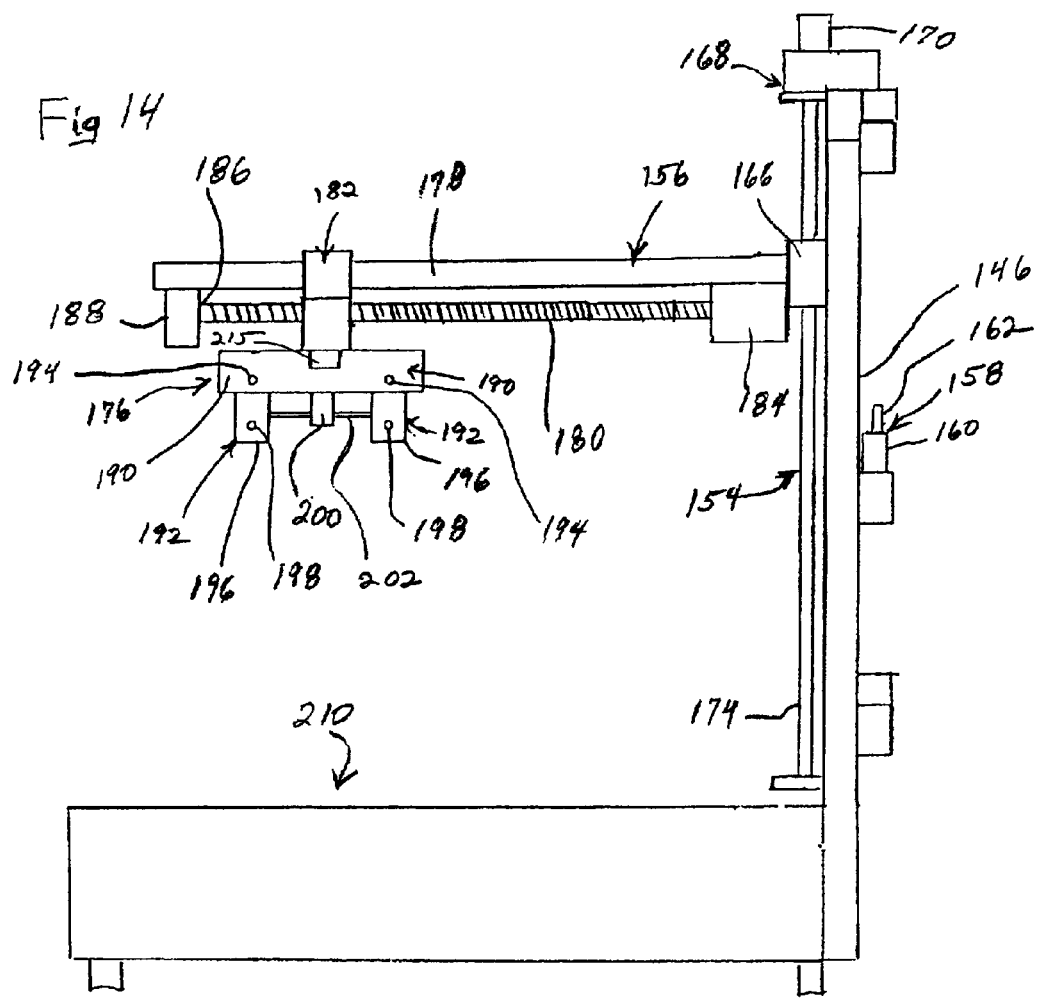

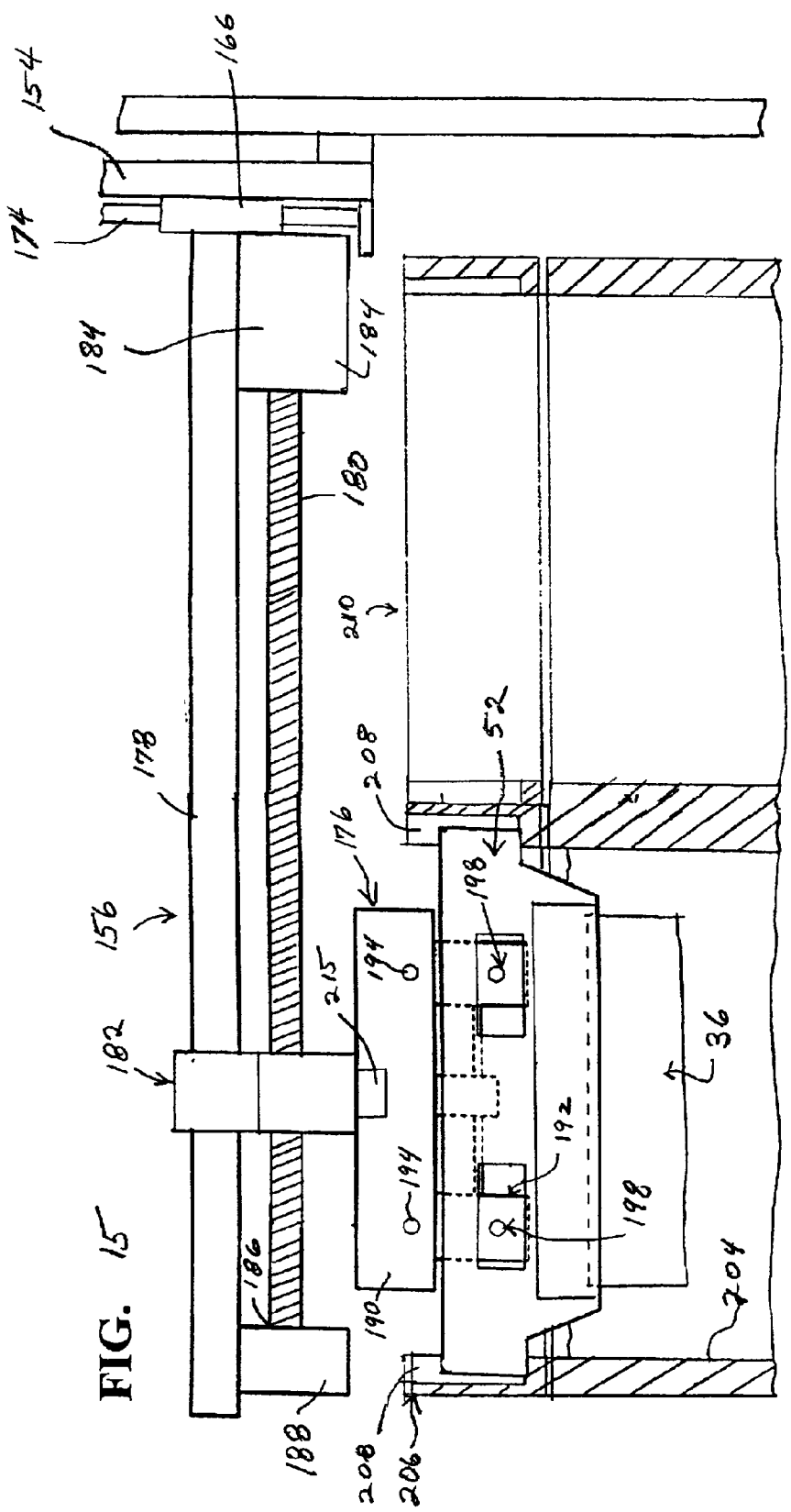

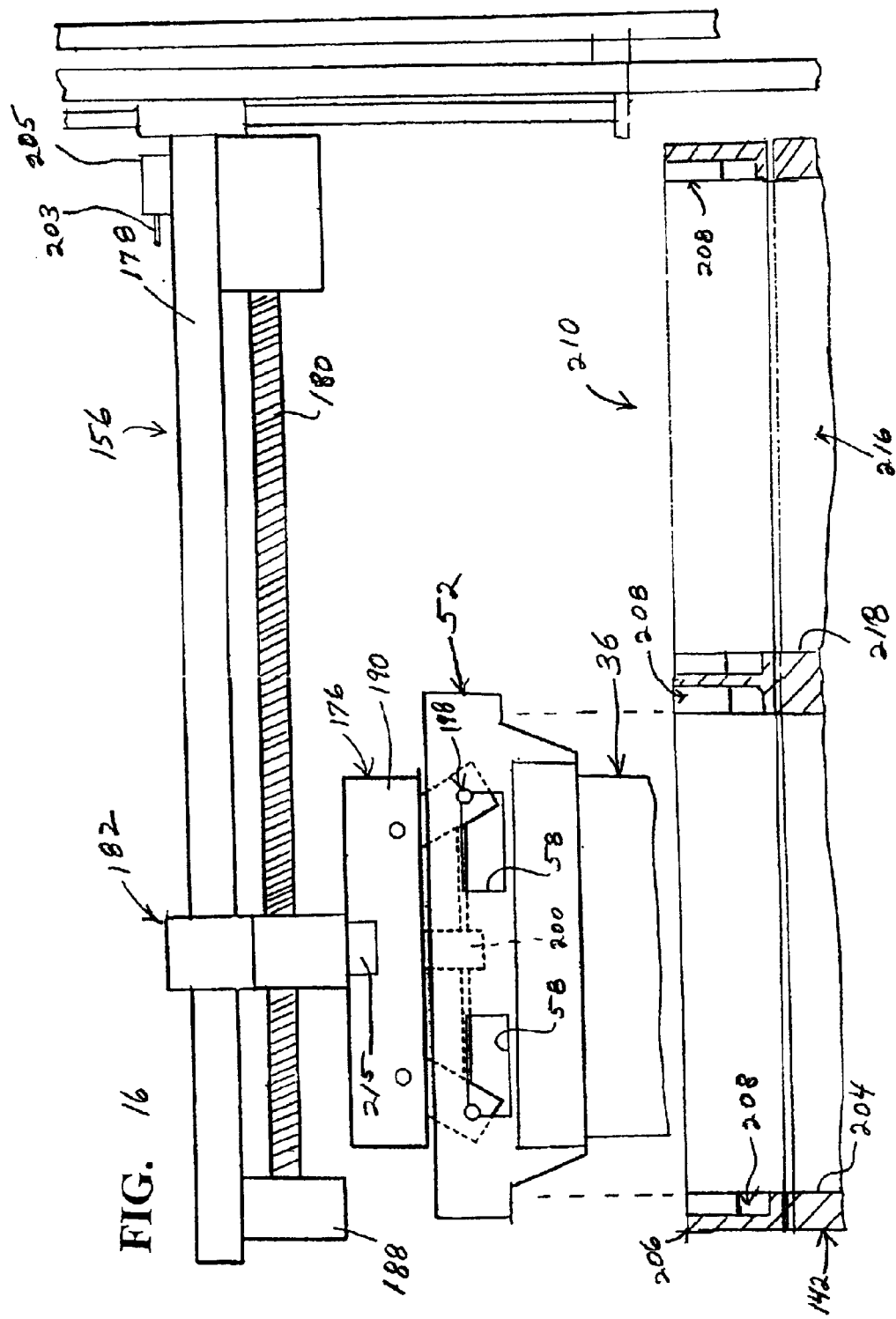

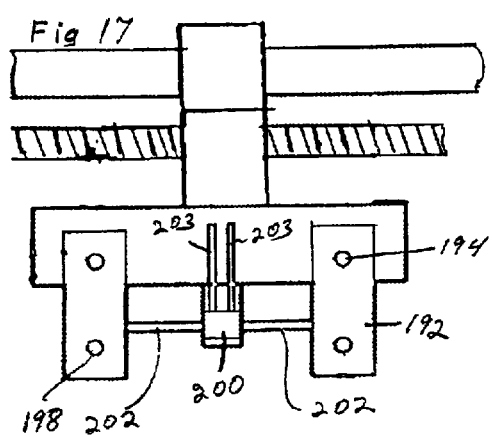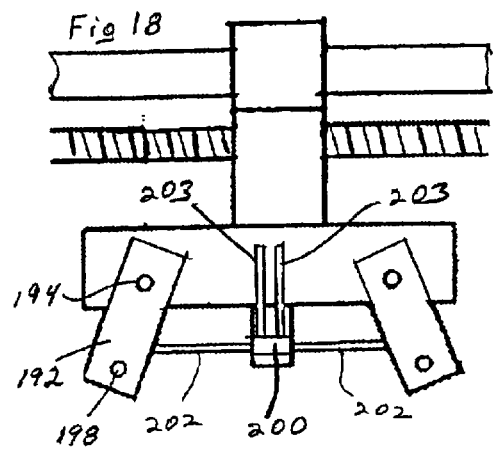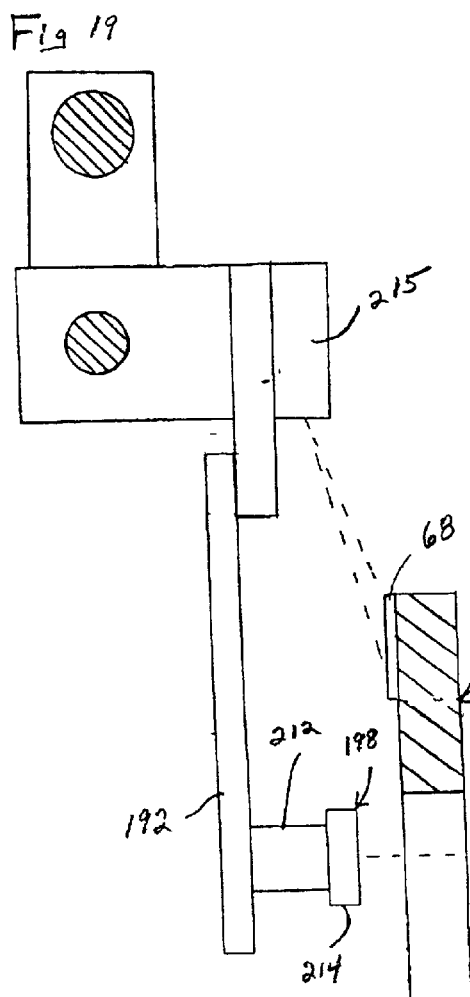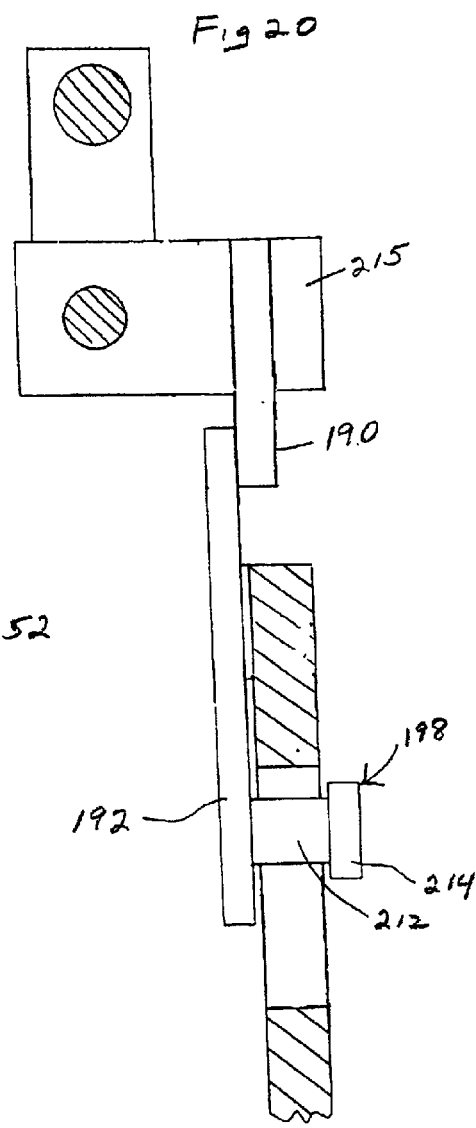

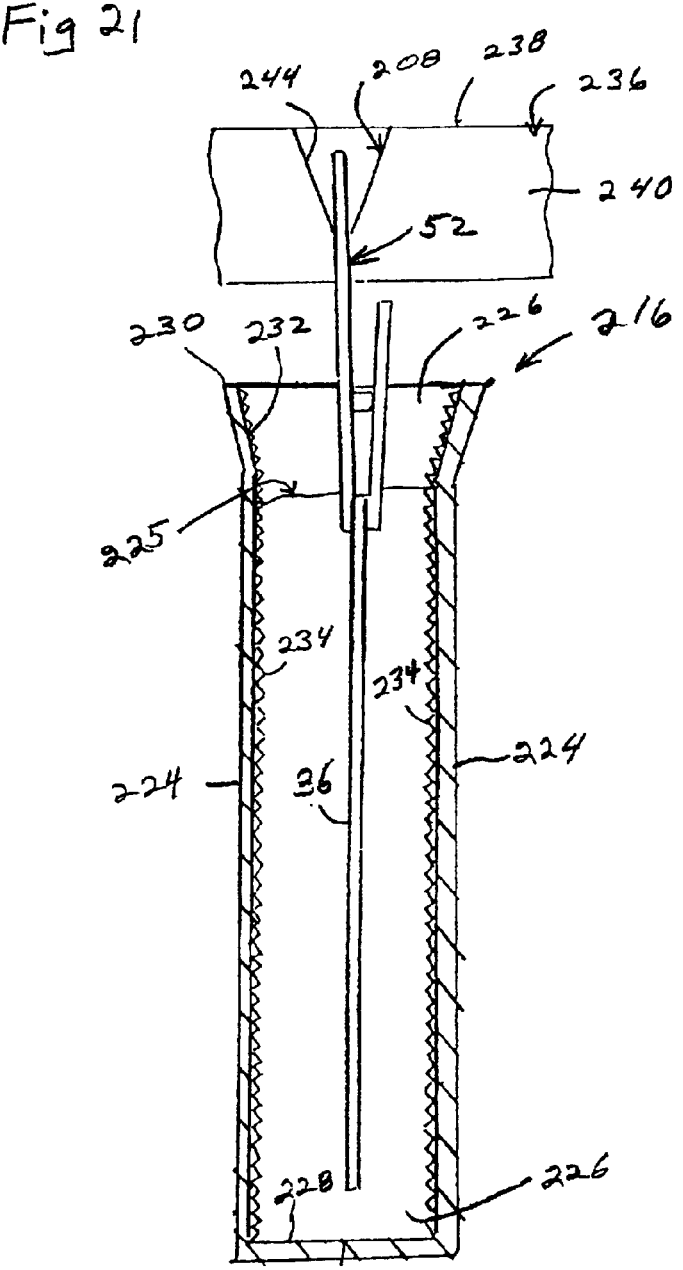

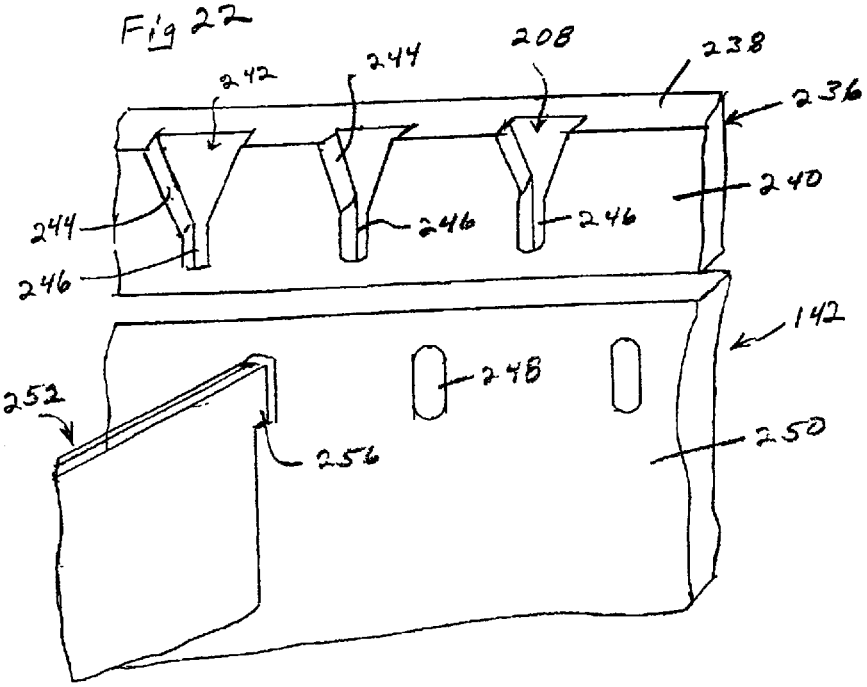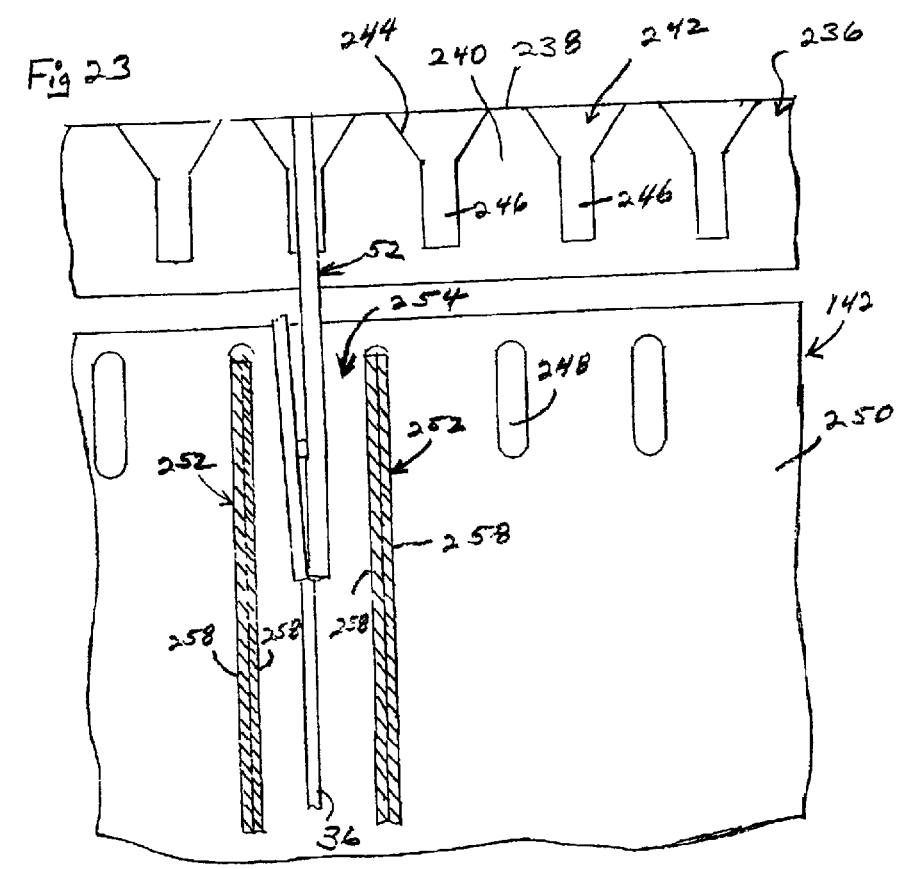

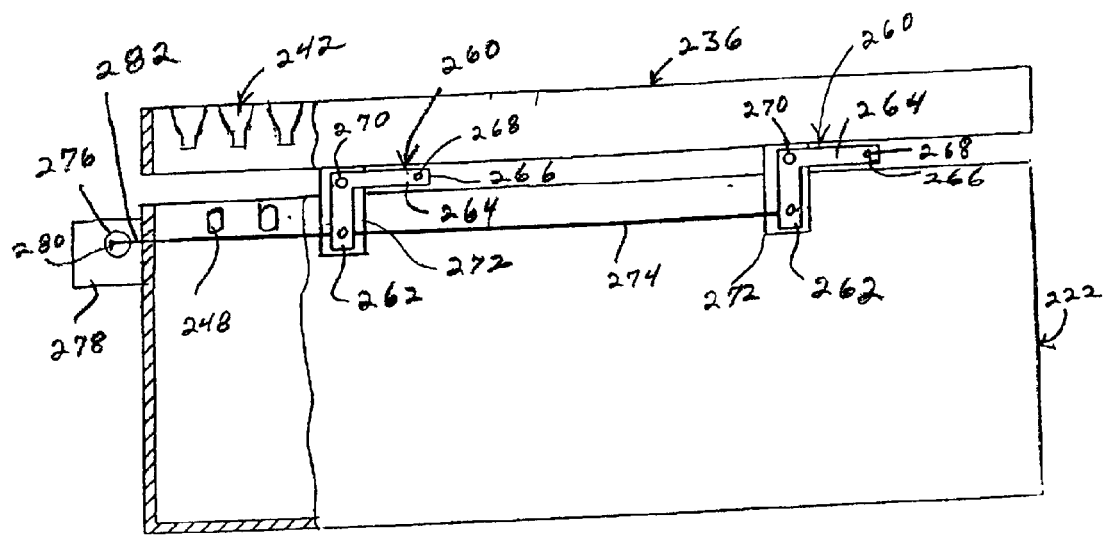
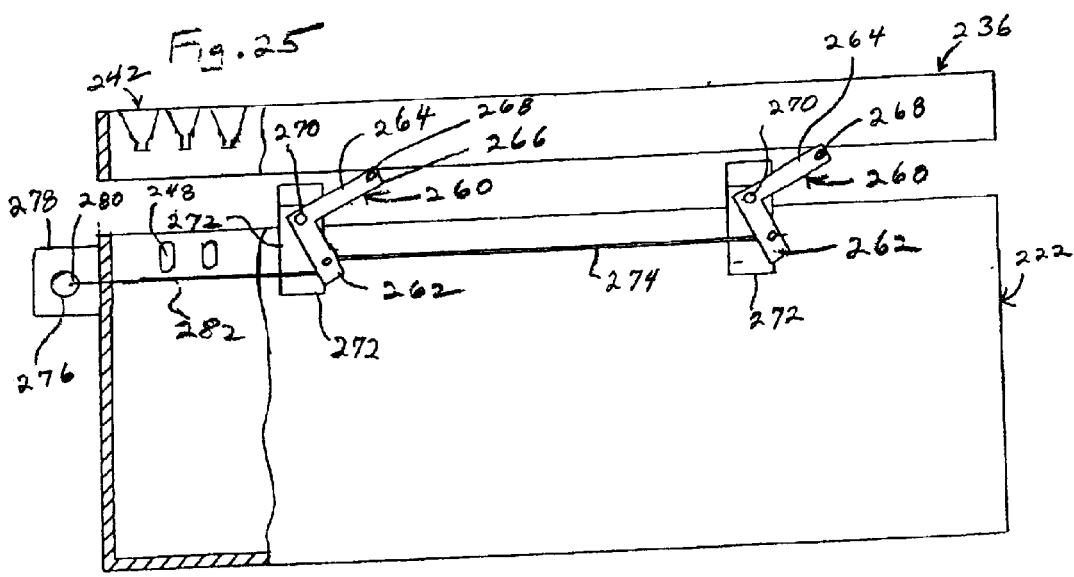

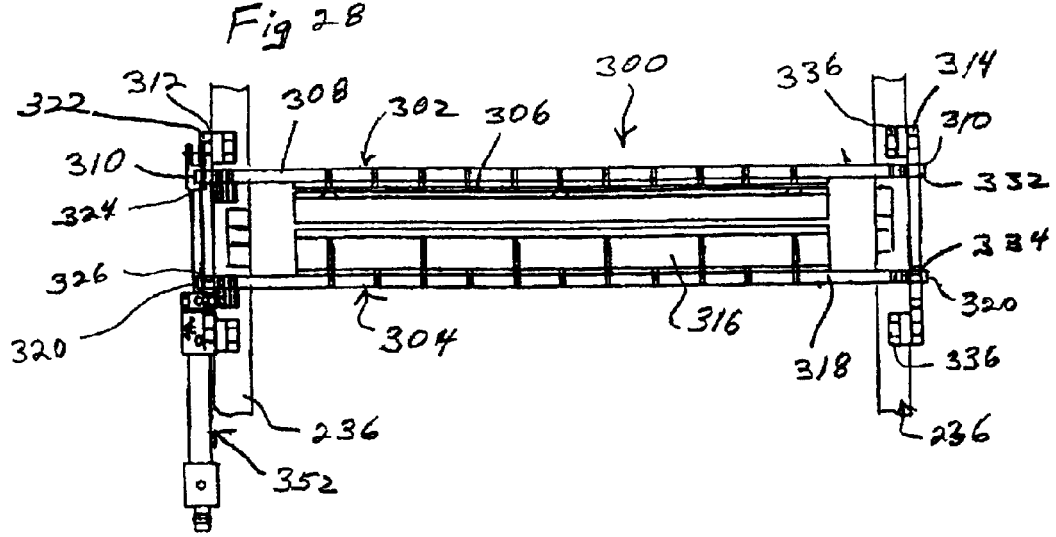
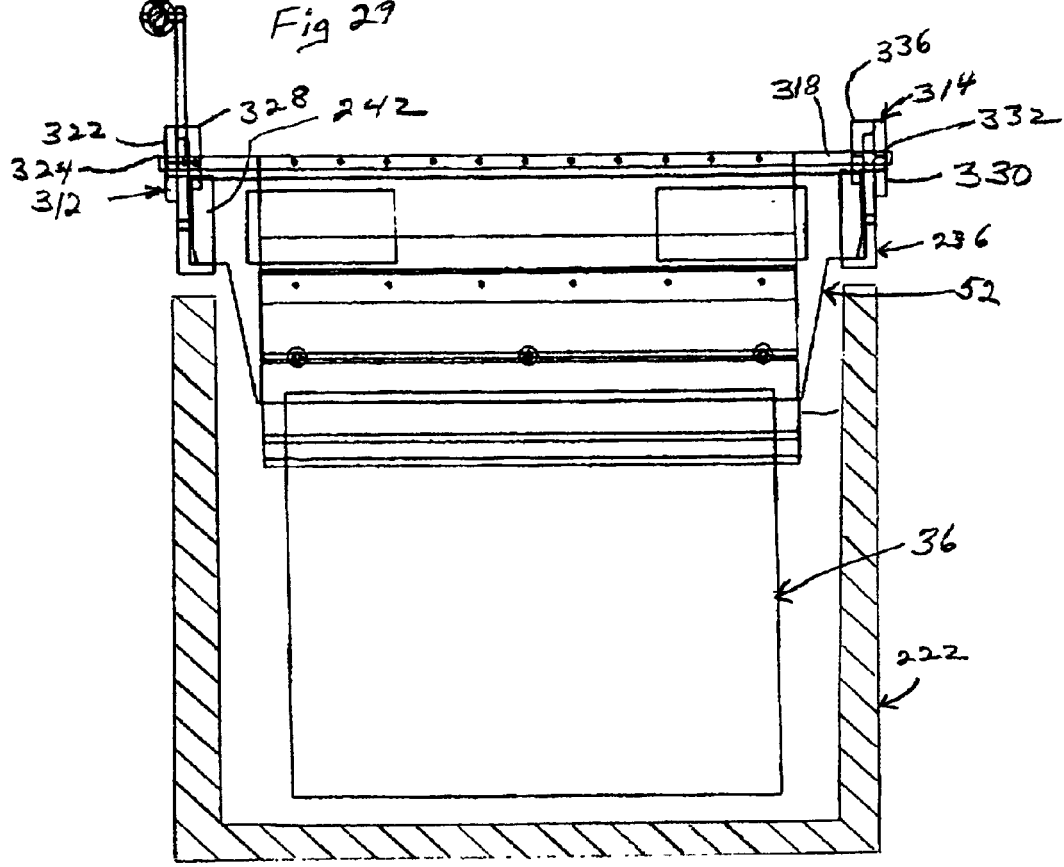

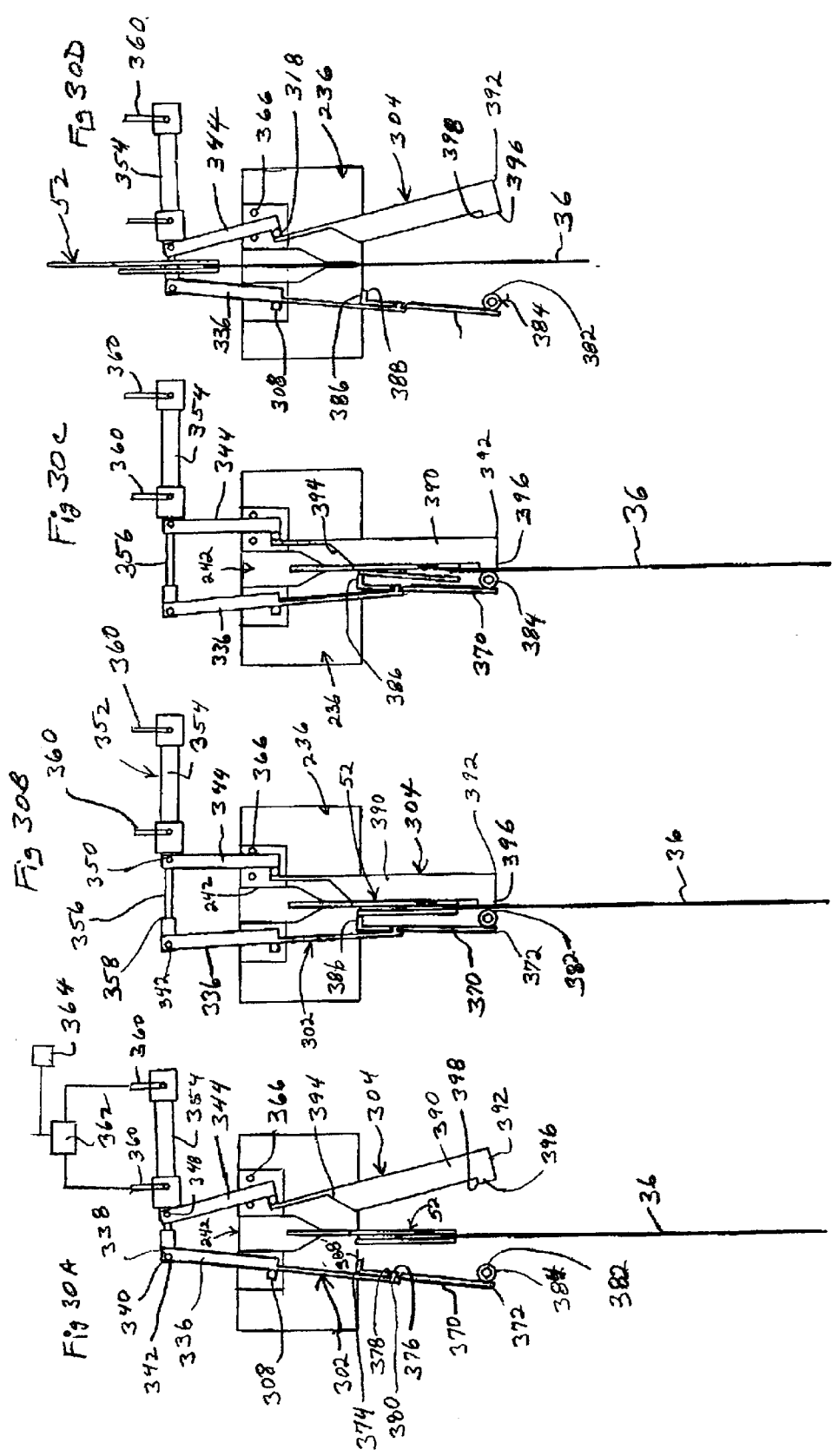

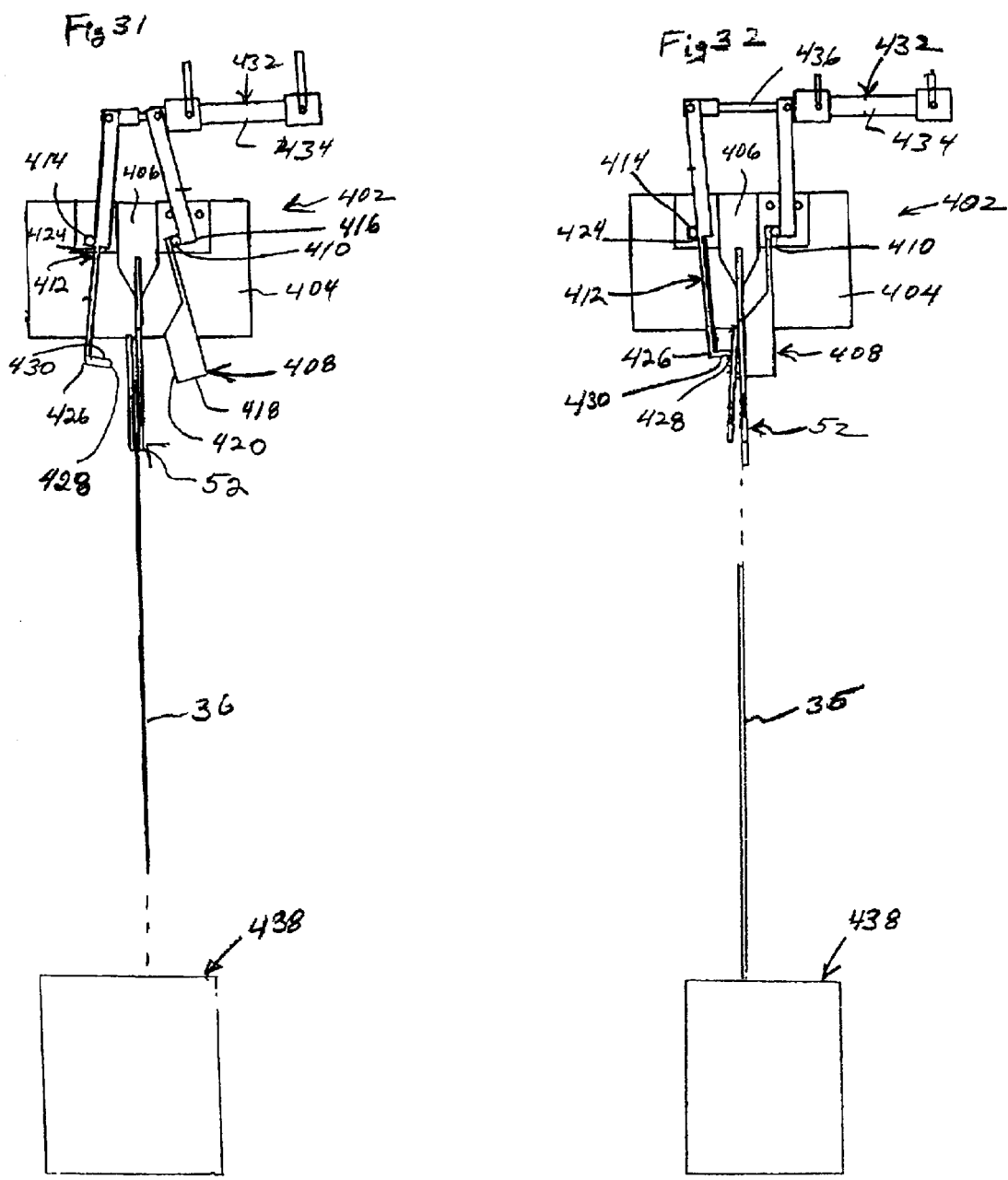

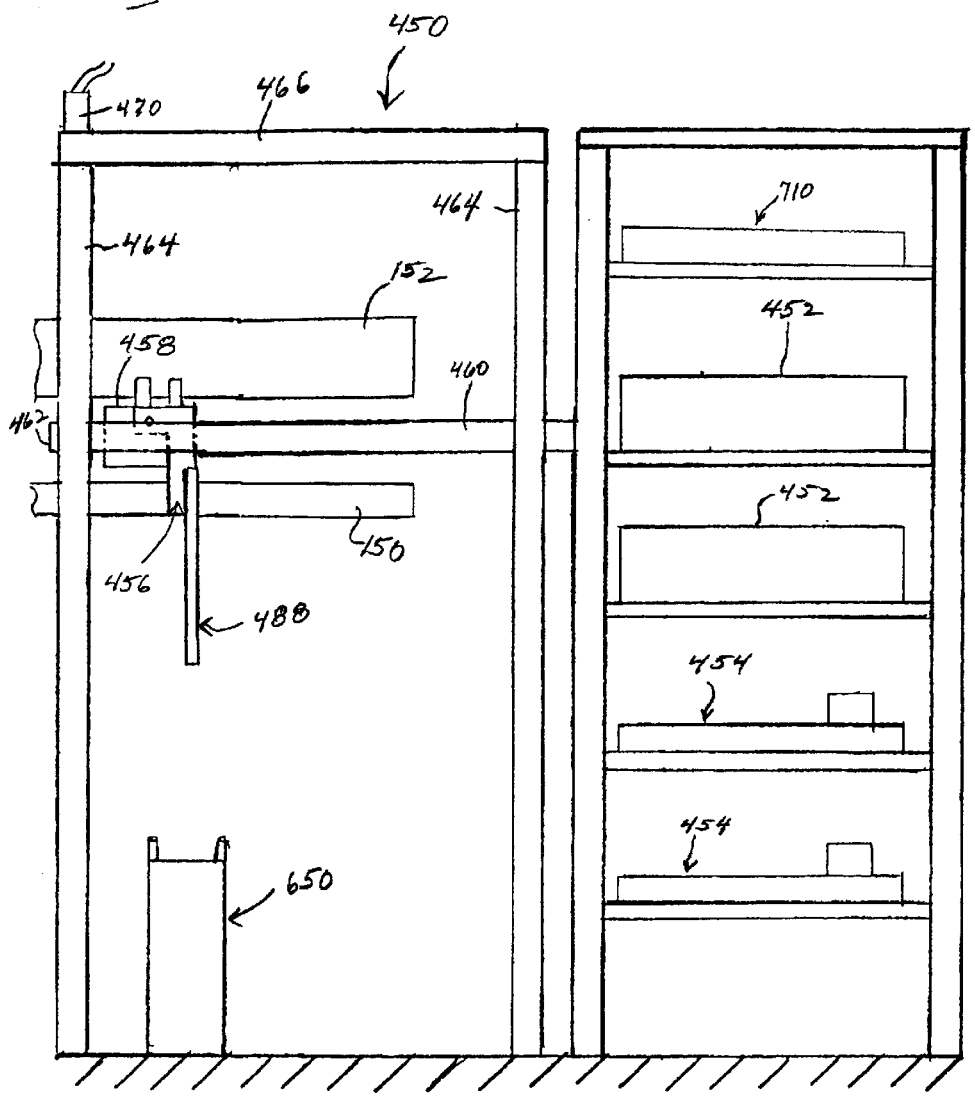

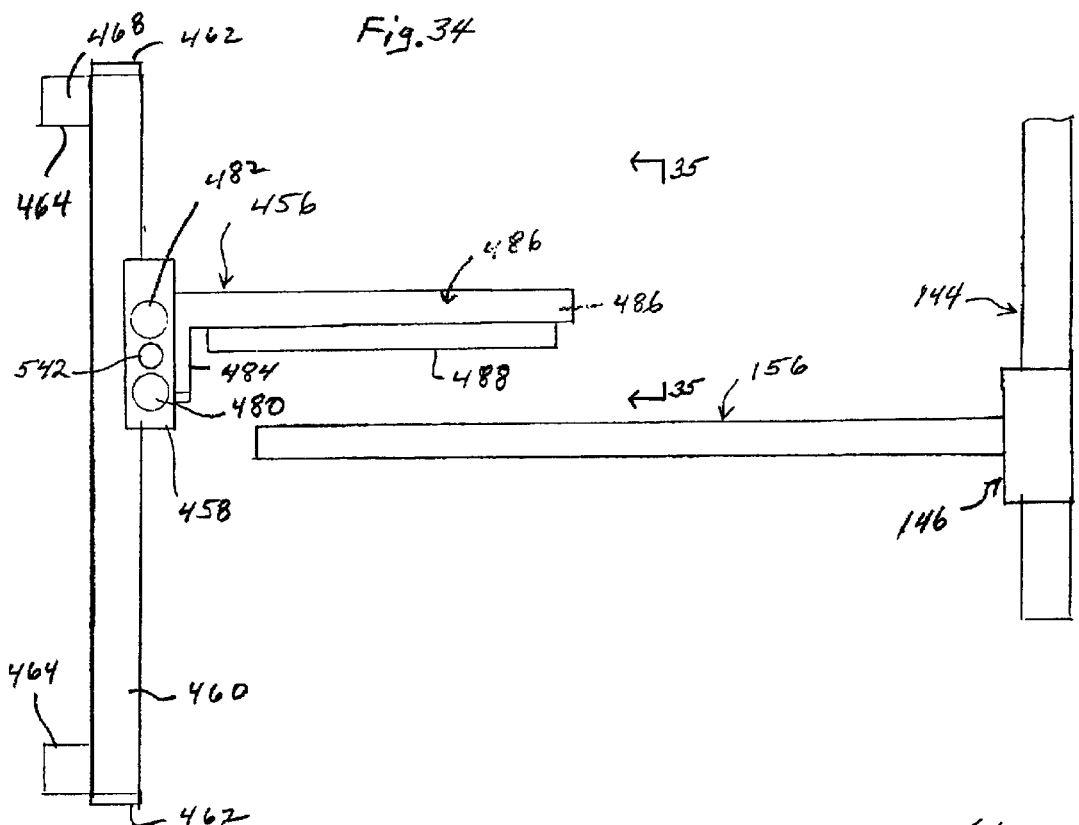
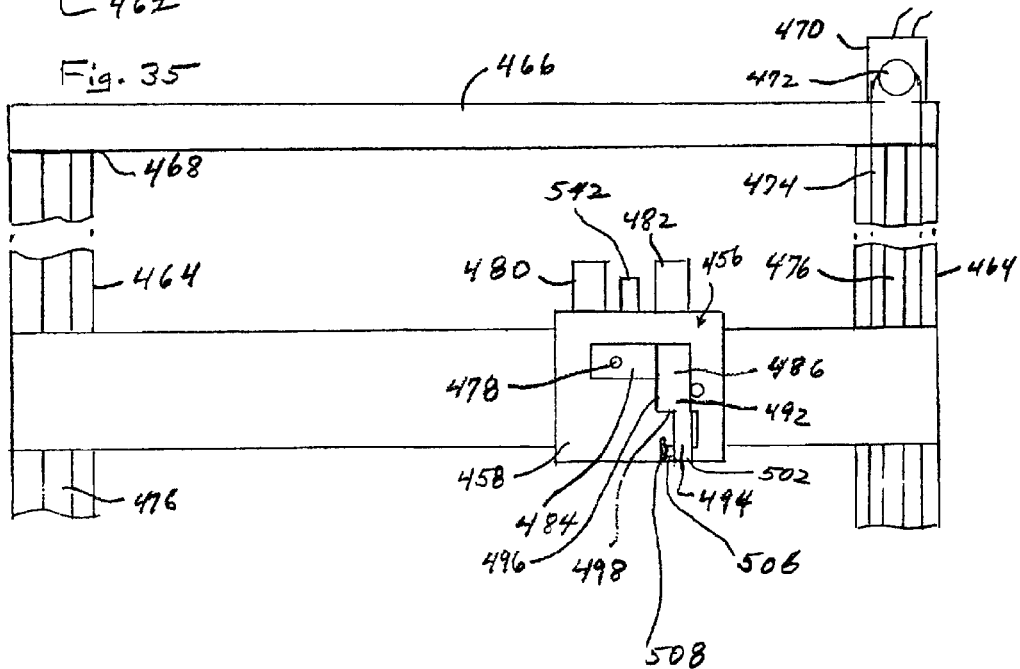

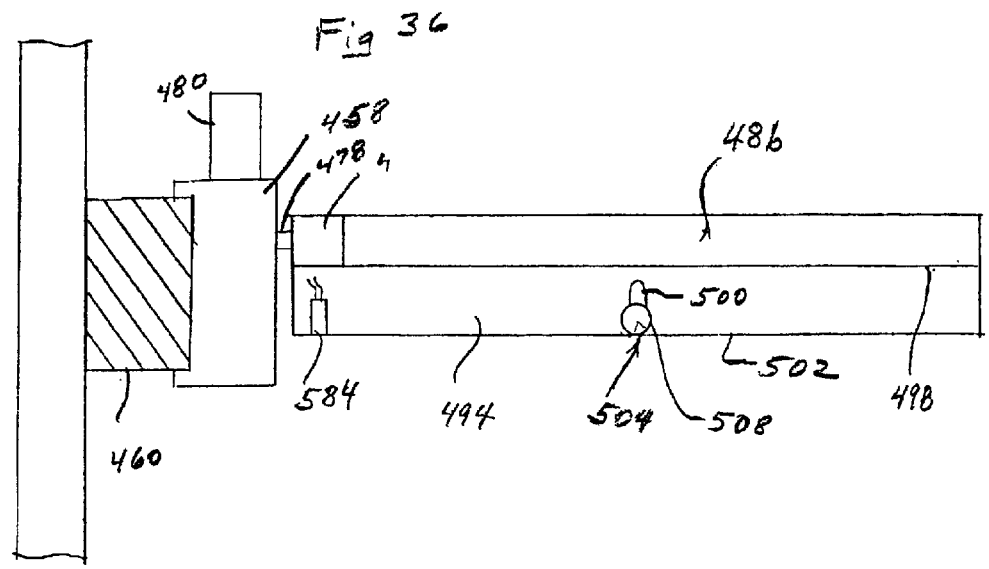
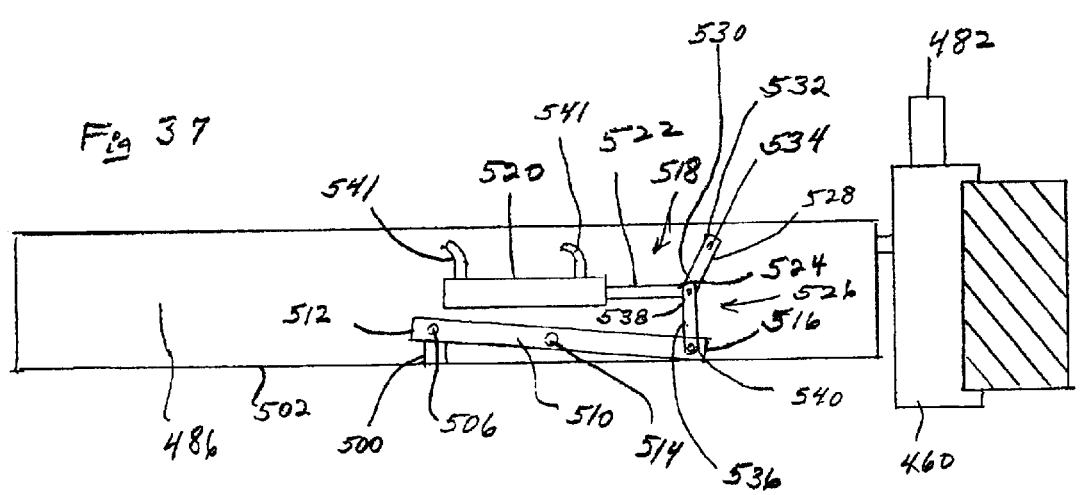

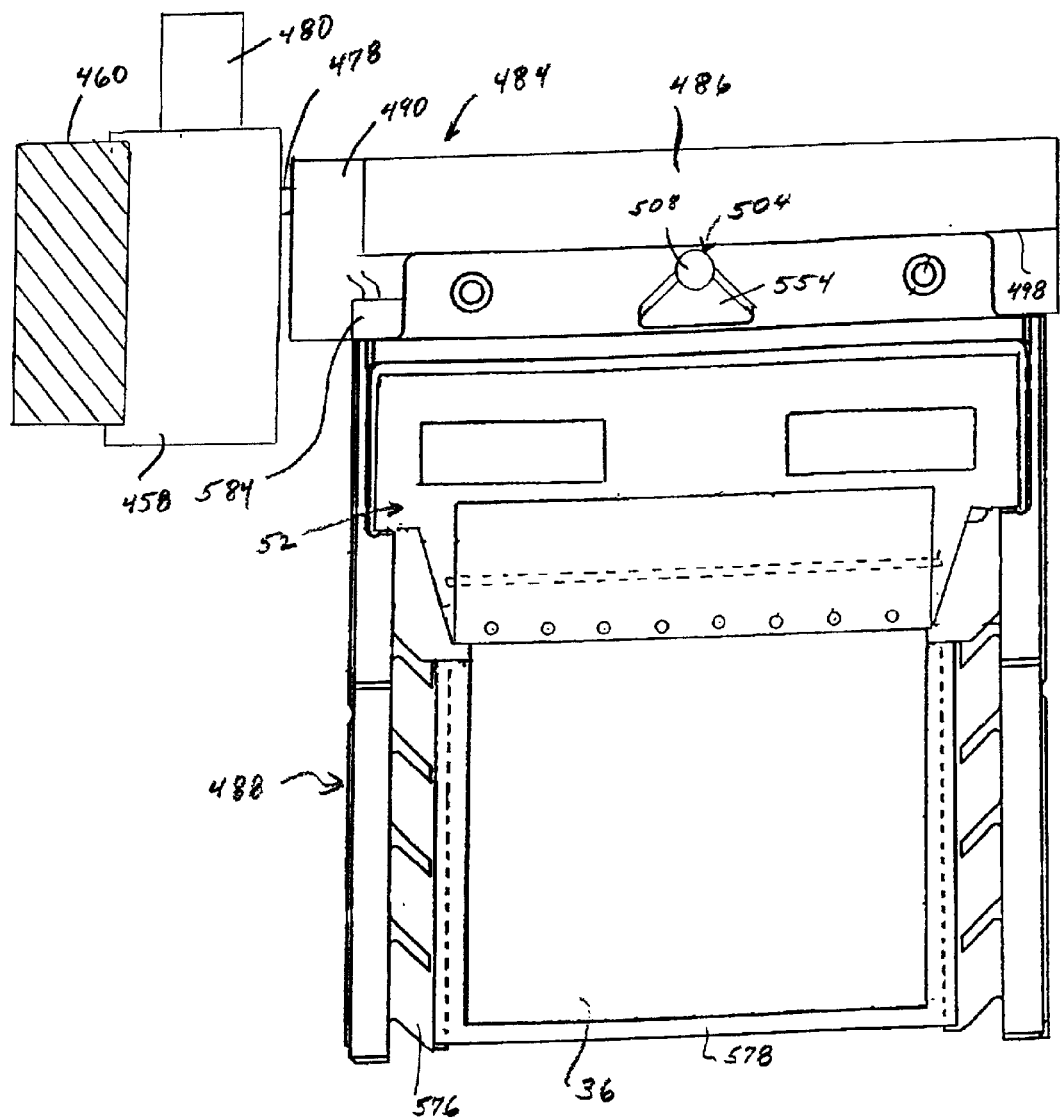

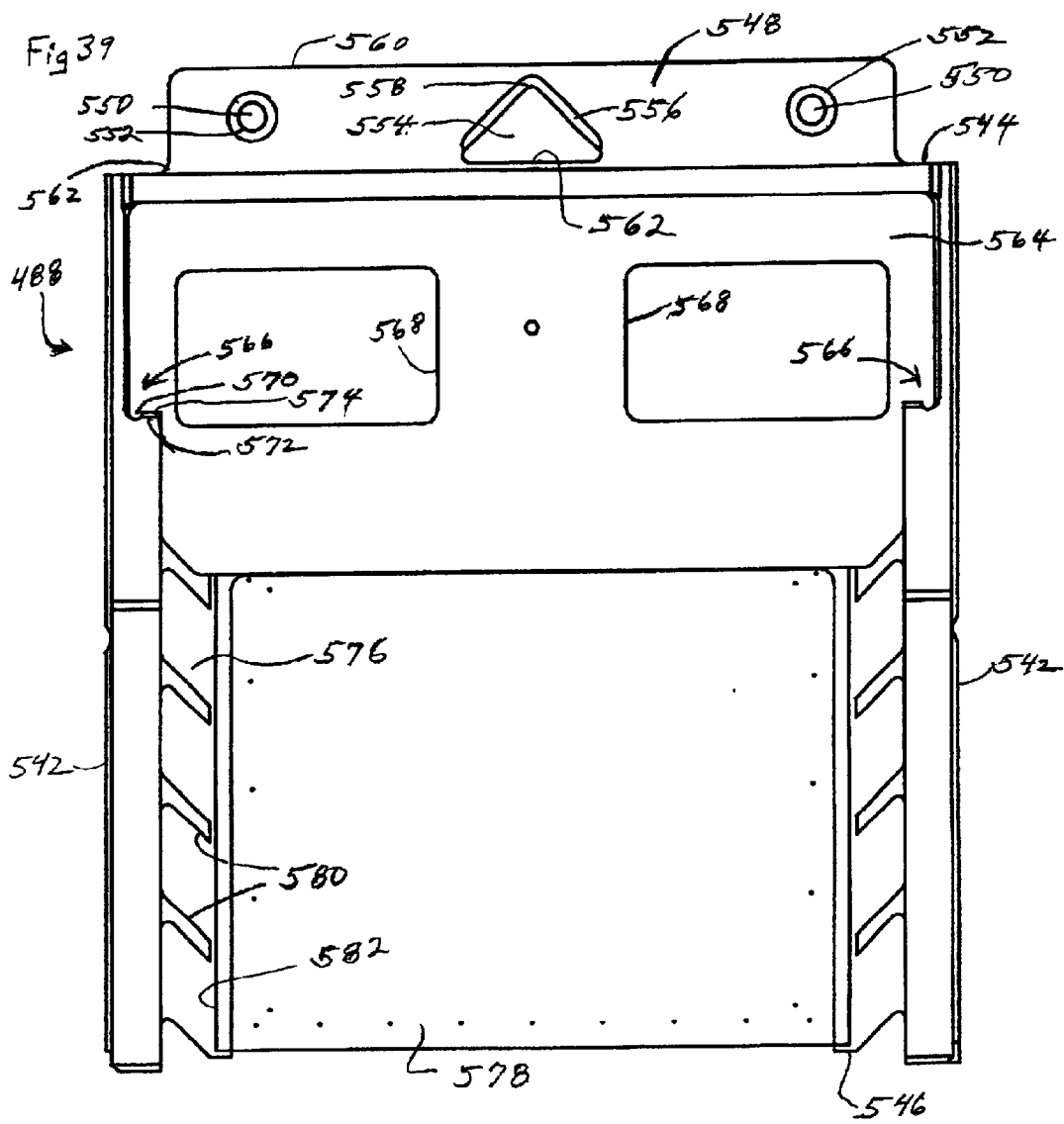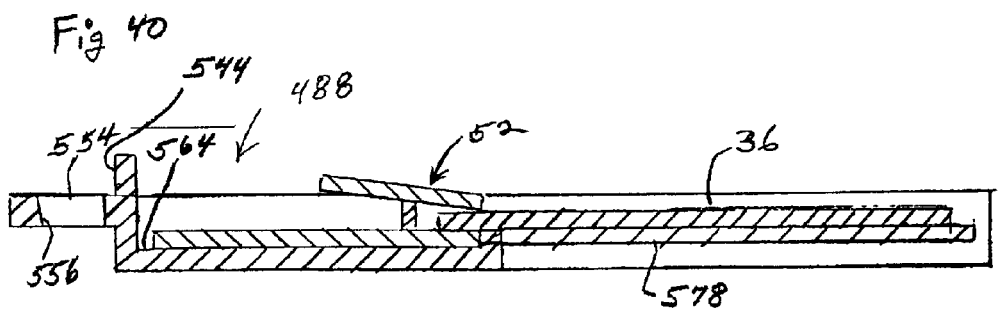

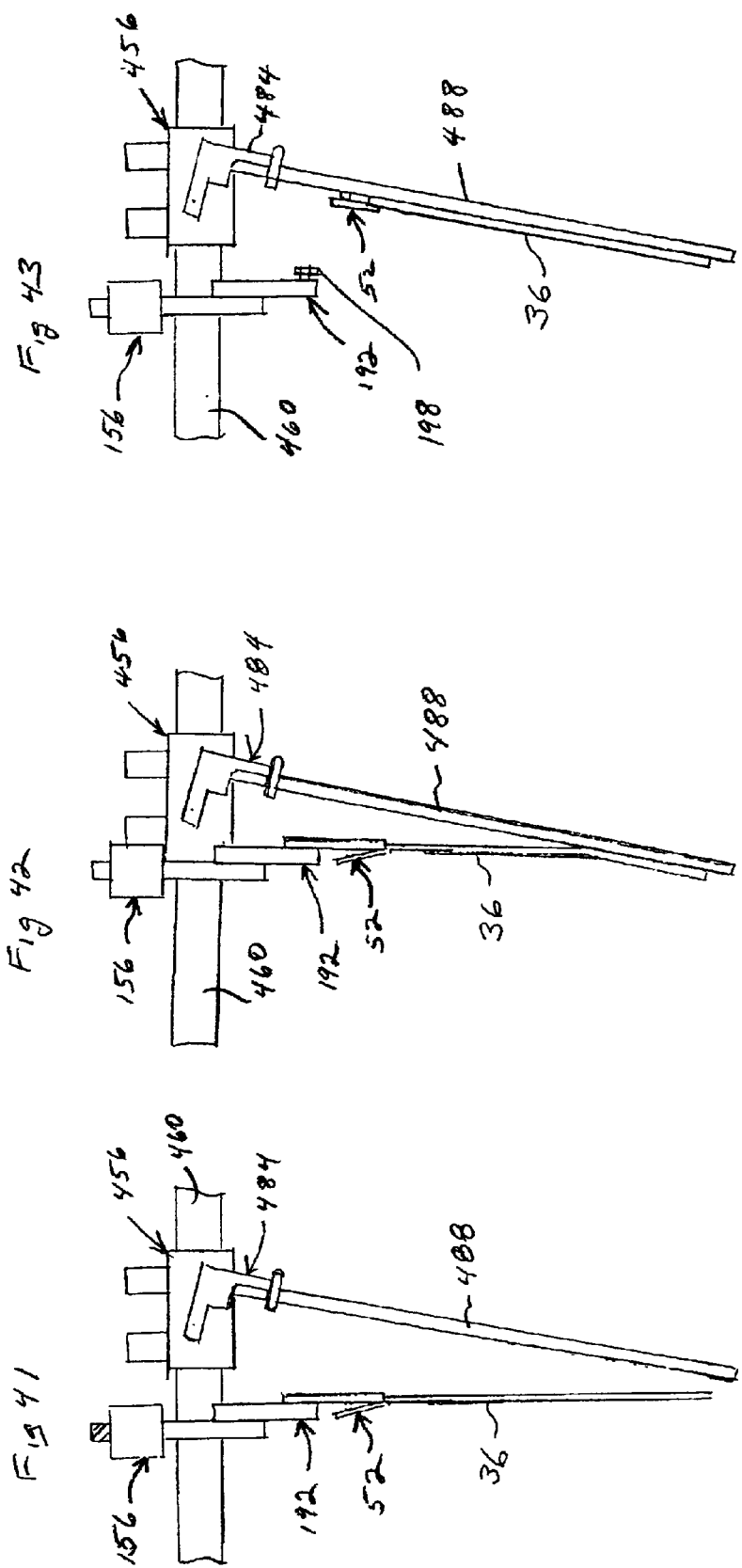

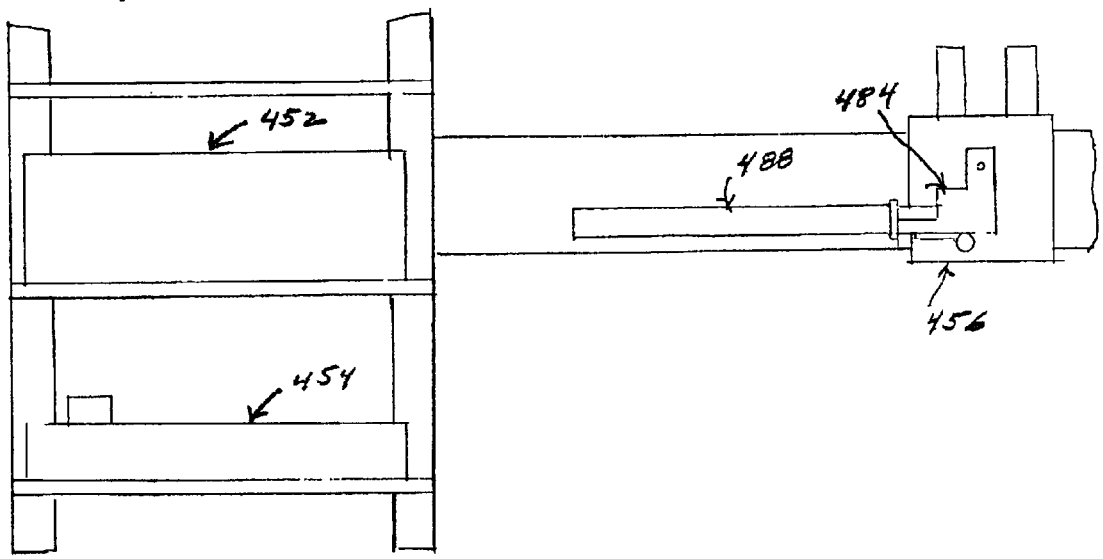
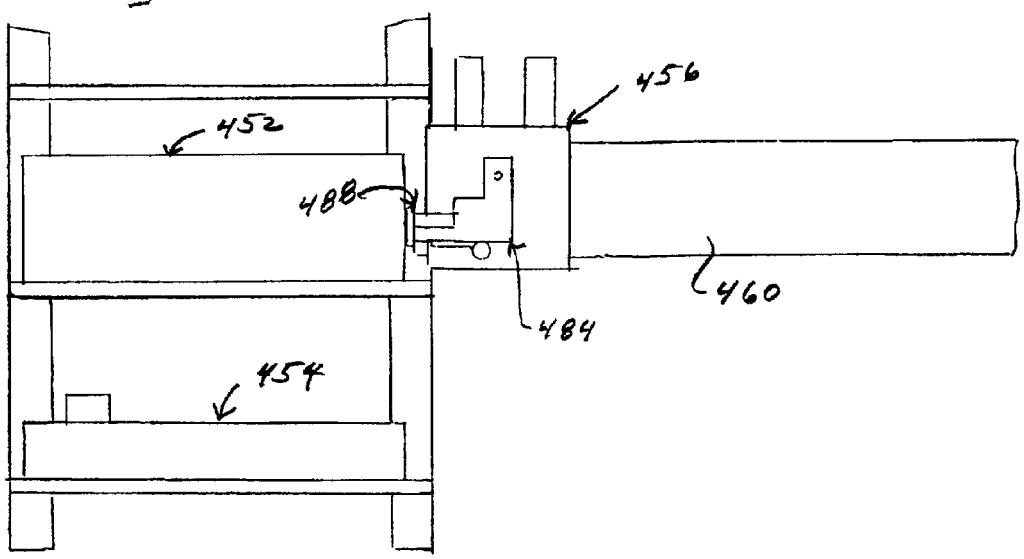

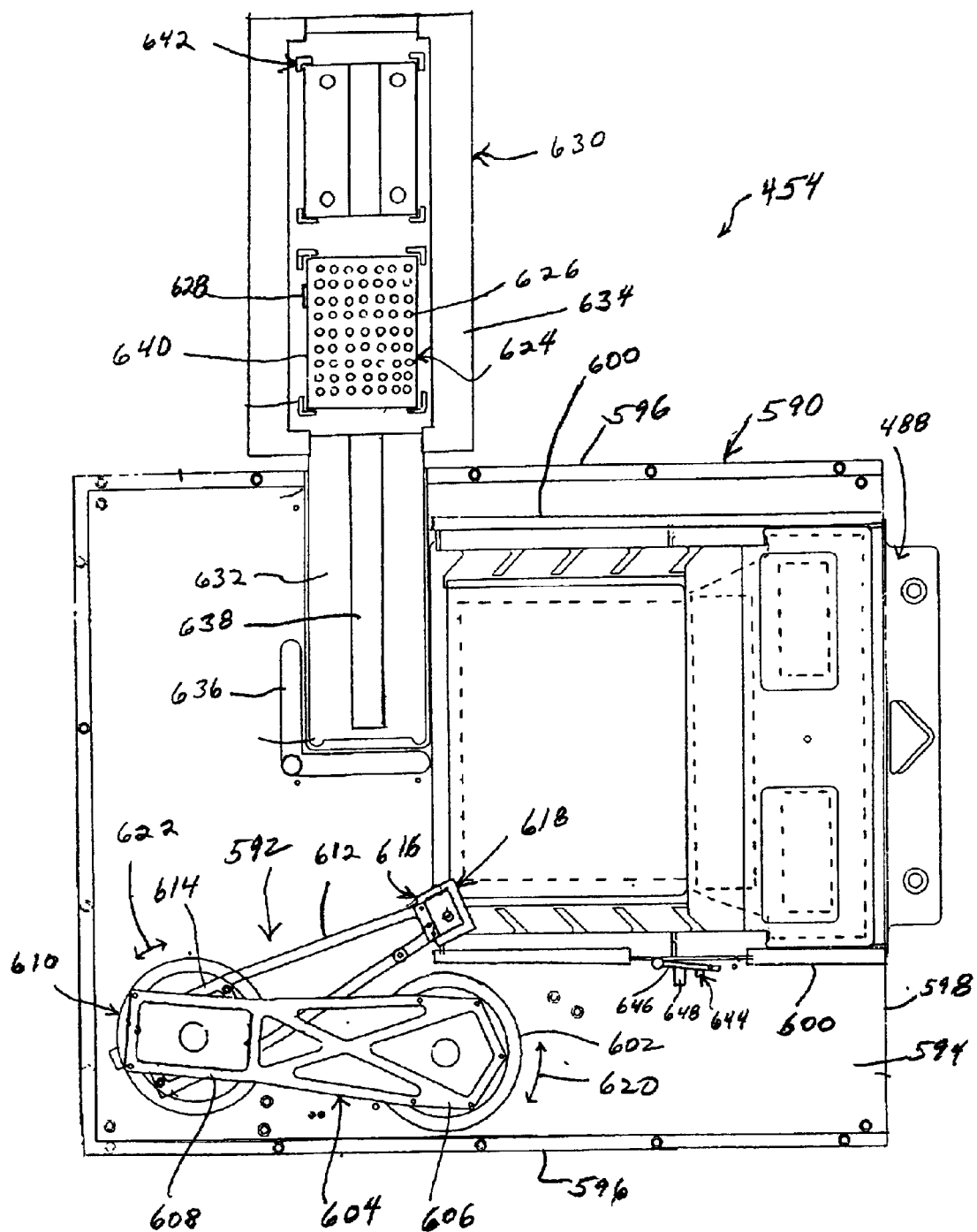

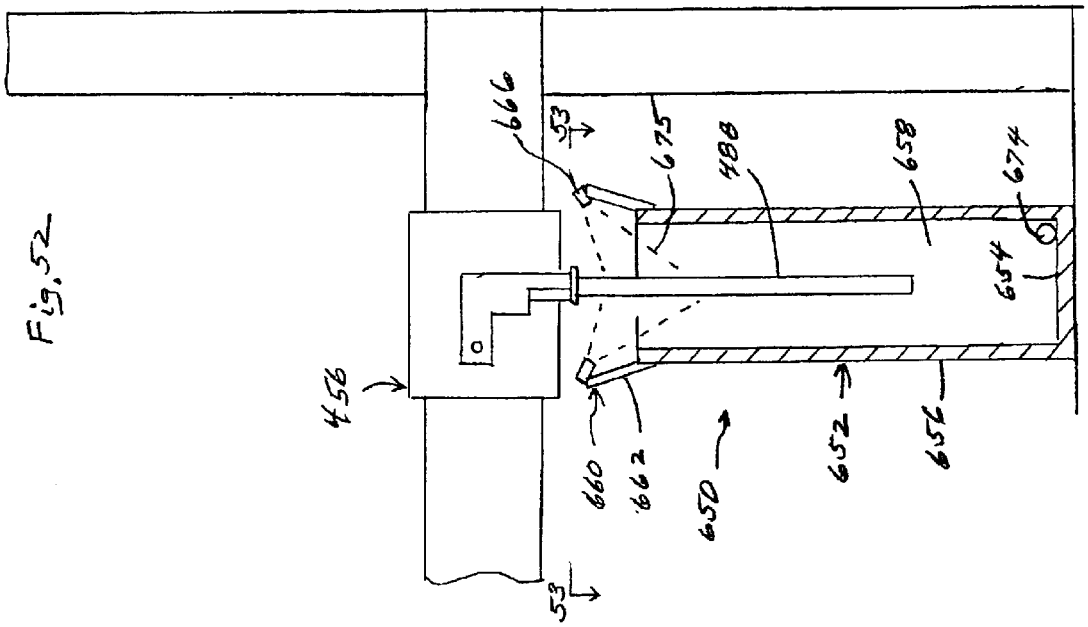
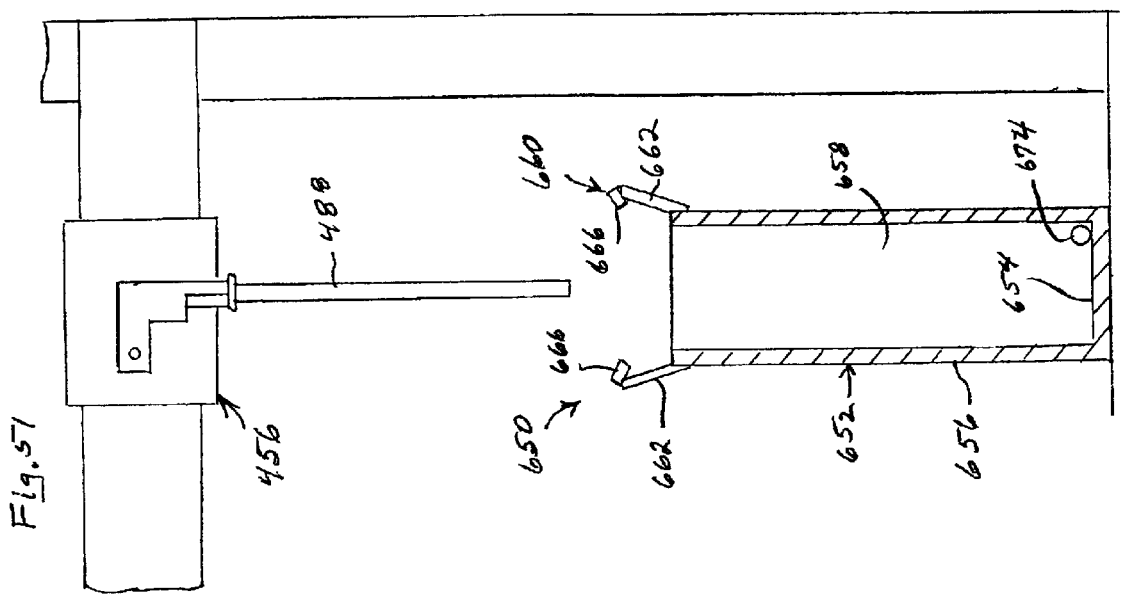

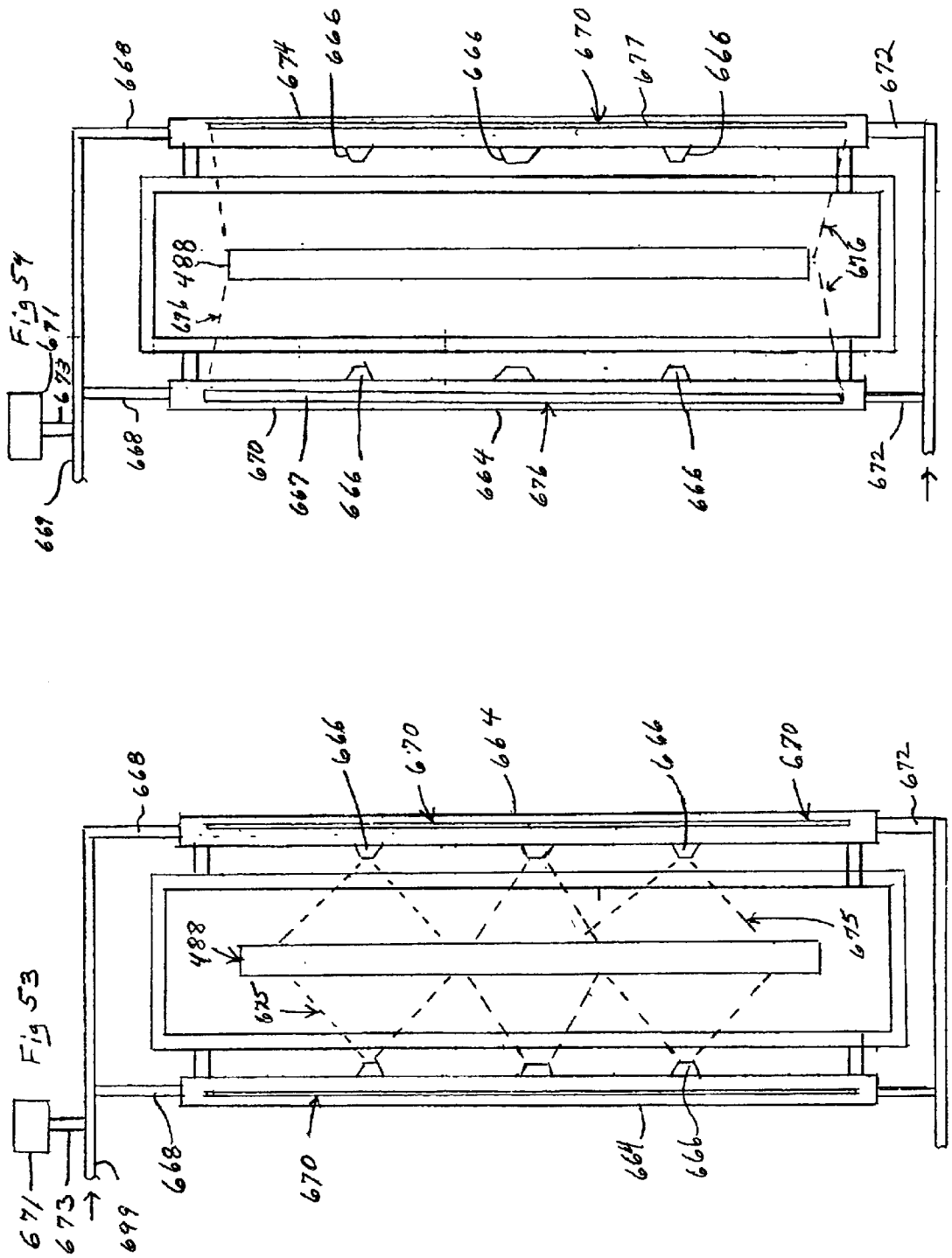

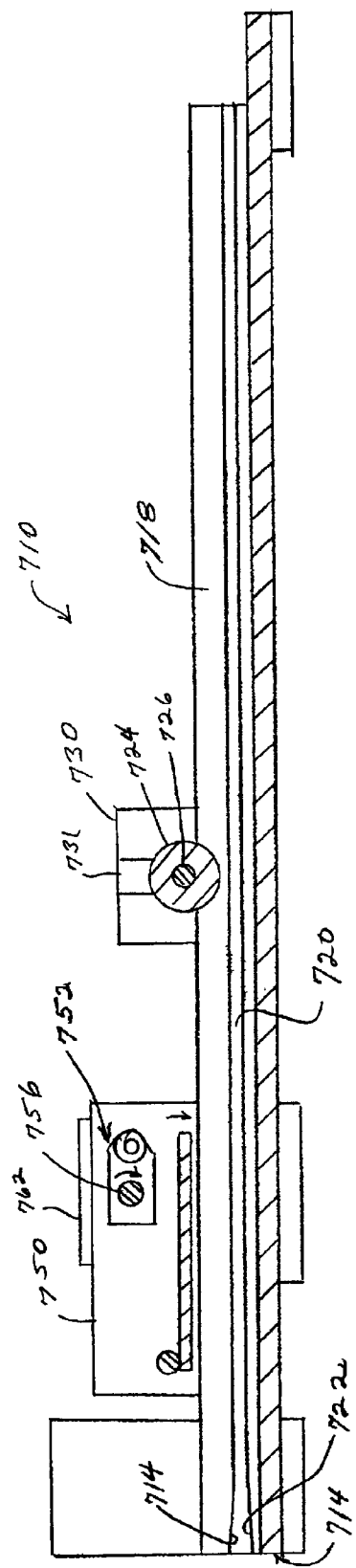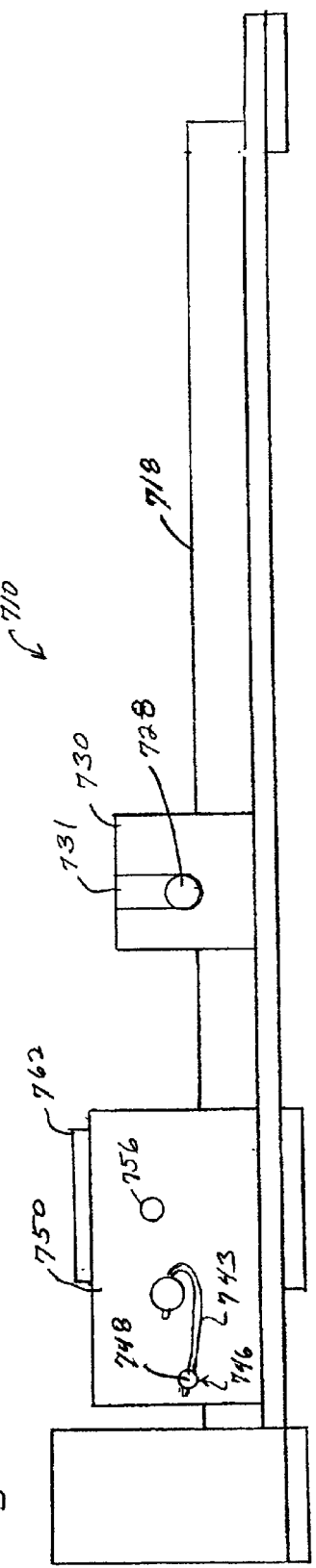

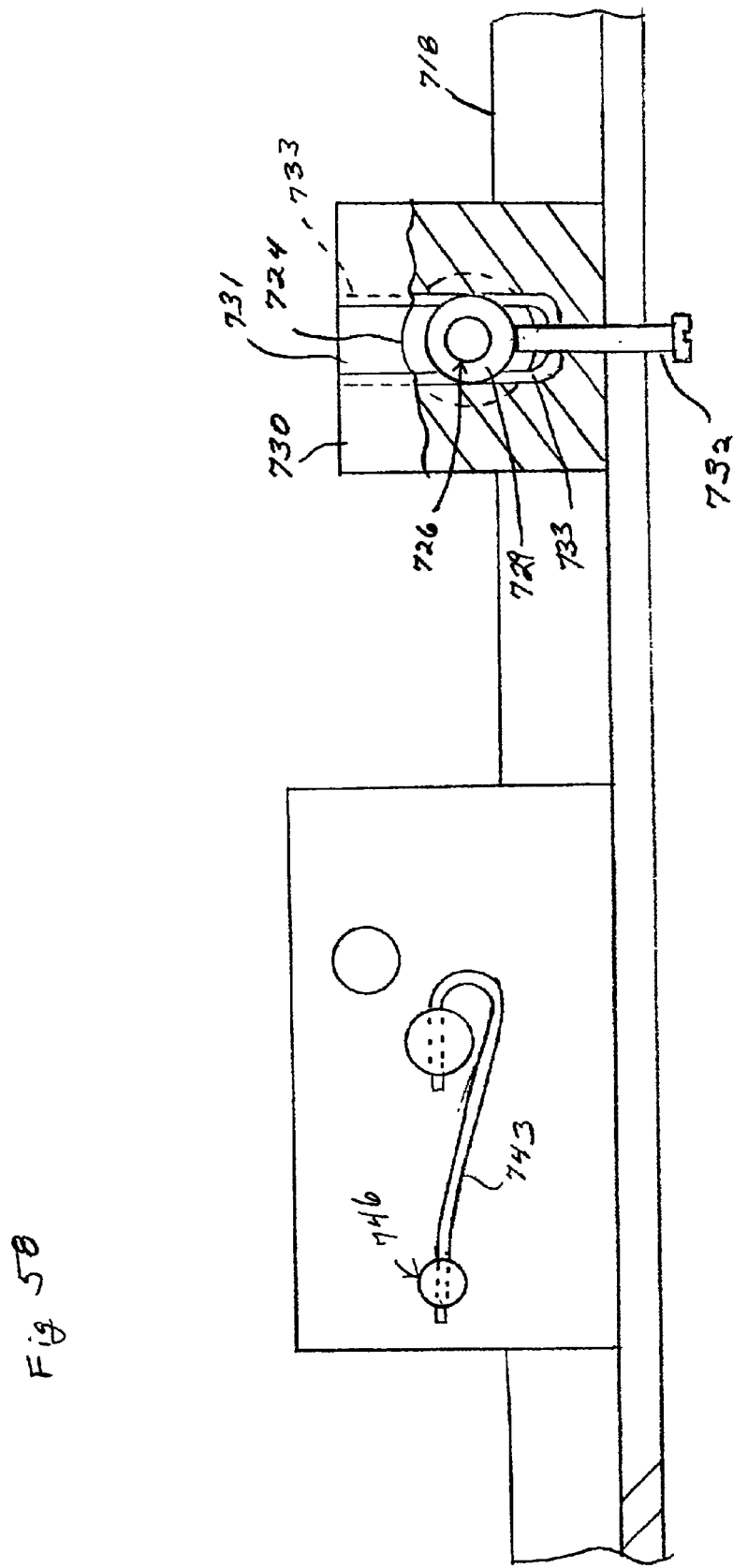

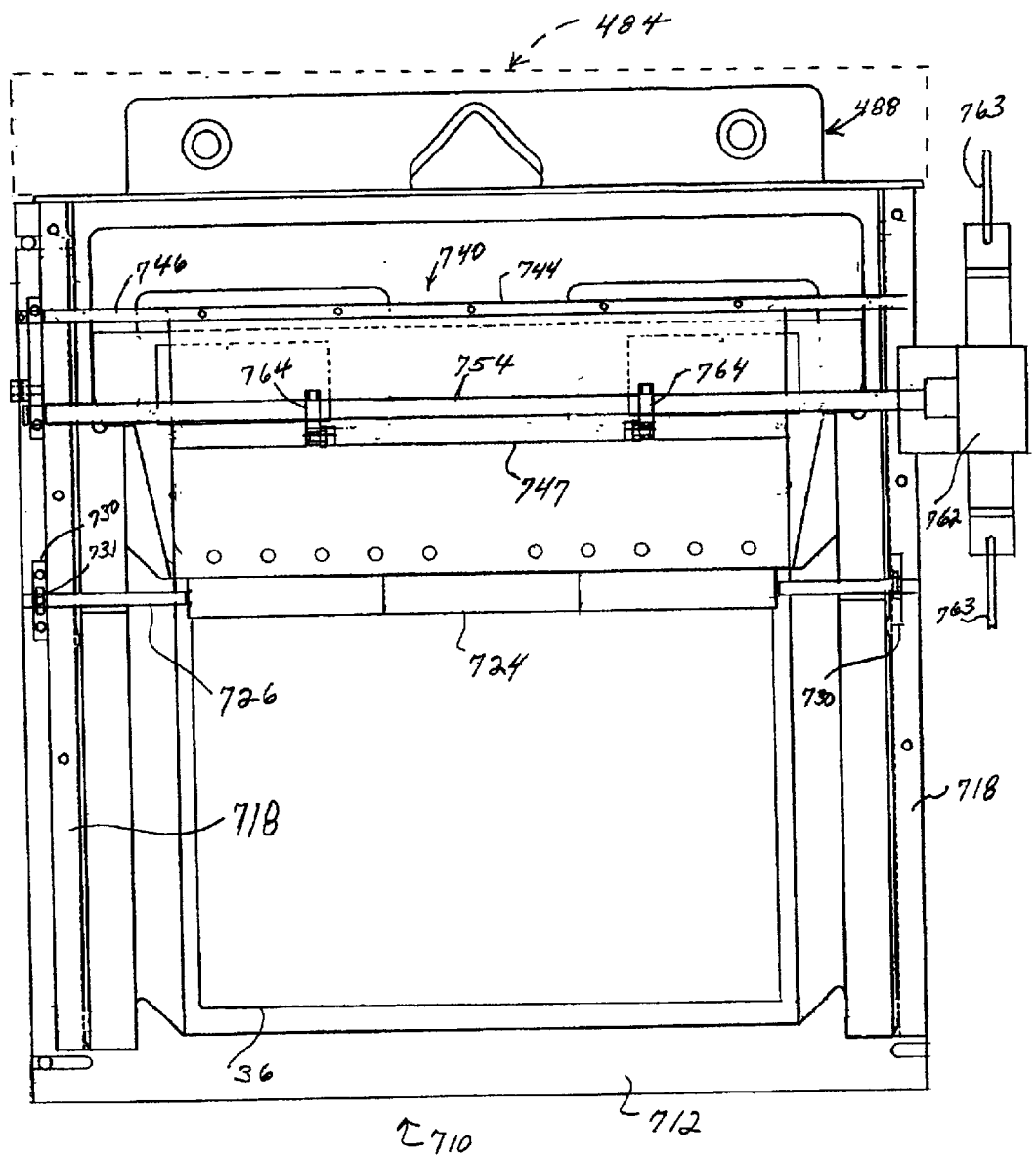

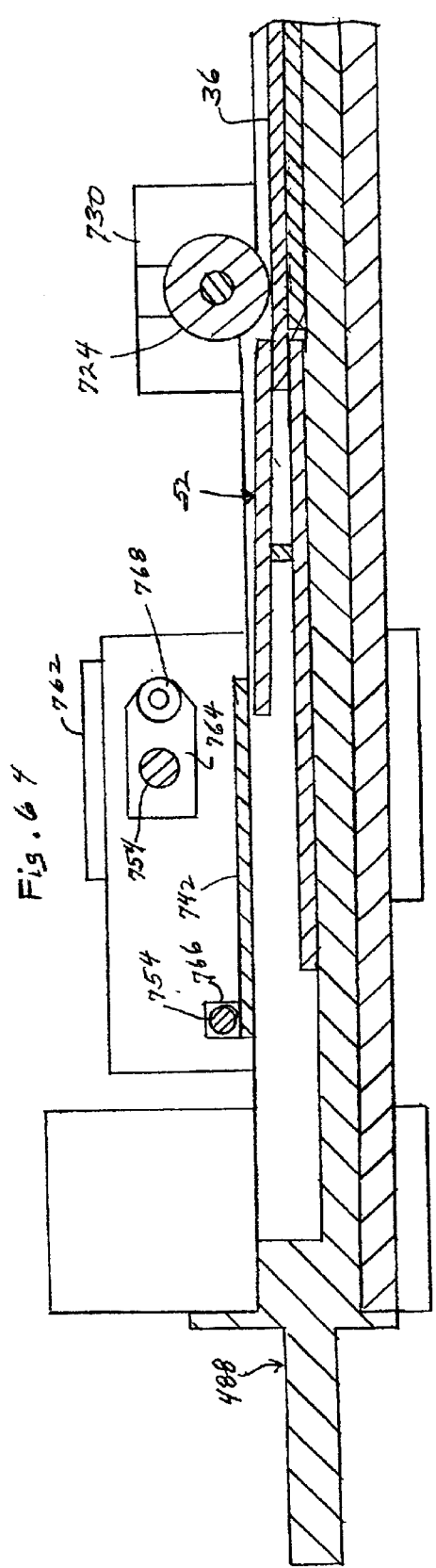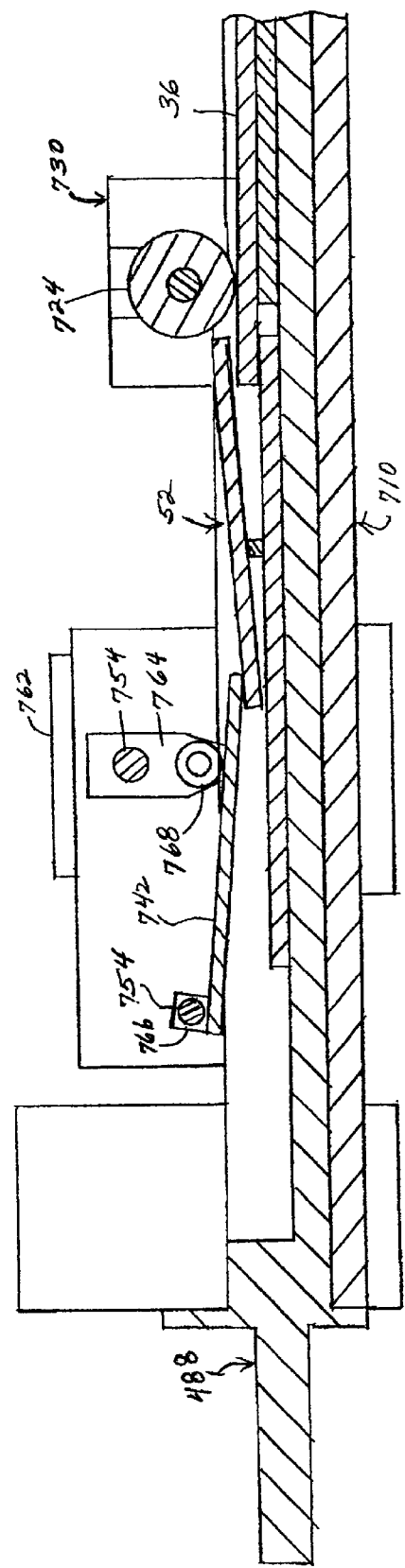

AUTOMATED ELECTROPHORESIS GEL MANIPULATION APPARATUS

CROSS-REFERENCE TO RELATED APPLICATIONS

This application claims the benefit under 35 U.S.C. § 119(e) of Provisional Application No. 60/281,000, filed Apr. 4, 2001, for "Automated Electrophoresis Gel Staining, Imaging and Cutting Apparatus and Method", which is hereby incorporated by reference in its entirety. This application is also a continuation-in-part application of U.S. application Ser. No. 09/783,132, filed Feb. 15, 2001, for "Gel Manipulation Apparatus", which is a continuation-in-part application of Ser. No. 09/504,494, filed Feb. 15, 2000, now abandoned, for "Electrophoresis Gel Clamp for Handling and Transport", and Ser. No. 09/504,493, filed Feb. 15, 2000, now U.S. Pat. No. 6,298,874, for "Slab Gel Processing Tank". This application is a continuation-in-part application of Ser. No. 09/978,574, filed Oct. 18, 2001, now abandoned, for "Method and Apparatus for Relieving Stress in an Electrophoresis Gel Slab" and Ser. No. 09/859,664, filed May 18, 2001, now U.S. Pat. No. 6,652,724, for "Automated Apparatus for Separating a Biological Sample from a Two-Dimensional Electrophoresis Gel", which applications are hereby incorporated by reference in their entirety.

FIELD OF THE INVENTION

The present invention is directed to a method and apparatus for manipulating an electrophoresis gel. The invention is also directed to an automated, computer controlled robotic assembly for transferring an electrophoresis gel between various work stations for treating the gels.

BACKGROUND OF THE INVENTION

Isoelectric focusing (IEF) is an electrophoretic technique that is commonly used for the analysis, separation and purification of various biological materials, and particularly proteins. Since many of the complex molecules of biological interest are amphoteric in nature, they are typically amenable to IEF separation. Gel electrophoresis is a process that is commonly used for protein and DNA analysis.

The separation of macromolecules, and particularly proteins, often is carried out by two-dimensional electrophoresis separation. The two-dimensional electrophoresis separation typically involves the sequential separation by isoelectric focusing of a sample in a gel tube followed by slab gel electrophoresis. The isoelectric focusing process in the gel tube is often referred to as first dimension separation.

In the first dimension separation, an isoelectric focusing gel, such as acrylamide, is placed or polymerized in a tube. The open ends of the tube are positioned in a tank with a buffer solution at each end of the tube. One end of the tube is positioned in a bath of a buffer solution such as sodium hydroxide solution. The other end of the tube is positioned in a bath of a second buffer solution such as a phosphoric acid solution. An electric current is applied to the two buffer solutions. The current together with ampholytes incorporated into the gel composition or titratable gel monomers incorporated into the gel, provides a pH gradient through the gel along the length of the tube. The sample to be analyzed is applied to a one end of the gel in the tube and an electric current is applied to an electrode in each of the buffer solutions. The molecules in the sample migrate through the gel under the influence of the electric potential until they reach their respective isoelectric point.

Slab gel electrophoresis, often referred to as second dimension separation, utilizes an electrophoresis gel molded between two glass plates. A gel strip or cylinder in which the protein sample has been resolved by the first dimension isoelectric focusing is placed along one edge of the slab gel. The ends of the gel slab are positioned in a buffer solution and an electric current is applied to each end of the gel. The proteins are then allowed to migrate through the gel slab under an applied voltage.

Charged detergents, such as sodium dodecyl sulfate, contained in the slab gel bind to the protein molecules. The detergents tend to unfold the protein molecules into rods having a length proportional to the length of the polypeptide chain and thus proportional to the molecular weight of the polypeptide. A protein complexed with a charged detergent is highly charged, which causes the protein-detergent complex to move in an applied electric field. When the slab gel, such as a polyacrylamide gel, functions as a sieve, the movement of the longer and higher molecular weight molecules is retarded compared to the shorter, lower molecular weight molecules.

Electrophoresis separation is generally labor intensive since numerous samples are run simultaneously. Generally, the gel tubes are prepared and placed in a suitable tank of buffer solutions. The protein samples are then manually placed on the end of a gel tube. When hundreds of protein samples are prepared daily for isoelectric focusing, the manual steps significantly increase the time requirements for performing the first dimension separation.

The resolution of the separation methods are sufficient to separate at least 150 proteins from a mixture. The first dimension isoelectric focusing separation followed by the second dimension SDS electrophoresis separation can result in the resolution of as many as 22,000 proteins from a single sample. A critical step in obtaining high resolution two-dimensional electrophoresis is to coordinate the first dimension separation with the second dimension separation.

The gel slab is removed from the glass plates and immersed in a series of baths containing various staining agents. Typically, the gel slabs are manually transferred from a stain bath to various fixing solutions and rinsing solutions. After the second dimension electrophoresis separation, the gel is developed to stain the proteins which appear as a spot on the gel. Thereafter, a gel spot can be identified, removed from the slab, and analyzed.

Various automated devices are known for performing various analysis processes of proteins and DNA. One example is disclosed in U.S. Pat. No. 5,865,975 to Bishop. The disclosed system uses an automated protein and DNA gene fragments analyzing machine where electrophoresis cells are robotically inserted into an electrophoresis housing for producing electrophoretic migration of the protein in one dimension. The robotic assembly rotates the cells 90° to enable separation of the fragments vertically in a second dimension.

The gel slabs are made of a flexible gel and care must be taken to prevent damaging or tearing the gel. During handling and manipulating, the gel slab adheres to surfaces that it contacts. As the gel is pulled from the surface, the gel can tear or stretch. Various devices have been proposed for handling and manipulating gel slabs. However, these devices have experienced only limited success. Accordingly, there is a continuing need in the industry for improved methods and devices for handling and processing electrophoresis gels.

SUMMARY OF THE INVENTION

The present invention is directed to a method and apparatus for manipulating an electrophoresis gel. The invention is also directed to an automated, computer controlled system having a robotic assembly for transferring an electrophoresis gel between various work stations for treating and processing the gels.

Accordingly a primary aspect of the invention is to provide an automated apparatus for manipulating an electrophoresis gel and transferring the gel from a storage tank to one or more gel processing tanks according to a preselected processing protocol for the gel.

Another aspect of the invention is to provide an automated apparatus having a robotic arm that is controlled by a computer to selectively transfer an electrophoresis gel between selected work stations and to monitor the location of the gel within the apparatus.

A further aspect of the invention is to provide a computer-controlled robotic apparatus for manipulating an electrophoresis gel along three coordinates so that the gel can be moved in three dimensions between selected work stations.

Still another aspect of the invention is to provide a computer controlled articulated arm that is movable on a boom, where the boom can be moved in a horizontal direction and in a vertical direction and where the articulated arm is movable along the length of the boom.

A further aspect of the invention is to provide an automated computer controlled apparatus having an articulated robotic arm that is able to move into a selected position and capture an electrophoresis gel attached to a carrier, transfer the gel to a selected location, release the captured gel at the selected location and substantially retrieve the gel.

Another aspect of the invention is to provide a carrier device for capturing an electrophoresis gel where the gel can be suspended from the carrier without damaging or tearing the gel while the gel is being transferred between selected locations.

Still another aspect of the invention is to provide a clamp device that is able to capture an electrophoresis gel and suspend the gel without damaging the gel.

Another aspect of the invention is to provide a clamp device having a pair of jaws that are biased together by at least one magnet on each of the jaws.

A further aspect of the invention is to provide a staining tank for an electrophoresis gel where the tank has an agitating assembly that is able to move the gel within the tank.

Another aspect of the invention is to provide an agitating device for an electrophoresis gel staining tank where the agitating device moves the gel in a reciprocating motion in a substantially vertical direction.

Still another aspect of the invention is to provide a tank for treating an electrophoresis gel where the tank has at least one wall having a surface texture that resists or inhibits the gel from adhering to the wall.

A further aspect of the invention is to provide a tank for treating an electrophoresis gel where the tank includes at least one divider that can be removable to separate adjacent gels in the tank and where the divider has a surface that inhibits the gel from adhering to the divider.

A further aspect of the invention is to provide an automated electrophoresis gel processing tank having a computer controlled apparatus for identifying an electrophoresis gel and selecting a processing protocol specific for the gel and the biological sample contained in the gel, transporting the gel to predetermined locations and monitoring the location of the gel within the assembly.

The apparatus of the invention basically comprises a robotic assembly that is controlled by a computer or central processing unit to control the movement of the assembly and coordinate the operation of the various devices of the assembly. The apparatus includes a robotic arm that is able to capture and manipulate electrophoresis gels between selected processing stations in sequence and according to a selected processing protocol for each electrophoresis gel. The computer is programmed to selectively transfer the gel to selected stations where the gel is processed for a predetermined period of time. At the same time the computer records the location of the gel and the progress of the process at each stage. The robotic assembly has an articulated arm that can be moved to an infinite number of locations within the apparatus. In one embodiment of the invention the robotic assembly has a boom that can travel in a horizontal direction and in a vertical direction with respect to the plane of the assembly. At the same time the articulated arm can travel along the length of the boom to selected positions to enable transferring of the gel between the various locations of the apparatus.

The automated apparatus is primarily directed for use with a loading apparatus, staining apparatus, scanning and automated cutting apparatus for the sequential staining, scanning and cutting steps of an electrophoresis gel staining process. The automated apparatus is controlled by a computer or central processing unit that is able to control a robotic assembly of the staining apparatus and transfer the gel to a robotic apparatus of the scanning and cutting apparatus. The apparatus has a plurality of staining tanks that include an agitator for moving the gel in a vertical direction to agitate the staining liquid continuously. The agitator includes a reciprocating frame. The gels are suspended in the staining liquid by the frame which reciprocates in a vertical direction to agitate the liquid.

The carrier of the invention is a clamp member that is able to capture a gel along one edge so that the gel can be suspended vertically by the clamp without damaging the gels. The clamp has two jaws that are held together by at least one magnet on each jaw. Preferably, each jaw has a magnet oriented to be attracted to the magnet on the opposing jaw to attract the clamping edges of the jaws. The magnets can be bar magnets or a strip of magnetic material that is attached to a gripping edge of the jaws.

The present invention is primarily directed to an automated system for processing electrophoresis gel slabs to stain the protein spots that have been separated by the electrophoresis process, identifying selected protein spots for protein extraction and analysis and separating the protein spots from the gel. The automated system includes a computer for operating the robotic assemblies and tracking the location of the gel slabs during the various phases of the process.

The apparatus of the invention basically includes a loading station for separating the gel from the glass plates and loading the gel into a carrier for handling the gel, a gel staining station for staining the proteins in the gel, and a gel scanning and cutting station. The computer controlled apparatus includes a detector for identifying a gel slab, selecting a staining protocol specific for the gel and transferring the gel to selected staining solution in the staining apparatus according to the selected staining protocol. The computer systems tracks the location of the gel throughout the assembly and controls the time and sequence of the various staining steps and controls the scanning and cutting steps.

The loading station receives a plurality of gel cassettes from a second dimension electrophoresis separation process. The electrophoresis gel cassette includes an identifying marker which correlates and catalogs the gel with a specific biological sample that was electrophoresed. A gel carrier, which is preferably a clamp, also includes an identifying marker. The markers are detected by the assembly to identify and associate a carrier with the particular gel. The gel is then separated from the cassette and transferred to the carrier. The carrier and the associated gel are then placed in a holding tank of the staining apparatus for processing at a later time.

The staining apparatus includes a computer operated robotic arm and a suitable reader for detecting the identifying marker on the gel carrier. The apparatus reads the identifying marker on the carrier to identify the gel slab and the biological sample. The computer is connected to a database to identify the gel slab and the biological sample, and then select a staining protocol for the gel that is appropriate for the particular biological sample. The robotic arm captures a carrier and the associated gel and transfers the gel between selected staining, rinse and holding tanks.

At the end of the staining process, the robotic arm transfers the gel to the gel cutting station for identifying stained gel spots in the gel and cutting the selected spots from the gel slab. The cutting station includes a computer controlled arm that is able to capture a tray for supporting the gel. The tray has a flat surface for supporting the gel clamp and the gel slab during scanning and cutting steps. The robotic arm of the staining apparatus suspends the gel and moves the gel and the carrier into contact with the tray to transfer the gel from the robotic arm to the tray. The computer controlled arm of the cutting station transfers the tray with the gel to a scanner. The scanner scans an image of the gel spots and compares the image with a library of the images of known biological samples. Selected sample spots are identified in the gel based on a comparison of the gel with an image of a known sample. After the image of the gel is obtained, the computer operated arm removes the tray from the scanner and transfers the tray to the cutting apparatus. The scanner is operatively connected to the cutting apparatus so that the cutting apparatus is able to cut selected spots from the gel and transfer the cut gel spots to a storage vessel such as a multi-well plate for further processing.

The computer controlled arm removes the tray from the cutting apparatus and moves the tray into position to enable the robotic arm to capture and remove the carrier and the gel from the tray. The computer controlled arm then moves the tray to a washing station where the tray is washed and dried for subsequent use. The robotic arm transfers the spent gel to a storage vessel or to a discard station where the carrier releases the gel into a suitable waste receptacle.

The various aspects of the invention are basically attained by providing an automated apparatus for processing an electrophoresis gel. The apparatus comprises a first recording assembly for receiving identifying information of a second dimension electrophoresis gel slab. A second recording assembly receives identifying information of a gel clamp capable of supporting and transporting the gel slab. A computer is coupled to the first recording assembly and the second recording assembly for cataloging a selected gel slab with a selected gel clamp.

The aspects of the invention are also attained by providing an automated apparatus for treating an electrophoresis gel slab. The apparatus comprises a plurality of liquid treating tanks having a dimension to receive an electrophoresis gel slab. A first robotic assembly transports electrophoresis gels between the liquid treating tanks. A second robotic assembly manipulates a support tray having a dimension to support the electrophoresis gel and transport the support tray between gel processing devices. A computer is operatively connected to the first robotic assembly and the second robotic assembly to coordinate movement of the first robotic arm assembly with respect to the liquid treating tanks and the second robotic arm assembly.

The aspects of the invention are further attained by providing a gel processing apparatus for processing a second dimension electrophoresis gel slab. The apparatus comprises a first gel slab processing device for processing the gel slab. A robotic arm assembly manipulates the gel slab and maneuvers the gel slab into a processing position of the gel processing device. An operating computer is operatively coupled to the robotic arm for controlling the robotic arm.

The objects, advantages and salient features of the invention will become apparent to one skilled in the art in view of the following detailed description of the invention in conjunction with the annexed drawings which form a part of this original disclosure.

BRIEF DESCRIPTION OF THE DRAWINGS

The following is a brief description of the drawings, in which:

FIG. 4 is an side view of the loading station of the embodiment of FIG. 2;

FIG. 5 is a partial side view of the loading assembly in the embodiment of FIG. 2;

FIG. 6 is a partial cross-sectional side view of the loading assembly showing the bar code reader;

FIG. 6A is a side view of an alternative arrangement of the proximity switch on the loading assembly;

FIG. 7 is a top view of the gel clamp in one embodiment of the invention;

FIG. 8 is a side view of the gel clamp of the embodiment of FIG. 7;

FIG. 9 is a perspective view of the tray for loading a gel into a gel clamp;

FIG. 10 is a cross-sectional side view of the tray of FIG. 9 showing the gel cassette and the gel clamp;

FIG. 11 is a partial cross-sectional side view showing the tray loading an electrophoresis gel into a gel clamp;

FIG. 12 is a perspective view of the staining assembly in one embodiment of the invention;

FIG. 13 is a front view of the robotic apparatus of the staining assembly of the embodiment of FIG. 12;

FIG. 14 is a partial side view showing the robotic assembly;

FIG. 15 is a partial side view showing the robotic assembly placing a gel clamp into a staining tank;

FIG. 16 is a partial side view showing the robotic assembly removing a gel and gel clamp from a staining tank;

FIG. 17 is a partial side view showing the actuating assembly of the robotic assembly with the operating arms in the retracted position;

FIG. 18 is a side view of the robotic assembly showing the operating arms in the extended position;

FIG. 19 is an end view showing the robotic arm in position for capturing a gel clamp;

FIG. 20 is an end view showing the robotic arm having captured a gel clamp;

FIG. 21 is a partial end view in cross-section showing the staining tank with the textured surface to prevent the gel from adhering to the surfaces of the gel tank;

FIG. 22 is a perspective view of the agitating assembly in one embodiment of the invention showing the divider coupled to the wall of the tank;

FIG. 23 is a partial end view in cross-section of the agitating assembly in the embodiment of FIG. 22;

FIG. 24 is a partial side view showing the agitating assembly with the rail in the lowered position;

FIG. 25 is a partial side view showing the agitating assembly with the rail in the raised position;

FIG. 28 is a top view of the apparatus for relieving stress in the gel while in a gel clamp;

FIG. 29 is a front view of the assembly for relieving stress in the gel in the embodiment of FIG. 28;

FIGS. 30A–30D show the sequential movement of the operating arms of the assembly for relieving stress in the gel;

FIG. 31 is an end view of the device for removing a gel from a gel clamp;

FIG. 32 is an end view of the device of FIG. 1 showing the gel being released from the gel clamp;

FIG. 33 is a front view of the scanning and cutting assembly in one embodiment of the invention;

FIG. 34 is a top view of the robotic arm of the assembly of FIG. 33;

FIG. 35 is a side view of the robotic arm of the assembly of FIG. 33;

FIG. 36 is a front view of robotic arm of the assembly of the embodiment of FIG. 33;

FIG. 37 is a rear view of the robotic arm showing the actuating mechanism;

FIG. 38 is a front view of the robotic arm showing the tray supporting the gel coupled to the robotic arm;

FIG. 39 is a top view of the tray for supporting a gel and gel clamp;

FIG. 40 is a partial cross-sectional end view showing the tray supporting a gel and gel clamp;

FIG. 41 is a side view of the robotic arm and tray in position for receiving an electrophoresis gel;

FIG. 42 is a side view of the robotic arm with the gel partially placed on the tray;

FIG. 43 is a side view of the robotic arm after the gel and gel clamp have been transferred to the tray;

FIG. 46 is a side view of the robotic arm in position for placing the tray and gel in a scanning device;

FIG. 47 is a side view showing the tray and gel inserted into a scanning device;

FIG. 50 is a top view the cutting device in one embodiment of the invention;

FIG. 51 is a side view in partial cross-section of the robotic arm positioned above a washing device for washing the tray;

FIG. 52 is a side view showing the robotic arm lowering the tray into the washing device;

FIG. 53 is a top view of the washing device showing a spray of water directed toward the tray;

FIG. 54 is a top view of the washing device showing a jet of air for drying the tray;

FIG. 56 is a cross-sectional view of the gel relaxer taken along line 56—56 of FIG. 55;

FIG. 57 is a side view of the gel relaxer of FIG. 55;

FIG. 58 is a partial side view of the gel relazer showing the mounting bracket for the roller in partial cross-section;

FIG. 63 is a top view of the gel relaxer showing the tray completely inserted into the gel relaxer;

FIG. 64 is a partial cross-sectional end view of the gel relaxer showing the cam member in the retracted position;

FIG. 65 is a partial cross-sectional side view of the gel relaxer showing the cam in the extended actuating position.

DETAILED DESCRIPTION OF THE INVENTION

The present invention is directed to an automated apparatus for transferring and manipulating a work piece between various work stations. In particular, the invention is directed to a computer controlled, automated assembly for manipulating and processing an electrophoresis gel between various work stations.

The invention is directed to a computer operated assembly 10 for staining, scanning and cutting samples from an electrophoresis gel slab. Typically, the gel slab is obtained from a second dimension electrophoresis separation process. The assembly 10 includes a computer to control the entire assembly and the handling and processing of the gel. As discussed hereinafter in greater detail, the assembly identifies a gel, selects a processing protocol for the gel, and tracks the location of the gel throughout the assembly.

Figure 1:
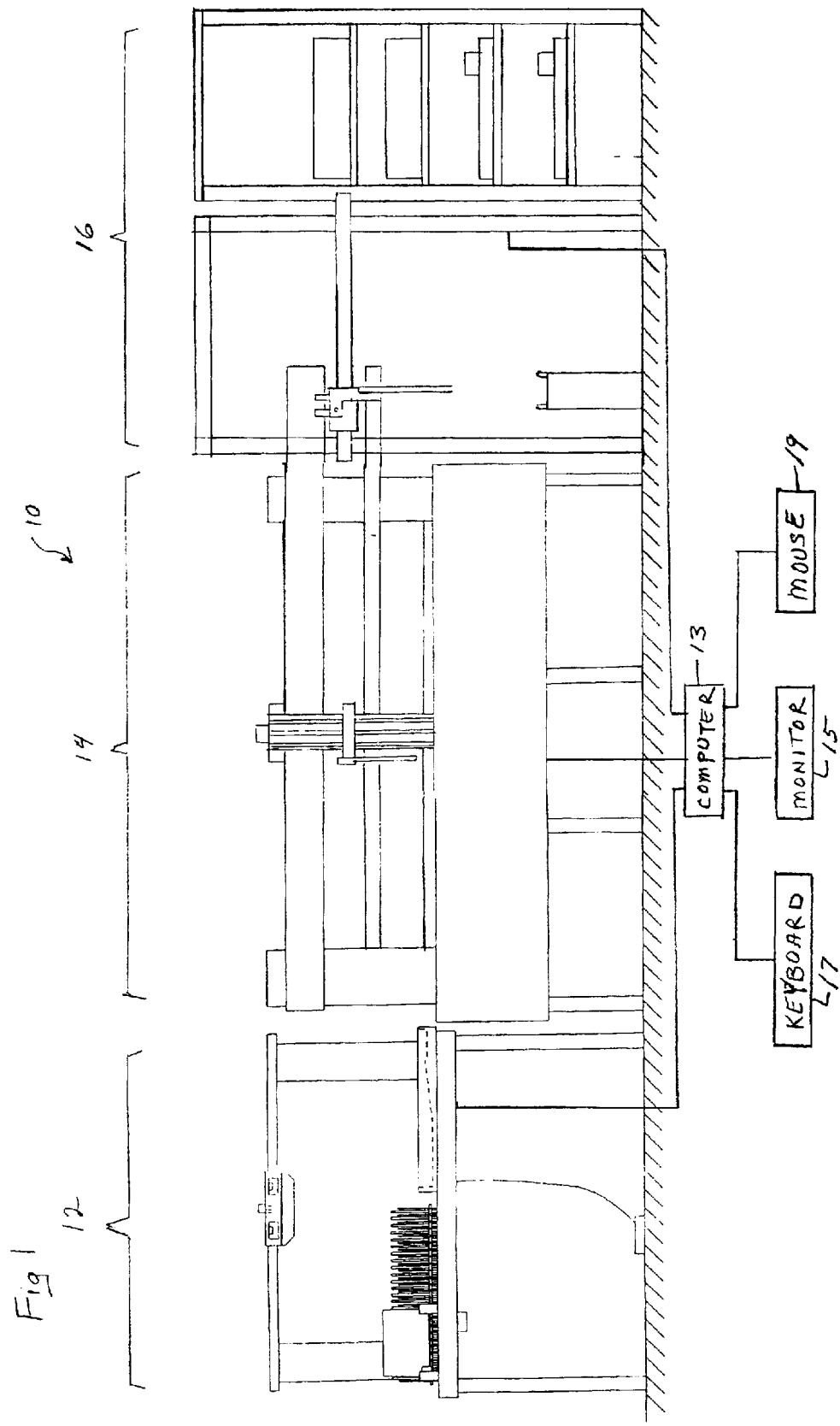
FIG. 1 is a front view of the assembly for processing electrophoresis gels.
Figure 2:
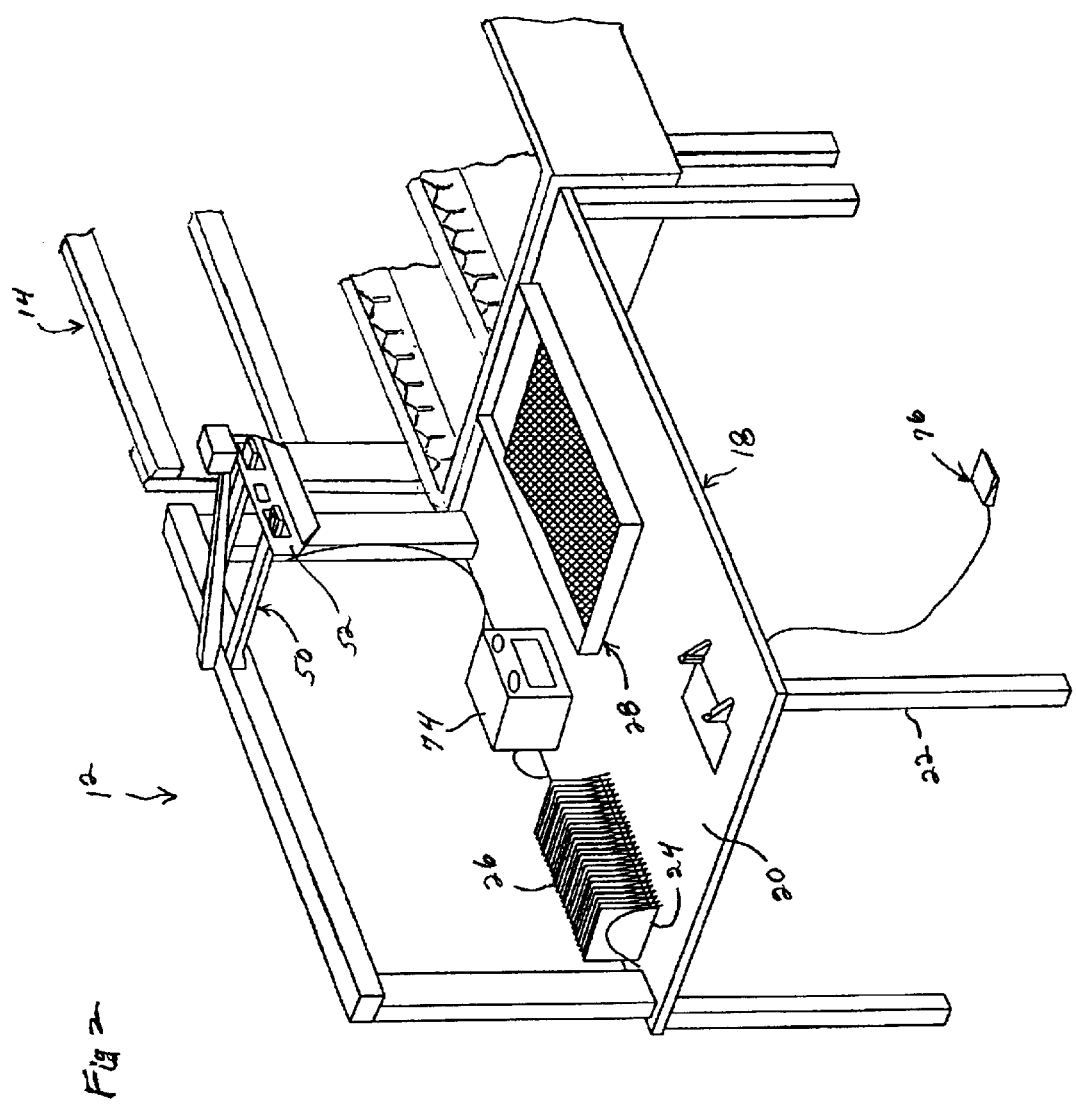
FIG. 2 is a perspective view of the loading station in one embodiment of the invention.

Referring to FIG. 1, the assembly 10 basically comprises a loading station including a loading assembly 12, a staining station including a staining assembly 14, and a cutting or excising station including a scanning and cutting assembly 16. The assembly 10 is a computer controlled robotic assembly for automatically manipulating the gels through the assembly with little or no manual handling of the gels. In preferred embodiments of the invention, the assembly 10 is able to operate continuously to process in sequence a large number of gels, and typically several hundred gels per day. The assembly is able to monitor continuously the location of a given gel throughout the assembly from the time the original gel slab enters the assembly to the time protein samples are excised from the gel and deposited in a multiwell plate. In this manner, a single technician can process a large number of gels without the need to handle each of the gels in the various processing stages. As discussed hereinafter in greater detail, assembly 10 includes a control system having a computer 13 with a display monitor (CRT) 15, a keyboard 17, and a mouse 19 or other user interface device. The computer, display monitor, keyboard and mouse are hardware components to enable operator interface for programming the assembly to perform selected sequences of processes, starting and stopping the process and entering process variables for performing specific functions.

Referring to FIGS. 2–11, loading assembly 12 includes a table 18 forming a work surface 20 for separating electrophoresis gels from the gel cassettes and loading the gels onto a carrier for supporting the gel and manipulating the gels through the various process steps. Table 18 includes a plurality of supporting legs 22 to support the work surface at a comfortable height for the technician. Work surface 20 has a dimension to support a rack 24 for supporting a plurality of electrophoresis gel cassettes 26 and a device 28 for separating the gel from the cassettes 26.

Figure 3:
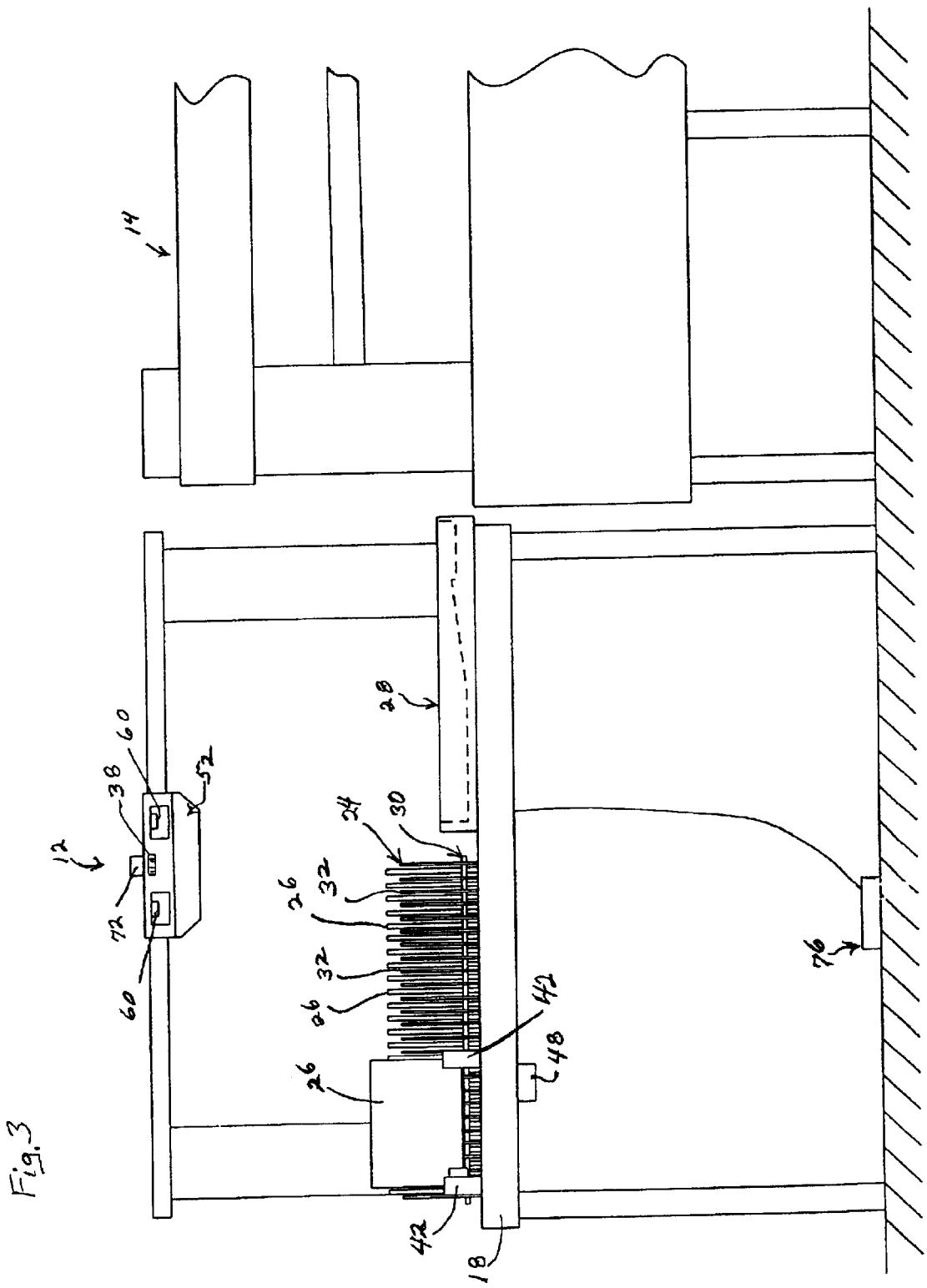
FIG. 3 is a front view of the loading station of FIG. 2.

Referring to FIG. 3, rack 24 includes a base 30 and a plurality of spaced apart supports 32 extending in a substantially vertical direction. Supports 32 are arranged to support cassettes 26 in an upright position as shown in FIG. 3. Cassettes 26 in preferred embodiments include two plates 34, typically glass, supporting an electrophoresis gel slab 36 therebetween as shown in FIGS. 10 and 11. The electrophoresis gel slab 36 is typically a standard second dimension electrophoresis gel, such as an acrylamide gel, that contains proteins or other macromolecules that have been separated by an electrophoresis separation process as known in the art. Each cassette includes an identifying marker 38 shown in FIG. 6 corresponding to a biological sample and for identifying a specific gel slab 36. The marker 38 in one preferred embodiment is a bar code that can be read by a suitable bar code reader. In another embodiment, marker 38 can be a computer chip or other machine readable device that is able to record information pertaining to the gel.

Referring to FIGS. 4 and 6, a detector assembly 40 is provided on work surface 20 to detect the presence of a gel cassette 26 and to read marker 38. In the illustrated embodiment, detector 40 includes two spaced-apart brackets 42 having a vertical slot 43 to receive a gel cassette 26 and support the cassette 26 in a vertical orientation. A proximity switch 44 is included in at least one of the brackets 42 to detect the presence and the proper orientation of a cassette 26 in brackets 42. A transparent window 46 is provided in work surface 20 adjacent brackets 42 as shown in FIG. 6. A detector 48 capable of detecting and reading marker 38 is coupled to a bottom side of work surface 20 next to window 46 and positioned in a location to enable detector 48 to read marker 38 on cassette 26. In the illustrated embodiment, detector 48 is a bar code reader that is positioned to read a bar code marker 38 on a cassette 26. In alternative embodiments, detector 48 can be positioned on the top of work surface 20 in a suitable location to read bar code marker 38. Proximity switch 44 can be located in other suitable locations to ensure that bar code marker 38 is properly aligned with detector 48 so that detector 48 accurately reads marker 38. Preferably, detector 48 is operable only when proximity switch 44 is activated by cassette 26 that is properly aligned with detector 48.

A support arm assembly 50 retains a plurality of gel clamps 52 that function as carriers for handling an electrophoresis gel slab 36 after it has been separated from the cassette 26. As discussed hereinafter in greater detail, gel clamps 52 include jaws 54 and 56 as shown in FIG. 7 where jaw 54 includes two apertures 58 to receive a support device. In a preferred embodiment, support arm assembly 50 includes two parallel arms 60 spaced apart a distance to be received in apertures 58 of clamps 52 so that clamps 52 are suspended in a stable position. Arms 60 have an outer end 62 with an upwardly extending lip 64 to prevent clamps 52 from inadvertently sliding off the end. A proximity switch 66 is included adjacent lip 64 on a top side of at least one of arms 60 to detect the presence of a clamp 52. In an alternative embodiment shown in FIG. 6A, a proximity switch 67 is mounted on arm 70 and is connected to a pivotally mounted arm 75.

As shown in FIG. 5, clamps 52 include an identification marker 68 such as a bar code. Support arm assembly 50 also includes an arm 70 supporting a detector or reader device such as a bar code reader 72 positioned in a location to read the bar code 68 on clamp 52. In the embodiment illustrated, bar code 68 is positioned along a top end of clamp 52 and bar code reader 72 is positioned above support arm assembly 50. Proximity switch 66 is positioned on arm 60 so that the clamp 52 is aligned with bar code 68 when proximity switch 66 is actuated to enable accurate reading of the bar code. In a preferred embodiment, proximity switch 66 is operatively connected to detector 72 so that detector 72 is only operable when proximity switch 66 is triggered by a gel clamp 52 that is properly aligned with detector 72.

In a preferred embodiment, a flexible curtain 73 is suspended from arm 70 and is aligned with the location of bar code 68 on clamp 52. Curtain 73 is a flexible plastic member that bends upwardly as shown in FIG. 5 when a clamp 52 is positioned against lip 64. Preferably, curtain 73 has a length and width to enable bar code reader 72 to view and capture an image of the bar code on the gel clamp positioned against lip 64 while blocking the view of the bar codes on the clamps behind the foremost clamp, thereby ensuring that bar code reader 72 reads only a single bar code at a time.

Detector 48, switch 44, bar code reader 68 and switch 66 are connected to a control unit 74 such as a microprocessor to control the operation of the assembly. An actuator device 76, such as a foot operated pedal, is connected to control unit 74. In a preferred embodiment, control unit 74 is operatively connected to a primary computer control system 13 for controlling assembly 10 as discussed hereinafter in greater detail.

In the operation of loading assembly 12, the technician selects a gel cassette 26 from rack 24 and places the cassette 26 into slots 42 of brackets 42. The cassette 26 is oriented with the marker 38 facing the detector 48 as shown in FIG. 5 so that proximity switch 44 is activated. A gel clamp 52 is moved into the position on arms 60 to actuate switch 66 and to be in position to enable reader 72 to read bar code 68 on clamp 52. When the cassette 26 and gel clamp 52 are in position and switches 44 and 66 are actuated, control unit 74 produces a visual or audio signal to the technician at which time the technician operates actuator 76 to actuate detector 48 and bar code reader 72. Preferably, detector 48 and bar code reader 72 cannot be actuated until switches 44 and 66 are actuated to ensure the accurate and simultaneous reading of the respective bar code on clamp 52 and cassette 26. The detector 48 reads the marker 38 while reader 72 reads bar code 68 so that control unit 74 associates a specific gel 36 with a gel clamp 52. Control unit 74 is able to transfer a signal to the operating computer to identify a particular gel and sample with a gel clamp.

Gel clamp 52 and the associated cassette 26 are then placed in tray 78 that contains a liquid, such as deionized water. The plates 34 of gel cassette 26 are separated and gel slab 36 is transferred to clamp 52. Clamp 52 and the captured gel slab 36 are then manually transferred to staining tank assembly 14.

Referring to FIGS. 9–11, device 28 is a tray 78 comprising a vessel to contain a liquid, gel slab 36 and clamp 52 for manipulating gel 36 from a cassette 26 to clamp 52. In the embodiment illustrated, tray 78 has a substantially rectangular configuration with a bottom wall 80, side walls 82 and end walls 84. Side walls 82 and end walls 84 extend in a substantially upward direction perpendicular to bottom wall 80 to define an internal cavity 86 with an open top. A retaining arm 88 is coupled to one end wall 84 to engage a gel clamp 52 as discussed hereinafter.

As shown in FIG. 9, bottom wall 80 has a top face 90 and a bottom face 92. Bottom face 92 is substantially planar and defines a horizontal dimension of tray 78. Bottom wall 80 includes a first end 94 having a first bottom section 96 and a second end 98 having a second bottom section 100. As shown in the embodiment of FIG. 9, a substantially inclined middle section 102 extends between first bottom section 96 and second bottom section 100. In alternative embodiments, tray 78 can have a substantially flat bottom extending between first end 94 and second end 98.

First bottom section 96 of bottom wall 80 forms a substantially planar surface and an area of tray 78 having a substantially uniform depth. Inclined middle section 102 is contiguous with first bottom section 96 to form an area of tray 78 having a decreasing depth from first end 94 toward second end 96. As shown in FIG. 9, inclined middle section 102 has a first end joining first bottom section 96 and a second end joining second bottom section 100. Second bottom section 100 defines a recessed portion 104 that is recessed with respect to inclined middle section 102. Recessed portion 104 has a substantially planar bottom surface extending between side walls 82.

In preferred embodiments of the invention, first bottom section 96 of inclined middle section 102 has a surface that resists an electrophoresis gel from adhering to bottom wall 80. In the embodiment illustrated, inclined section 102 also includes a top surface that resists adhering to an electrophoresis gel.

In one embodiment of the invention, the top surface of inclined middle section 102 and the top surface of first bottom section 96 have a surface that is able to support a liquid barrier layer between gel slab 36 and the surfaces of tray 78. In the illustrated embodiment, the surfaces include a plurality of fluid channels 108 formed by spaced-apart projections 110. Projections 110 are spaced-apart to form a plurality of rows and columns to form a substantially uniform array. Projections 110 in the illustrated embodiment have a substantially pyramid shape formed by outer faces 112 that converge to a peak 114. Projections 110 form channels 108 between adjacent peaks 114, which appear as a recess or trough. Projections 110 are dimensioned so that channels 108 contain an amount of the liquid to form a liquid barrier and to enable peaks 114 to support an electrophoresis gel slab in the liquid without damaging the gel slab 38 as discussed hereinafter in greater detail. Peaks 114 have a dimension to form a contact area for contacting the gel that is less than the surface area of top surface 92 of bottom wall 80. Projections 110 are spaced apart a distance and provide a surface area sufficient to support an electrophoresis gel without piercing or damaging the gel 36. The spacing between adjacent peaks preferably prevents the gel from contacting the bottom of channels 108. Channels 108 have a width and depth sufficient to contain a volume of liquid to flow between peaks 114 and prevent an electrophoresis gel from adhering to projections 110.

In the embodiment illustrated in FIGS. 9–11, projections 110 have substantially planar outer faces 112. In alternative embodiments, the projections can be formed with concave surfaces or convex surfaces resembling a bubbled surface. In further embodiments, the projections can be in the form of spaced-apart ridges forming valleys between adjacent peaks. The ridges can be oriented in a longitudinal direction, transverse direction or diagonal direction with respect to a longitudinal dimension of tray 78. In further embodiments, the surfaces of tray 78 can be formed with a series of recesses or channels that define distinct projections as in the illustrated embodiment.

In the illustrated embodiment of tray 78, projections 110 provide a surface that inhibits the gel slab from adhering to the bottom of tray 78. The electrophoresis gels as commonly used in the art are soft and pliable. Moreover, the gels generally have a tacky surface that tend to stick to many surfaces on contact. The pliable nature of the gels enable the gels to stick readily to smooth surfaces such as a glass plate or the smooth surface of a tray or tank. It has been found that forming the surface with a plurality of channels, recesses or apertures reduce the surface area that contacts the gel, and form a liquid barrier thereby inhibiting the gel from sticking and enabling the gel to slide on the surface without damaging the gel. In addition, the channels provide a system to prevent or release the suction between the gel and the surface of the tray that occurs when the gel is pulled away from the surface. The channels can be of any number of shapes and orientations that are able to release the suction or prevent the suction from forming. Preferably, the channels have a dimension and length to allow a fluid, such as distilled water, deionized water or a buffer solution to flow between the gel and the surface of tray 78 to release the suction effect and inhibit the gel from adhering to the surface.

As shown in FIGS. 10 and 11, first bottom section 96 has a dimension corresponding substantially to the dimension of an electrophoresis gel cassette 26. Cassette 26 is a standard second dimension electrophoresis cassette as known in the electrophoresis art. Cassette 26 includes supporting plate 34 spaced-apart a uniform distance by spacers (not shown). Plates 34 are typically glass plates, although other materials can be used. An electrophoresis gel 36 having a thickness of about 2–3 mm is provided between plates 34.

Referring to FIG. 10, recess 104 of second bottom section 100 is dimensioned to receive first clamping jaw 54. As shown in FIG. 10, recess 104 is recessed with respect to second bottom section 100 a distance corresponding substantially to the thickness of first clamping jaw 54. In this fashion, the clamping surface of first clamping jaw 54 is substantially coplanar with the surface of inclined section 102.

In a preferred embodiment, tray 78 is provided with retaining arm 88 for engaging the operating end of second clamping jaw 56 and retaining the clamping surfaces in an open position as shown in FIG. 10. Retaining arm 88 in one preferred embodiment of the invention is connected to an end wall 84 by a pivot pin 116. Pivot pin 116 is fixed to retaining arm 88 and extends into an aperture in a top surface 118 of end wall 84. A knob 120 is connected to a top end of pivot pin 116 for rotating retaining arm 88 from a retracted position to a retaining position shown in FIG. 10. Retaining arm 88 in the embodiment illustrated has a generally L-shape configuration with a substantially horizontal top leg 122 and a downwardly extending vertical leg 124. Vertical leg 124 has a dimension to engage the operating end of second clamping jaw 56 as shown in FIG. 10.

Tray 78 is used to transfer an electrophoresis gel slab 36 from cassette 26 to gel clamp 52. Typically, a liquid 126 such as deionized water, distilled water or a buffer solution is placed in tray 78 to a sufficient level to cover projections 1 10 and cassette 26 as shown in FIG. 10. Cassette 26 is placed in liquid 126 at first bottom section 96 of tray 78. The top plate 34 of cassette 26 is gently separated from gel 36 in a manner to avoid tearing or distorting gel 36. In one embodiment, cassette 26 is immersed in liquid 126 and the top plate 34 is separated from gel 36 while immersed in liquid 126. In alternative methods, the top plate can be separated from the gel prior to immersing in the liquid.

Gel clamp 52 is positioned in the recess 104 of tray 78 and second clamping jaw 56 is pivoted to the open position. Retaining arm 88 is then rotated to the retaining position to engage second clamping jaw 56 and retain clamp 52 in the open position as shown in FIG. 10 for receiving gel 36. Gel 36 is immersed in liquid 126 and is separated from the bottom plate of cassette 26. Gel 36 can then slide upwardly along inclined middle section 102 to position a longitudinal edge 128 between the clamping surfaces of jaws 54, 56 as shown in FIG. 11. Projections 110 provide a small surface area that contacts gel 36 to prevent gel 36 from adhering to bottom wall 80 of tray 78. Projections 110 form channels 108 between adjacent projections to supply the liquid 126 to the bottom surface of gel 36 so that gel 36 can float and slide along bottom wall 80. When gel 36 is positioned between clamping jaws 54 and 56, retaining arm 88 is pivoted to the retracted position to allow the clamping surfaces of the jaws to engage gel 36.

Gel clamp 52 serves as a carrier device capable of supporting and suspending an electrophoresis gel slab without damaging the gel. Electrophoresis gel 36 typically is a conventional gel used in two-dimensional electrophoresis separation as known in the art. The electrophoresis gels are made of an acrylamide material that are about 0.5–3 mm thick and can be difficult to handle. Typically the gels are about 1–1.5 mm thick. The gels are soft and pliable and can tear, stretch and stick to most surfaces that it contacts. Manual handling of the gels by conventional methods usually results in a large number of the gels being damaged. The gel slab is supported by gel clamp 52 to manipulate the gel through the various process steps with minimal damage to the gel.

Referring to FIG. 7, clamp 52 has a substantially longitudinal dimension having an operating end 130 and a gripping edge 131. Gripping edge 131 is a substantially straight edge and has a length corresponding substantially to the length of gel 36. First jaw 54 has a substantially planar configuration and is formed from a sheet material that is sufficiently rigid to support a gel slab. Typically, clamp 52 is made from a rigid plastic material that is non-reactive with the gel or the various solutions used to treat the gel. In alternative embodiments, clamp 52 can be made of metal or other non-reactive materials.

As shown in FIG. 7, operating end 130 of first jaw 54 has a length slightly greater than gripping edge 131. Openings 58 in first jaw 52 enable coupling to articulated arms of a robotic assembly as discussed hereinafter in greater detail. First jaw 54 has side edges that converge to gripping edge 131 and form a step portion or shoulder 132 along opposite sides to engage a support for suspending gel 36 in the liquid contained in staining assembly 14. In the embodiment illustrated, a rib 134 is coupled to a top face of first jaw 54 to define a fulcrum for the second jaw 56. Rib 134 is spaced from gripping edge 131 and extends substantially the length of first jaw 54 and parallel to gripping edge 131.

Second jaw 56 has a longitudinal dimension with a gripping edge 135 and an operating end 136 as shown in FIG. 8. Gripping edge 135 of second jaw 56 is a substantially straight edge complementing gripping edge 131 of first jaw 54 and has a length corresponding to the length of gripping edge 131 of first jaw 54. In the embodiment illustrated, second jaw 56 has a width less than the width of first jaw 54. In alternative embodiments, second jaw 56 can have a width substantially the same as or greater than the width of first jaw 54. Second jaw 56 is coupled to first jaw 54 and is pivotable about rib 134 to open and close the gripping edges of the jaws.

First jaw 54 and second jaw 56 have a longitudinal length to be able to grip and suspend gel 36 without tearing or stretching gel 36. It has been found that continuous griping surfaces of the clamp that extend a substantial portion of the edge of a gel slab can suspend the gel with little or no distortion or tearing. A uniform clamping pressure along the length of the gripping edges minimizes distortion and stretching of the gel.

First jaw 54 and second jaw 56 are biased by a suitable biasing device to apply a sufficient gripping pressure between gripping edges with sufficient force to support an electrophoresis gel slab. Preferably, the jaws are biased to apply a substantially uniform pressure along the length of the gripping surfaces.

In a preferred form of the invention, first jaw 54 and second jaw 56 include several magnets 137 positioned in apertures to bias the gripping edges together. As shown in the embodiment of FIG. 7, magnets 137 are spaced a slight distance from the gripping edges to provide the attracting force to the gripping edges to engage gel slab 36. Magnets 137 in the illustrated embodiment are cylindrical bar magnets made from a rare earth metal and are oriented so that opposite poles face each other to attract the jaws together with a uniform clamping force along the length of the jaws sufficient to support a gel without other mechanical coupling devices. In alternative embodiments of the invention, one or more magnets can be provided on one of the jaws with a metal strip on the other jaw to attract the magnet. A protective plastic film or tape can be applied over the apertures in the jaws to retain the magnets in place. In alternative embodiments, the magnets are flexible magnetic plastic strips as known in the art that are coupled to the jaws by a suitable adhesive.

In a preferred embodiment, gripping edges 131 and 135 of jaws 54 and 56, respectively, include an abrasive material 138, such as a fine grit sandpaper to assist in gripping gel 36. In preferred embodiments, abrasive member 138 has a length corresponding to the dimensions of clamp 52 and a width sufficient to grip gel 36 without damaging the gel. In one embodiment of the invention, a resilient member such as is a compressible foam made of a polymeric material is adhesively attached to gripping edges of the jaws to assist in applying a uniform clamping pressure along the length of the gel.

The dimensions of the clamp can vary depending on the dimensions of the gel and the robotic assembly. Preferably, the clamps have a gripping edge with a length sufficient to distribute the clamping force along the length of the gel to prevent the gel from tearing or distorting when suspended by the clamp. In further embodiments, the clamp can have spaced-apart gripping surfaces that are spaced along the length of the gel to provide the necessary clamping force. Preferably, the gripping surfaces of the clamps are dimensioned to form a continuous gripping surface along the length of the gel.

Referring to FIGS. 12–32, staining tank assembly 14 includes a computer controlled robotic assembly 140 constructed for manipulating electrophoresis gel 36 and clamp 52. In the embodiments illustrated, assembly 14 includes several tanks 142 containing various liquids and defining various work stations for treating and processing electrophoresis gel 36. Preferably, tanks 142 contain a sufficient amount of a liquid to immerse the gel. Immersing the gel in the liquid supports the gel to prevent sagging and tearing and prevents the gel from drying.

In the illustrated embodiments, robotic assembly 140 is constructed for selectively transferring a plurality of electrophoresis gels to sequential processing stages and particularly through a sequence of staining and developing steps using known reactants for electrophoresis gel staining. In one embodiment the staining tanks contain suitable fluorescent dyes and fixing agents. The automated assembly is operatively connected to the control system and is controlled by the computer or microprocessor. The control system monitors and operates the entire assembly and components of the assembly as discussed herein. The computer or microprocessor is operatively connected to the control system and the computer 13 to coordinate processing of the gels in assembly 10. A large number of gels and gel clamps can be placed manually in a row in one of the tanks. A suitable scanner is moved along the row to scan and read the bar codes on each of the gel clamps to take an inventory of the gels in the apparatus. The scanner feeds the identifying information from the bar code to the computer to record the information of the gels in the tank, record the location of the gels in the tank and select a staining protocol for the gels.

The various embodiments illustrated in the drawings generally show a single electrophoresis gel for purposes of convenience and clarity. In practice, the assembly is constructed to receive a large number of gels that are continuously carried through the processing tanks according to various processing protocols for the gels and are processed simultaneously or sequentially. The processed gels are ultimately transferred to a storage vessel or tank and then transferred to scanning and cutting assembly 16 for subsequent scanning identification, cutting and analysis of the proteins and other macromolecules in the gel.

Referring to FIGS. 12–15, robotic assembly 140 includes a main support frame 144 having a length extending substantially the entire length of apparatus 14. Frame 144 includes an upright vertical support member 146 at each end of assembly 14. A bottom rail 148, a middle rail 150 and top rail 152 extend between vertical supports 146. In the embodiment illustrated, rails 148, 150 and 152 are oriented substantially horizontal and extend from an upstream end adjacent loading assembly 12 to a downstream end adjacent cutting assembly 16.

Robotic arm assembly 140 includes a vertical rail 154 and a boom 156. Vertical rail 154 is oriented in a substantially perpendicular direction with respect to bottom rail 148 and extends between bottom rail 148 and top rail 152. Vertical rail 154 has a bottom end with a bracket that preferably supports guide wheels to ride along a top edge of bottom rail 148. A top end of vertical rail 154 also includes a bracket having guide wheels 159 to ride along a top side 161 of top rail 152. The brackets with the guide wheels effectively couple vertical rail 154 from frame 144 and are able to guide vertical rail 154 along the entire length of rails 148 and 152 between the end of frame 144. In one embodiment of the invention, top rail 152 and bottom rail 148 have a track to receive and guide the wheels along the respective rail.

Frame 144 includes a suitable drive assembly 158 for moving vertical rail 154 along the length of frame 144. Preferably, drive assembly 158 is operatively connected to a controller such as a computer or microprocessor for selectively controlling the movement and position of vertical rail 154 with respect to assembly 14 as discussed hereinafter in greater detail. In the embodiment illustrated, drive assembly 158 includes a motor 160 having a shaft with a drive gear 162. In this embodiment, motor 160 is mounted on middle rail 150 at an upstream end. A drive belt 164 extends between drive gear 162 and an idle gear 167 at the upstream end of middle rail 150. Drive belt 164 can be a continuous belt that is coupled to vertical rail 154. Motor 160 is actuated to operate drive belt 164 to move vertical rail 154 along the longitudinal length of frame 144 to a selected position. Preferably, motor 160 is a reversible motor that can be controlled to move vertical rail 154 in small increments. Generally, drive belt 164 has a plurality of teeth for engaging teeth on drive gear 162 to prevent drive belt 164 from slipping. Drive belt 164 is a flexible belt having sufficient strength with limited stretching to effectively move vertical rail 154 along frame 144 between each end. Other drive assemblies can be used that are capable of moving vertical with sufficient precision to align boom 156 in the desired location. In one embodiment a fixed belt is mounted on the frame and a gear driven by a drive motor on assembly 140 moves the assembly along the length of the frame.

Boom 156 includes a support housing 166 coupled to vertical rail 154. Vertical rail 154 includes an operating assembly 168 for raising and lowering boom 156 along the length of vertical rail 154. Referring to FIGS. 13 and 14, operating assembly 168 includes a drive motor 170 coupled to a rod 172 having external threads. A guide rod 174 is provided on each side of threaded rod 172 and extends substantially parallel to threaded rod 172. Support housing 166 of boom 156 includes a threaded aperture coupled to threaded rod 172 and a pair of axial passages for receiving guide rods 174 that extend parallel to threaded rod 172. Motor 170 is operated to rotate threaded rod 172 about its axis which causes housing 166 to move in a vertical direction along the length of threaded rod 172. Guide rods 174 are coupled to a top end and the bottom end of vertical rail 154 to stabilize and guide housing 166 along the length of vertical rail 154. Preferably, motor 170 is a reversible motor that can be controlled to raise and lower housing 166 and boom 156 to the desired position. Typically, threaded rod 172 and guide rods 174 extend the entire length of vertical rail 154.

In the embodiment illustrated in FIG. 14, boom 156 is substantially horizontal and extends outwardly from housing 166. In one embodiment, boom 156 is substantially perpendicular to frame 144. In alternative embodiments, boom 156 can be oriented at an angle with respect to frame 144 depending on the arrangement of the work stations and the construction of the overall assembly.

An articulated arm assembly 176 is coupled to boom 156 and includes a suitable drive assembly for selectively moving articulated arm 176 along the length of boom 156. Referring to FIG. 14, in one embodiment, boom 156 includes a support rail 178 and threaded drive rod 180 having one end coupled to housing 166. Articulated arm 176 includes a support housing 182 having an axial passage for receiving drive rod 180 and an axial passage for receiving support rail 178.

As shown in FIG. 14, a motor 184 is coupled to support rail 178 and threaded drive rod 180. Threaded drive rod 180 includes an outer end 186 received in a bearing 188 that is coupled to support rail 178 for supporting the outer end of rod 180. Support housing 182 includes an axial passage having internal threads complementing the external threads on threaded drive rod 180. Motor 184 is actuated to rotate threaded drive rod 180 for moving support housing 182 and articulated arm 176 along the length of support rail 178 of boom 156. In a preferred embodiment, motor 184 is an electric reversible motor operatively connected to a control circuit for selectively controlling the movement of articulated arm 176 in each direction along the longitudinal length of support rail 178. Motor 184 is operatively connected to the operating computer.

As shown in FIG. 14, articulated arm 176 includes a main body 190 that is coupled to support housing 182 and positioned below support rail 178 and threaded drive rod 180. Body 190 has a longitudinal dimension oriented substantially parallel to support rail 178 in the embodiment shown. Two movable coupling arms 192 are pivotally connected to each end of body 190. Coupling arms 192 have a top end coupled to body 190 by a pivot pin 194. Coupling arms 192 have a bottom end 196 opposite the top end and include a coupling pin 198.

As shown in FIGS. 17 and 18, an actuator 200 is coupled to body 190 for actuating coupling arms 192. Actuator 200 is provided with connecting rods 202 coupled to each coupling arm 192 for pivoting coupling arms 192 inwardly and outwardly with respect to main body 190 from a retracted position shown in FIG. 17 to an extended position shown in FIG. 18. Actuator 200 in one embodiment of the invention is a pneumatically operated piston assembly that is capable of moving connecting rods 202 simultaneously between a retracted position and an extended position for moving coupling arms 192. As shown in FIG. 17, air pressure lines 203 extend from a pressure source 205 shown in FIG. 16 to actuator 200. Preferably, the pressure source is computer actuated to automatically control the arms 192 and to coordinate with the movement with boom 156. In alternative embodiments, actuator 200 can be a solenoid operated device, electric motor or other device capable of actuating rods 202.

Referring to FIGS. 12–16, robotic assembly 140 is able to move and manipulate a work piece in three dimensions or coordinates with respect to tanks 142. Vertical rail 154 can be actuated to move along frame 144 oriented in a longitudinal dimension of apparatus 14. Boom 156 moves in a substantially vertical direction with respect to vertical rail 154 and assembly 140. Articulated arm 176 moves in a transverse direction with respect to apparatus 14 along the length of boom 156. In this manner, articulated arm 176 can maneuver a work piece between various work stations at essentially any location of apparatus 14.

Apparatus 14 of the invention is particularly adapted for manipulating and staining an electrophoresis gel that is obtained from a two-dimensional electrophoresis separation process as known in the art. Referring to FIG. 12, tanks 142 are dimensioned to contain a liquid such as deionized water, distilled water or a buffer solution and a plurality of electrophoresis gel slabs. As shown in FIG. 16, tanks 142 are formed with longitudinal sides 204 and a movable frame 206 having a plurality of spaced-apart notches 208. An electrophoresis gel slab 36 is supported by a gel clamp 52 having a length to fit within notches 208 of frame 206 so that gel 36 is suspended in the liquid contained in tank 142. In an alternative embodiment, the top edge of side walls 204 of tank 142 can include notches to receive the gel clamp 52. Typically, the notches have a generally V-shaped upper end and slot at the lower end to support the gel clamps.

Robotic assembly 140 is operated to sequentially transfer gels 36 from tanks 142 to a staining station 210 as shown in FIG. 12. Referring to FIG. 15, clamp 52 is suspended in recesses 208 of frame 206. Articulated arm 176 is lowered into the position shown to align coupling pins 198 of arms 192 with the openings 52 in the jaw of clamp 52. Boom 156 is then moved toward clamp 52 as shown in FIGS. 19 and 20 to insert coupling pins 198 through opening 58 in clamp 52. In this position, coupling arms 192 are in a retracted position so that coupling pins 198 can be inserted through openings in clamp 52. Arms 192 are then pivoted outwardly to capture clamp 52. Articulated arm 176 can then be raised to transport clamp 52 to the desired location.

Referring to FIGS. 19 and 20, coupling pins 198 have a shaft 212 and a retaining head 214. Head 214 is dimensioned to pass through the openings 58 in gel clamp 52 and is dimensioned to retain gel clamp 52 on shaft 212 while being maneuvered through the apparatus. Articulated arm 176 is maneuvered to insert coupling pins 198 through the openings of gel clamp 52 and coupling arms 192 are pivoted outwardly to a coupling position shown in FIG. 18 for coupling to gel clamp 52. Robotic assembly 140 is then actuated to remove gel 36 and clamp 52 from tank 142 and transfer gel 36 to staining station 210. Once the clamp 52 is placed in the desired position, the arms 192 are retracted and pins 198 are removed from clamp 52.

Articulated arm 176 includes a detecting device such as bar code reader 215 to read the bar code on clamp 52 as shown in FIG. 19. Reader 215 is connected to the operating system computer to read bar code 68 on clamp 52 to identify and monitor the location of gel clamp 52 throughout the staining process. Preferably, reader 215 is positioned on an articulated arm 176 to capture an image and read bar code reader 68 as clamp 52 is being captured by articulated arm 176. The operating computer is then able to identify the gel and select an appropriate staining protocol. Reader 215 is also used to scan the collection of he gel clamps in the apparatus to provide an inventory of the gels. The operating computer is able to monitor the location of the gel to be able to retrieve a specific gel when desired. Preferably, the reader is required to read the bar code on the clamp only one time. Once the bar code is read to identify a gel and gel clamp, the computer records the location of the clamp within the apparatus.

Assembly 14 includes a suitable computer for providing complete automation of robotic assembly 140. The computer is coupled to the drive motors to control the operation of each component and coordinate the movement of the assembly. The computer is able to control the operation of each of the motors individually so that the gels can be moved to selected locations. The computer coordinates the movement of the robotic arm and the actuation of the coupling arms to enable the assembly to capture a gel from one location and transfer the gel to another location.

Staining station 210 preferably includes a plurality of adjacent staining tanks 216 as shown in FIG. 12. Each of the staining tanks 216 is dimensioned to contain a suitable staining reagent and an electrophoresis gel. Staining tanks 216 are oriented in a transverse direction with respect to the longitudinal dimension of assembly 14. The various reagents are standard staining reagents as known in the art, such as stains, developing reagents, fixing reagents and rinsing solutions. Typically, staining tanks 216 contain the various reagents arranged in the sequence of use. Robotic assembly 140 is provided to sequentially transfer gel 36 to each staining tank 216 for sufficient time to treat the gel. After a predetermined treatment time, robotic assembly 140 removes gel 36 from one staining tank and transfers gel 36 to the next staining tank for the next treatment step according to a staining protocol selected for the gel. The staining reagents and/or the gels are typically agitated continuously to mix the reagents for promoting uniform staining of the gels. The gels can be moved in an up and down direction to provide a continuous agitation of the reagent. Alternatively, a pump can be provided to circulate the reagents.

In the embodiment shown in FIGS. 12 and 21, staining tanks 216 are assembled as a unit to form longitudinal side walls 218 and end walls 220. In a preferred embodiment, a rinse tank 222 containing a rinse water (not shown) is provided at the downstream end of staining station 210. Robotic assembly 140 is programmed to transfer gels 36 at the end of each step of the staining process from a respective staining tank 216 to rinse tank 222 for a time sufficient to rinse the reagents from the gel. In embodiments of the invention, robotic assembly 140 is programmed to transfer gel 36 to rinse tank 222 between each processing step to rinse the reagents from gel 36 before transferring to the next reagent to minimize contamination of the subsequent reagents by the residue of the previous reagent on the gel.

Staining tanks 216 are dimensioned to contain a reagent and an electrophoresis gel slab by suspending the gel slab in the reagent. As shown in FIG. 21, staining tanks 216 have side walls 224, end walls 226, and a bottom wall 228. Side walls 224 in the embodiment illustrated are substantially vertical and parallel to each other and define a depth sufficient to completely immerse gel 36 in liquid staining reagent 225 without gel 36 contacting bottom wall 228. Side walls 224 include a top end 230 that is angled outwardly from the center of staining tank 216 to form inclined surfaces 232. Inclined surfaces 232 open outwardly to form a guide surface for directing a gel into a respective staining tank 216 as the gel is lowered by robotic assembly 140.

As shown in FIG. 21, gel 36 is coupled to gel clamp 52 and suspended by frame 206 in a respective staining tank 216. To prevent gel 36 from adhering to side walls 224, side walls 224 are provided with a textured surface to limit the surface area of side walls 224 that contact gel 36. In a preferred embodiment of the invention, side walls 224 are formed with a plurality of projections 234 extending outwardly from side wall 224. Typically, projections 234 are arranged in a substantially uniform array of rows and columns in a manner similar to the projections of tray 78 shown in FIG. 9.

Projections 234 in one embodiment of the invention have a substantially rounded shape that form narrow channels between adjacent projections 234. The channels have a depth and a width to allow liquid to flow through the channels between the projections when gel 36 contacts side wall 224. Preferably, the channels have a dimension to allow a sufficient volume of liquid to flow between gel 36 and side wall 224 and to release the suction effect produced when gel 36 is pulled away from side wall 224, thereby releasing gel 36 and reducing the risk of stretching or damaging gel 36.

Preferably, projections 234 have a substantially uniform shape and dimension. In alternative embodiments, the projections can be staggered in rows and columns and have different lengths or widths. The projections typically have a rounded convex surface having a generally dome or bubble shape. In another embodiment, the projections can have a flat top surface separated by V-shaped recesses. In still further embodiments, the projections can be substantially parallel ridges having channels between adjacent ridges that can be oriented vertically or horizontally on side walls 224.

Frame 206 forms an agitating assembly to continuously move gels 36 within the holding tanks 142 and staining tanks 216. Referring to FIGS. 22 and 23, frame 206 includes support rails 236 positioned above a top edge of the side walls of holding tanks 142 and staining tanks 216 and extend in a longitudinal direction of assembly 14. Support rails 236 have a top face 238, an inner face 240 and an outer face. A plurality of spaced apart notches 208 are formed in inner face 240 and extend to top face 238. Notches 208 have a beveled top surface 244 converging toward a slot 246 at bottom end of notches 242. As shown in FIG. 12, support rails 236 are positioned on opposite sides of staining tanks 216 and holding tanks 142 with notches aligned with each other. Notches 208 are dimensioned to receive and guide a gel clamp 52 supporting a gel 36 into the respective slot 246 for suspending gel 36 in a liquid in the respective tank as shown in FIG. 23.

In one embodiment of the invention shown in FIGS. 22 and 23, holding tanks 142 include a plurality of recesses 248 in side walls 250 of holding tanks 142. Recesses 248 are spaced between notches 208 of rail 236 and adjacent the top edge of side wall 250. A divider 252 is inserted into recesses 248 to form chambers 254 as shown in FIG. 23 to prevent adjacent gels 36 from contacting each other. As shown in FIG. 22, divider 252 has a substantially rectangular shape to conform to the inner shape and dimensions of tank 142 and with outwardly extending coupling tabs 256. In the embodiment illustrated, divider 252 is formed from two flexible panels 258. Preferably, panels 258 are sufficiently flexible to be able to bend so that coupling tabs 256 can be inserted or removed from recesses 248. Each panel 258 preferably has a textured surface on the outer face to prevent the gel from adhering to the surface of divider 252 in a manner similar to the surface of tank 216 shown in FIG. 21.

Support rails 236 of frame 206 are mounted for continuous reciprocating movement in a vertical direction to move gel 36 within the treating liquid, thereby continuously agitating the liquid in staining tanks 216 and holding tanks 142. In this embodiment, support rails 236 continuously reciprocate in a vertical direction, although in alternative embodiments, support rails 236 can oscillate in a horizontal direction to continuously agitate the reagent. Continuous agitation of the gels and the reagent in staining tanks 216 provide for a more uniform distribution of the liquid and substantially uniform temperature throughout the surfaces of gel 36 during the staining steps.

Referring to FIGS. 24 and 25, each support rail 236 is coupled to a forward and trailing L-shaped actuating lever 260. Each lever 260 includes a body portion 262 having a top leg 264 extending substantially perpendicular to body 262. Leg 264 has an outer end 266 having a pivot pin 268 coupled to rails 236. A top end of body 262 is pivotally coupled by a pivot pin 270 to a fixed support 272 on the respective tank.

Actuating levers 260 are coupled to the respective support rail 236 on each side of the tank and are connected together by a connecting rod 274 extending between the body portion 262 of each actuating lever 260. In this manner, the pivoting levers are connected together to move in unison so that each support rail 236 reciprocates simultaneously. At least one of the levers 260 is connected to a drive motor 276. Drive motor 276 is mounted to a fixed support 278 and includes an eccentrically mounted crank 280. A connecting arm 282 has one end pivotally connected to crank 280 and an opposite end pivotally connected to a lever 260 on each side of the respective tank. As shown in FIGS. 24 and 25, motor 276 is actuated to rotate crank 280 to produce a pivoting movement of levers 260 about the respective pivot points 270. The pivotal movement of levers 260 result in a reciprocating motion of support rails 236 in a substantially vertical direction. Motor 276 is connected to a suitable power source and can be controlled by a microprocessor or the operating computer to control the timing, speed of motor 276 and the desired sequencing of the agitation of the respective gel and reagent.

Figure 26:
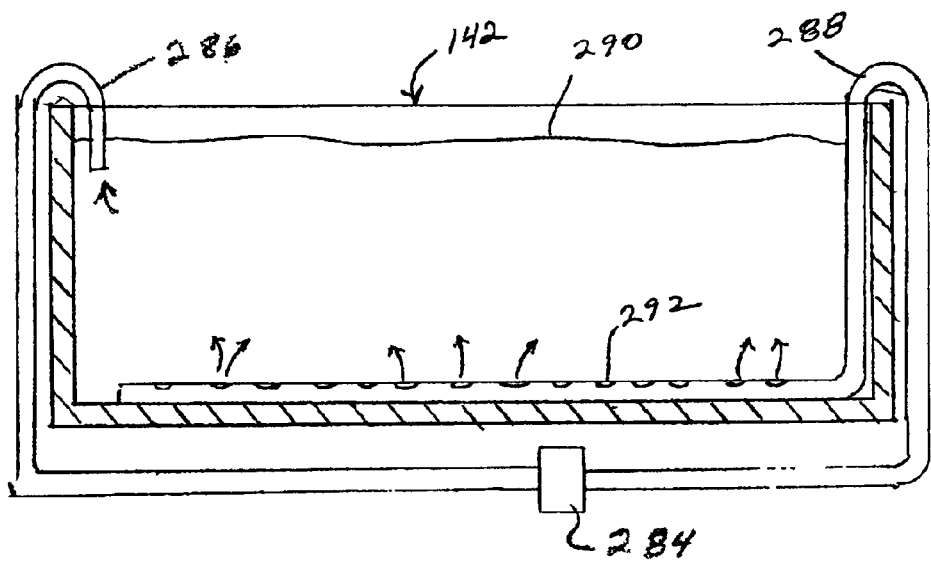
FIG. 26 is a partial cross-sectional side view showing the circulation assembly for the staining tank.
Figure 27:
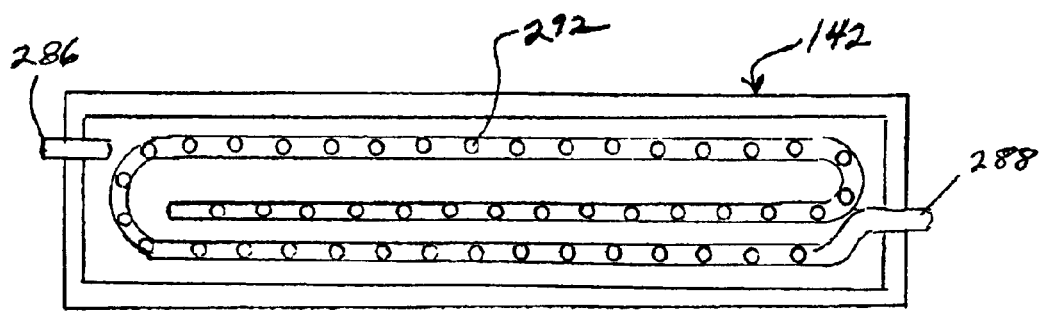
FIG. 27 is a top view of the circulation assembly of FIG. 26 for the staining tank.

In another embodiment, a liquid circulation system can be included in the tanks 142 and in each of the staining tanks 216 to provide a uniform distribution and temperature of the liquid. In this embodiment as shown in FIGS. 26 and 27, a liquid treating tank, such as holding tank 142, includes a pump 284 having an intake connected to an intake tube 286 and an outlet connected to an outlet tube 288. Intake tube 286 has an end positioned below the surface of liquid 290 in tank 142 to withdraw liquid 290 from the tank. The outlet tube 288 extends along the bottom of tank 142 in a circular pattern as shown in FIG. 27. Preferably, outlet tube 288 includes a plurality of outlet openings 292 along the length of the portion submerged in the liquid 290. Pump 284 continuously withdraws liquid 290 from an upper level and recirculates the liquid along the bottom to provide a uniform distribution of the reagents and to provide a uniform temperature throughout the liquid. In one embodiment, the liquid can be passed through a suitable heating or cooling device to adjust and monitor the temperature of the treating liquid as needed.

In embodiments of the invention, a robotic assembly 140 is programmed to select a gel from a staining tank 216, transfer the gel to rinse tank 220 for a predetermined period of time, and then transfer the gel to a developing tank where an image of the gel can be captured at different stages of the developing step. After one or more images of the gel are captured, robotic assembly 140 returns the gel to the staining tank 216 for further processing. The gel is again transferred to the developing tank after further processing to obtain a sequence of images for the gel during the staining process. Robotic assembly 140 is capable of sequentially transferring several gels between the various tanks for capturing sequential images of several gels. The computer control system of robotic assembly 140 maintains a record of the location of each gel being processed, the stage of the process for each gel and coordinates a captured image with the particular gel.

During the processing of the electrophoresis gels in the various treating liquids, the gels can shrink or expand slightly in one or more dimensions, which can result in some distortion of the gel with respect to the clamp. In some embodiments of the invention, robotic assembly 140 transfers the gels 36 and the clamps 52 to an apparatus 300 that is able to open the clamping jaws, allow the gels to relax and close the clamping jaws on the relaxed gels. By opening the clamping jaws, the stresses formed in the gel between the clamping surfaces can be relieved.

In one embodiment of the invention, apparatus 300 is used in conjunction with holding tanks 142 and staining tanks 216 that contain a treating liquid. In this embodiment, apparatus 300 is coupled to side rails 236 of frame 206. Alternatively, apparatus 300 can be coupled directly to the top edge of the side walls of a tank.

Referring to FIGS. 28 and 29, apparatus 300 includes a first operating arm 302 and a second operating arm 304 that are parallel and spaced apart a distance to receive gel clamp 52 and gel 36 therebetween. First arm 302 has a top end 306 connected to a support rod 308. Support rod 308 has outer ends 310 that are pivotally connected to a first end member 312 and a second end member 314. Second arm 304 has a top end 316 connected to a support rod 318 having outer ends 320. Outer ends 320 of support rod 318 are pivotally connected to first end member 312 and second end member 314.

First end member 312 is substantially parallel to second end member 314. First arm 302 is substantially parallel to second arm 304 to form a substantially rectangular shaped structure. Referring to FIGS. 28 and 29, first end member 312 has a plate 322 having spaced apart apertures 324 and 326 to receive end 310 of support rod 302 and end 320 of support rod 318, respectively. A coupling member 328 is provided at each longitudinal end of first end member 312 for coupling first end member 312 to a respective side rail 336 of frame 144. Second end member 314 is substantially a mirror image of first end member 312 and includes a plate 330 having spaced apart apertures 332 and 334 and a coupling member 336 at its longitudinal ends. Apertures 332 and 334 receive the end 310 of support rod 308 and the end 320 of support rod 318, respectively, for allowing pivotal movement of first arm 302 and second arm 304 with respect to end members 312 and 314.

Referring to FIGS. 30A–30B, support rod 308 of first operating arm 302 includes an upwardly extending connecting arm 336 adjacent first end member 312. Connecting arm 336 has a top end 338 with an aperture 340 for receiving a connecting pin 342. As shown in FIG. 30A, connecting arm 336 is oriented substantially parallel to the plane of first arm 302. Support rod 318 of second operating arm 304 includes a connecting arm 344 extending in an upward direction. Connecting arm 344 includes a top end 346 having an aperture 348 for receiving a pin 350.

An actuator 352 is coupled to connecting arm 336 and connecting arm 344 to pivot first arm 302 and second arm 304. In the embodiment illustrated, actuator 352 includes a pneumatic cylinder 354 having a reciprocating piston connected to a rod 356. Pneumatic cylinder 354 is pivotally connected to connecting arm 344 by pin 350. Rod 356 has an outer end 358 connected to connecting arm 336 by pin 342. Pneumatic cylinder 354 is connected to a pressure source by lines 360 to reciprocate rod 356 with respect to cylinder 354 to pivot connecting arms 336 and 344 for pivoting first arm 302 and second arm 304. Pressure lines 360 are coupled to a suitable pressure source such as a pump 362. A microprocessor or a computer 364 controls and actuates pump 362 in selected sequences to operate assembly 300. Computer 364 is connected to a main computer which controls a robotic assembly 140 to coordinate the movement of robotic arm 176 and the location of the gel clamp and its associated gel. In alternative embodiments, actuator 352 can be a hydraulically operated, solenoid operated or electrically operated device or other suitable device for actuating the apparatus.

As shown in FIGS. 30A–30B, apparatus 300 is positioned on top of rails 236, and gel clamp 52 is positioned between first arm 302 and second arm 304 so that gel 36 is suspended in the treating liquid. The treating liquid can cause gel 36 to exhibit some shrinking or expansion, which can cause gel 36 to distort and twist when gel clamp 52 does not allow gel 36 to move. In this embodiment of the invention, pneumatic cylinder 354 is actuated to pivot first arm 302 and second arm 304 apart from each other so that gel clamp 52 can be lowered by robotic arm 176 into position on rails 236 and supported in the slots between arms 302 and 304 as shown in FIG. 30A. Pneumatic cylinder 354 is then actuated to pivot first arm 302 and second arm 304 toward each other so that the arms grip gel 36 below gel clamp 52 as shown in FIG. 30B and engage gel clamp 52 to open the clamping jaws and allow gel 36 to expand or contract to its normal position as shown in FIG. 30C. First arm 302 and second arm 304 are then pivoted outwardly to release gel 36 and gel clamp 52 so that gel clamp 52 again closes on gel 36 as shown in FIG. 30D.

Referring to FIG. 30A, first end member 312 includes stop members 366 on each side of connecting arm 344 to limit the pivotal movement of connecting arm 344. Preferably, stop members 366 are oriented to limit the pivotal movement of second arm 304 to a substantially vertical orientation when pivoted inwardly toward first arm 302.

First clamping arm 302 has a lower end 368 opposite top end 306. A rocker arm 370 is connected to lower end 368 of first arm 302 in a manner to allow limited pivotal movement of rocker arm 370 with respect to first arm 302. Rocker arm 370 has a longitudinal length substantially equal to the length of first arm 302 with a bottom edge 372 and a top edge 374. Rocker arm 370 is pivotally connected to lower end 368 of first arm 302 by screws 376 or other suitable fastening members. Screws 376 extend through a respective aperture 378 in rocker arm 370 that are spaced from top edge 374. Screws 376 are threaded into complementing apertures 380 in first arm 302. Preferably, apertures have a diameter slightly greater than the diameter of screws 376 to provide limited pivotal movement of rocker arm 368 with respect to first arm 302.

Bottom edge 372 of rocker arm 370 defines a gripping surface 382 for gripping gel 36. Preferably, a rib 384 extends along bottom edge 372 and extends outwardly from the plane of rocker arm 370. Rib 384 can be integrally formed with rocker arm 370 or a separate element coupled to rocker arm 370 by an adhesive or mechanical fastener. Top edge 374 of rocker arm 370 defines an actuating surface for engaging gel clamp 52. In one preferred embodiment, a rib 386 extends along top edge 374 of rocker arm 370 to define actuating surface 388.

In preferred embodiments, rib 384 and rib 386 extend the length of rocker arm 370. Rib 384 has a width sufficient to grip and support the gel 36. Typically, rib 384 extends outwardly from the face of rocker arm 370 a distance to enable rib 384 to grip gel 36 without rocker arm 370 interfering with gel clamp 52.

Second arm 304 in the embodiment illustrated has an actuating member 390 having a substantially planar configuration. Actuating member 390 has a bottom end 392 and a top end 394. Bottom end 392 defines a gripping surface 396 for gripping gel 36. In a preferred embodiment, bottom end 392 of actuating member 390 includes a rib 398 defining gripping surface 396. As shown in FIGS. 30A–30D, rib 398 is aligned with rib 384 of rocker arm 370 for gripping opposite sides of gel 36. Preferably, rib 398 extends outwardly from the face of actuating member 390 a distance at least equal to the thickness of the clamping jaw of gel clamp 52 to enable rib 398 to grip gel 36 without interference from gel clamp 52. Actuating member 390 can be coupled to second arm 304 by screws or other fasteners. Alternatively, actuating member 390 and second arm 304 can be integrally formed as a one-piece unit. In one embodiment of the invention, gripping surfaces 382 and 398 include a textured surface, such as a fine grit sandpaper to provide a slip resistant surface.

In the illustrated embodiments, first arm 302 and arm 304 are mounted to pivot about a fixed pivot point. In other embodiments the arms are mounted to move in a substantially linear direction rather that in a pivotal motion. The actuating members and the operating arms are coupled to the support to reciprocate first arm 302 and second arm 304 toward each other in a linear motion.

Referring FIGS. 30A–30D, the method of the invention for relieving tension in gel 36 is depicted. As shown in FIG. 30A, pneumatic cylinder 354 is actuated to pivot first arm 302 and second arm 304 outwardly so that gel 36 and gel clamp 52 can be lowered into position between first arm 302 and second arm 304. Pneumatic cylinder 354 is then actuated to pivot first arm 302 and second arm 304 toward each other so that the respective gripping surfaces contact opposite sides of gel 36 with sufficient pressure to grip gel 36. As shown in FIG. 30B, second arm 304 is in a substantially vertical orientation with connecting arm 344 engaging stop member 366. Further actuation of pneumatic cylinder 354 continues to pivot first arm 302 toward second arm 304 into engagement with gel clamp 52 in the position shown in FIG. 30C.

The pivotal movement of first arm 302 enables rocker arm 370 to pivot with respect to first arm 302 so that actuating surface 388 engages a top end of the clamping jaw to pivot the clamping jaw about its fulcrum, thereby separating the gripping surfaces of gel clamp 52 from gel 36. In this position, gripping surface 382 of first arm 304 and gripping surface 396 of second arm 304 hold gel 36 in position until the clamping jaws of gel clamp 52 are again closed to grip gel 36. As shown in FIG. 30C, rib 386 extends from rocker arm 370 a distance sufficient to allow limited pivotal movement of the clamping jaw of gel clamp 52, thereby allowing gel clamp 52 to open. The method steps can be repeated several times as necessary to relieve stresses with respect to gel clamp 52 that is caused by contraction or expansion of gel 36. As shown in FIG. 30D, pneumatic cylinder 354 is again actuated to separate first arm 302 and second arm 304 to enable gel clamp 52 and gel 36 to be removed from assembly 300.

FIGS. 31 and 32 show another embodiment of the invention where an actuating assembly 402 is constructed to open the clamping jaws of gel clamp 52 to separate gel 36 completely from gel clamp 52 after processing gel 36. Assembly 402 is typically used only when the gel is to be discarded at the end of the process. In one embodiment shown in FIG. 13, assembly 402 is provided at the upstream end of robotic assembly 140.

Referring to FIG. 31, assembly 402 includes opposite end members 404 having a recess 406 for receiving gel clamp 52. A first arm 408 is pivotally connected to end members 404 by a pin 410. A second arm 412 is also pivotally connected to end members 404 by a pin 414. First arm 408 has a top end 416 and a lower end 418. Lower end 418 defines an actuating surface 420 for actuating gel clamp 52. In the embodiment illustrated, lower end 418 of first arm 408 includes a flat surface defining actuating surface 420.

Second arm 412 includes a top end 424 and a lower end 426 that opposes first arm 408. Lower end 426 defines an actuating surface 428. As shown in FIG. 31, lower end 424 of second arm 418 includes a rib 430 defining actuating surface 428. Top end 416 of first arm 408 and top end 424 of second arm 412 are operatively coupled to an actuator 432. Actuator 432 in this embodiment is a pneumatic cylinder 434 connected to second arm 412. Pneumatic cylinder 434 includes a reciprocating piston rod 436 connected to first arm 408.

Actuating surface 420 of first arm 408 and actuating surface 428 of second arm 412 are oriented to engage the clamping jaws of gel clamp 52. Actuator 432 is operated to pivot first arm 408 and second arm 412 so that the respective actuating surfaces engage gel clamp 52 with sufficient force to open the clamping jaws allowing gel 36 to fall from gel clamp 52 to a suitable waste receptacle 438. Gel clamp 52 can then be reused with a new gel for processing.

After the gels 36 are stained in the various staining tanks 216, robotic assembly 140 transfers the gels to one of the holding tanks 142. Holding tanks 142 typically contain a liquid, such as a deionized water, to prevent the gel from drying. In addition, the liquid supports the gel to prevent the gel from sagging or tearing under its own weight. Typically, the gels remain in the holding tank until gels are ready to be scanned and the selected protein spots are cut from the gel.

The gels 36 and the gel clamp 52 are sequentially transferred from the robotic assembly 140 for staining gels to cutting assembly 16 as shown in FIG. 1 and FIGS. 33–52. As shown in FIG. 33, cutting assembly 16 includes a robotic assembly 450 for manipulating the gels 36, scanning and imaging devices 452, and gel cutting apparatus 454. In the illustrated embodiment, two gel scanning and imaging devices 452 and two gel cutting devices are shown, although the actual number of devices can vary depending on the desired throughput of the assembly. A gel relaxing device 710 is also provided to level and flatten the gel as discussed hereinafter in greater detail.

Referring to FIG. 33, robotic assembly 450 is a computer controlled assembly having a robotic arm 456 pivotally coupled to a base 458. Base 458 is mounted on a movable horizontal support rail 460. Support rail 460 has opposite ends 462 coupled to vertical supports 464. A cross bar 466 as shown in FIG. 33 extends between the top ends 468 of vertical supports 464 to stabilize vertical supports 464 and robotic assembly 450.

Robotic arm 456 of assembly 450 is movable in vertical and horizontal directions to manipulate gel 36 from the staining assembly 14 to scanning device 452 and gel cutting apparatus 454 as discussed hereinafter in greater detail. As shown in FIG. 35, a motor 470 is mounted on vertical support 464 and is coupled to horizontal rail 460 for moving horizontal rail 460 along a vertical axis of vertical support 464. In one embodiment of the invention, motor 470 is operatively connected to a drive pulley 472 to drive a continuous cable 474, belt or other drive member. The cable 474 is in turn coupled to horizontal support rail 460. Motor 470 is actuated to drive the cable 474 to raise and lower the horizontal support rail along a vertical track 476 extending the height of vertical supports 464 as shown in FIG. 35.

Referring to FIGS. 34–38, robotic arm 456 is pivotally connected to base 458 by pivot shaft 478 extending outwardly from base 458. Base 458 includes a drive assembly, shown as motor 480 for moving base 458 along the length of horizontal support rail 460 between vertical supports 464. Motor 480 is connected to a drive assembly, such as a drive belt for selectively moving base 458 and robotic arm 456 along horizontal support rail 460. Motor 480, which can be electrically operated or pneumatically operated is operatively coupled to an operating computer to control the movement and timing of base 458.

An operating motor 482 for pivoting robotic arm 456 is mounted on base 458. Motor 482 is operatively connected to a pivot shaft 478 to pivot robotic arm 456 about an axis perpendicular to base 458 and horizontal support rail 460. Motor 482 is typically an electric motor that is operatively connected to the operating computer.

FIG. 34 is a top view of robotic assembly 450 showing robotic arm 456 in a vertical position and showing the robotic arm 156 of staining assembly 14. Robotic arm 456 includes an operating arm 484 coupled to pivot shaft 478 and oriented substantially parallel to base 458. A support arm 486 is coupled to operating arm 484 and extends in a direction substantially perpendicular to operating arm 484. Support arm 486 has a length sufficient to support gel 36 and a support tray 488 shown in FIG. 38 as discussed hereinafter in greater detail.

Referring to FIG. 35, support arm 486 has a body portion with a bottom 492 and a flange 494 extending outwardly from bottom edge 492. Flange 494 is spaced from a front side 496 of support arm 486 a distance to define a ledge 498. In the illustrated embodiment, ledge 498 and flange 494 have a length corresponding substantially to the length of support arm 486. Preferably, ledge 498 and flange 494 have dimensions to receive and support tray 488. Trya 488 forms a supporting member for supporting a gel during scanning and cutting of the gel.

As shown in FIGS. 36 and 37, flange 494 includes a substantially U-shaped slot 500 having an open end along a bottom edge 502 of flange 494. In the embodiment shown, slot 500 is positioned in the middle of flange 494. A proximity switch 584 is provided on flange 494 to detect the presence of a tray 488. A locking pin 504 extends through slot 500 for reciprocal movement toward ledge 498 within slot 500. Locking pin 504 includes a shaft 506 and an enlarged head 508 for coupling to tray 488 as shown in FIGS. 35 and 38.

Referring to FIG. 37, shaft 506 of locking pin 504 is coupled to a lever arm 510 at a first end 512. Lever arm 510 is pivotally coupled to a fixed pivot pin 514 at a middle section between first end 512 and a second end 516. Lever arm 510 pivots about pin 514 to move locking pin 504 within slot 500 toward ledge 498. An operating assembly 518 is coupled to second end 516 of lever arm 510 to pivot lever arm 510 about pin 514.

Operating assembly 518 in one embodiment of the invention shown in FIG. 37 includes a pneumatic cylinder and piston assembly 520 for selectively moving a piston rod 522. Piston rod 522 has an operating end 524 coupled to an operating linkage 526. Operating linkage 526 includes a first arm 528 having a first end 530 pivotally coupled to operating end 524 of piston rod 522 and a second end 532 pivotally coupled to arm 486 by a fixed pivot pin 534. Operating linkage 526 includes a second arm 536 having a first end 538 pivotally coupled to operating end 524 of piston rod 522 and second end 540 pivotally coupled to lever arm 510. Pneumatic cylinder 520 includes air supply conduits 541 extending to a pressure source 542 shown in FIG. 35 for selectively supplying air pressure to cylinder 520 to move piston rod 522 in the desired direction.

Referring to FIG. 37, pneumatic cylinder 520 is actuated to extend piston rod 522 outwardly. As piston rod 522 moves outwardly, linkage arms 528 and 536 move second end 516 of lever arm 510 downwardly causing lever arm 510 to pivot about pivot pin 514. The pivotal movement of lever arm 510 moves end 512 and locking pin 504 upwardly into a locking position.

As shown in FIGS. 38–40, tray 488 is dimensioned to support a gel 36 and the gel clamp and to cooperate with scanner assembly 452 and gel spot cutter assembly 454. Referring to FIG. 39, tray 488 in one embodiment of the invention has a substantially rectangular shape with parallel side edges 542, a first end 544 and a second end 546. First end 544 of tray 488 includes a handle portion 548 extending outwardly substantially in the plane of tray 488. As shown in FIG. 39, handle 548 has a width slightly less than the overall width of tray 488. Handle 548 in the embodiment illustrated includes two spaced-apart apertures 550 having a circular configuration with a beveled edge 552. Apertures 550 can be provided in handle 548 for mounting tray 488 on a suitable storage hanger or robotic device.

A triangular shaped aperture 554 having a beveled edge 556 is formed in handle 548. Preferably, aperture 554 is centrally located in handle 548. Triangular shaped aperture 554 is dimensioned to cooperate with a locking pin 504 of robotic arm 456 for transferring tray 488 and the associated electrophoresis gel between various work stations. Triangular shaped aperture 554 is oriented with its apex 558 positioned toward an outer edge 560 of handle 548 and with its base 562 spaced inwardly from the outer edge 560.

Tray 488 includes a recessed area 564 at first end 544 extending between side edges 542. As shown in FIG. 39, recessed area 564 has a substantially planar surface with a notched portion 566 adjacent each side edge 542. Two spaced-apart openings 568 are provided in recessed area 564. In the embodiment illustrated, openings 568 have a substantially rectangular configuration.

Referring to FIG. 39, notched portions 566 have a U-shaped recess 570, an inclined face 572 and a flat top portion 574 extending substantially perpendicular to the bottom wall of recessed area 564. Flat top portion 574 is dimensioned to support a gel clamp as shown in FIG. 38.

In the embodiment illustrated, side portions 576 extend inwardly from the respective side edge 542. A flat plate member 578 is coupled to side portions 576 on a top surface thereof. As shown in FIG. 39, plate 578 is coupled to the top face of the body of tray 488 to define recessed area 564. Plate 578 is generally made of glass or other material to enable scanning and imaging of the gel.

In one embodiment of the invention, side portions 576 of tray 488 are provided with a plurality of spaced-apart ridges 580 that are oriented at an acute angle with respect to the respective side edge 542. As shown in FIG. 39, ridges 580 are oriented at an angle of about 45° and extend from the respective side edge 542 toward second end 546 of tray 488. Ridges 580 terminate a short distance from a side edge 582 of plate 578. Ridges 580 are oriented to direct a washing liquid from side edges 542 of tray 488 toward plate 578 when tray 488 is suspended vertically. Ridges 580 enable a rinse liquid to drain away from side edges 542 when suspended vertically to minimize the amount of the rinse liquid remaining on side edges 542 which can be transferred to guide rails of cutting apparatus 454.

Plate 578 is dimensioned to support an electrophoresis gel obtained from a two dimensional electrophoresis separation process as known in the art. Plate 578 is substantially flat and has a planar top surface for supporting the gel. As shown in FIG. 39, plate 578 has side edges 582 that overlie side portions 576 for coupling plate 578 to side portions 576. In a preferred embodiment of the invention, plate 578 is made from a flat sheet of glass. Tray 488 is typically made of metal having a corrosion resistant and non-reactive finish to prevent contamination of the electrophoresis gel and reagents that may contact tray 488.

Referring to FIG. 40, tray 488 is dimensioned to support a gel 36 and the gel clamp 52. The gel clamp fits in recessed area 564 of tray 488 with the shoulders of the gel clamp engaging top surface 574 of notches 566. Recessed area 564 preferably has a depth corresponding substantially to the thickness of the clamping jaw of the gel clamp so that gel 36 can lay flat on plate 578.

Robotic assembly 450 is positioned to cooperate with the robotic assembly 140 of staining assembly 14. As shown in FIGS. 33 and 34, the guide rails 144 of robotic assembly 140 overlap with robotic assembly 450 so that the robotic assemblies are able to transfer a gel and gel clamp between the robotic assemblies.

As shown in FIG. 38, a tray 488 is captured by robotic arm 486 by inserting locking pin 504 through aperture 554 of tray 488. Pneumatic cylinder 520 is actuated to move locking pin 504 from the unlocked position to the locked position toward ledge 498 to draw tray 488 into a tight clamping engagement with ledge 498. A proximity switch 584 on flange 494 is contacted by tray 488 to detect when tray 488 is secured to arm 456. Proximity switch 584 is connected to the central operating computer to control the operation of robotic arm 456.

Once robotic arm 456 captures tray 488, robotic arm 456 is moved into the position shown in FIG. 34 for cooperating with the robotic arm 156 of robotic assembly 140 of staining tank assembly 14. Referring to FIGS. 41–43, robotic arm 456 is pivoted to position tray 488 at an incline. Typically, tray 488 is oriented at an angle of about 70° to about 85° from the horizontal position. Robotic arm 156 of staining tank assembly carries a gel 36 with a gel clamp 52 and is moved slowly toward tray 488 as shown in FIGS. 41–43. Preferably, gel 36 is aligned with plate 578 of tray 488 and moved into contact so that the bottom end of the suspended gel 36 contacts tray 488 as shown in FIG. 42. The robotic arm 156 continues to move toward tray 488 until the entire gel is placed on plate 578 and the gel clamp 52 is positioned in recessed area 564 of tray 488. The operating arms of robotic assembly 140 are retracted and the robotic arm is moved away from tray 488 to release the gel clamp and transfer the gel and gel clamp to tray 488. In the illustrated embodiment, the tray 488 is held stationary while the gel and gel clamp are moved toward tray 488. In alternative embodiments, the gel can be held stationary and tray 488 can be moved into contact with the gel. Preferably the gel is loose on the tray and the wet surface of the gel enables the gel to adhere or stick to the plate without the need to bond or otherwise fix the gel to the tray.

Figure 44:
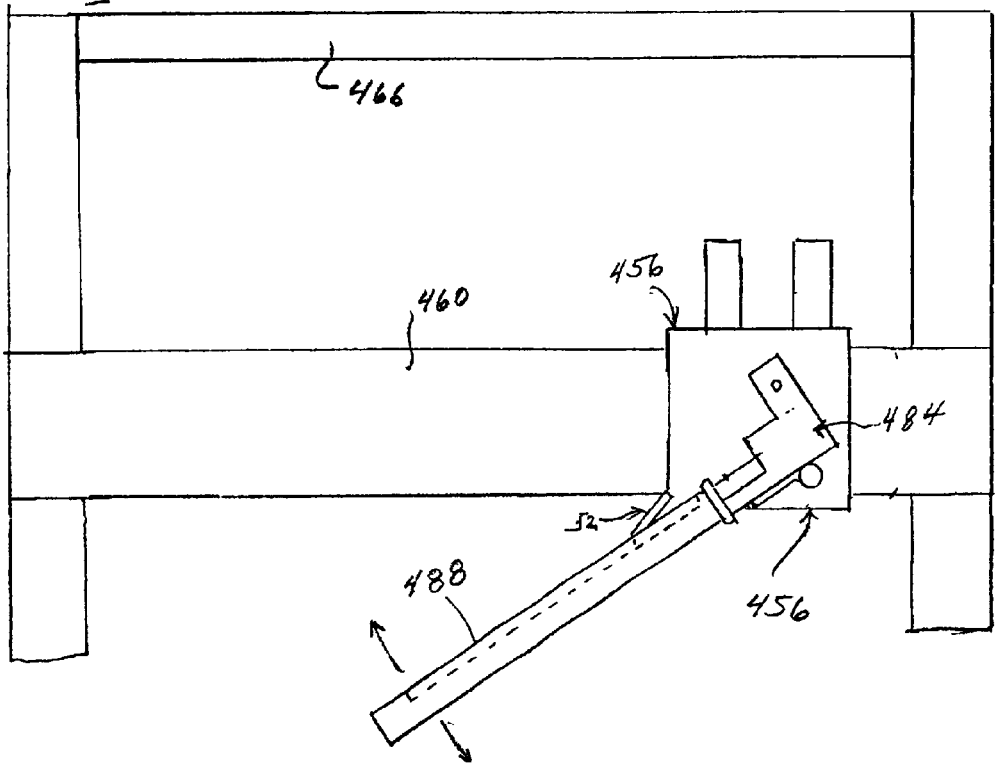
FIG. 44 is a side view showing the robotic arm pivoting the tray and gel to a horizontal position.
Figure 45:
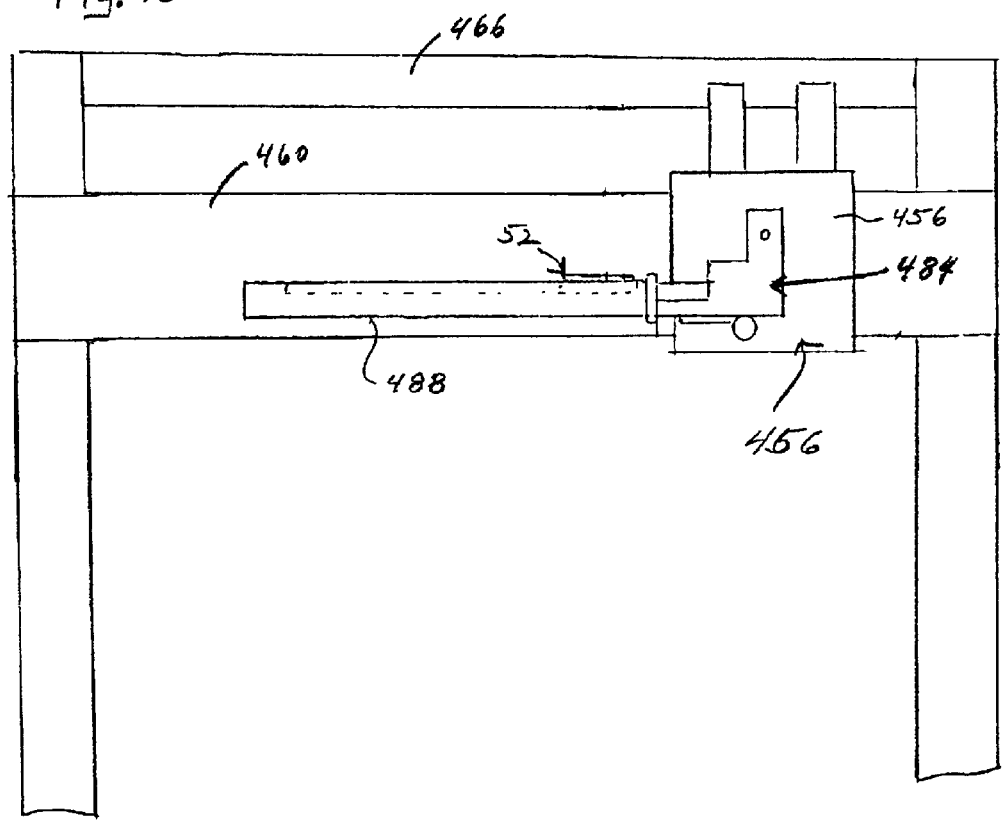
FIG. 45 is an end view showing the gel and gel clamp on the tray being raised to engage a device to open the gel clamp to relieve stress in the gel.

Once the gel and gel clamp are captured on tray 488, robotic arm 456 is pivoted to orient tray 488 in a substantially horizontal position as shown in FIG. 44. The gel 36 when placed on plate 578 typically captures air bubbles between the gel and plate 578. In preferred embodiments, it is desirable to remove air bubbles to enable the gel to lay flat on tray 488. Depending on the size and location of the trapped air bubbles, the bubbles create an uneven surface on the gel which can interfere with the scanning of the gel and the cutting of selected spots from the gel.

In one embodiment of the invention, the gel clamp 52 is opened while the tray 488 is oriented in the horizontal position to allow the gel to relax and to enable the air bubbles to escape. A vertical bar can be positioned above robotic arm 456 so that when horizontal support rail 460 is then moved upward, the bottom end of the bar contacts and opens the jaws of the gel clamp 52. Tray 488 is maintained with the jaws of the gel clamp open for a time sufficient to enable the gel to lay flat and the air bubbles to escape from between the gel and plate 578. In other embodiments, tray 488 can be raised and lowered several times to open and close the jaws of the gel clamp repeatedly to enable the air bubbles to escape.

Figure 48:
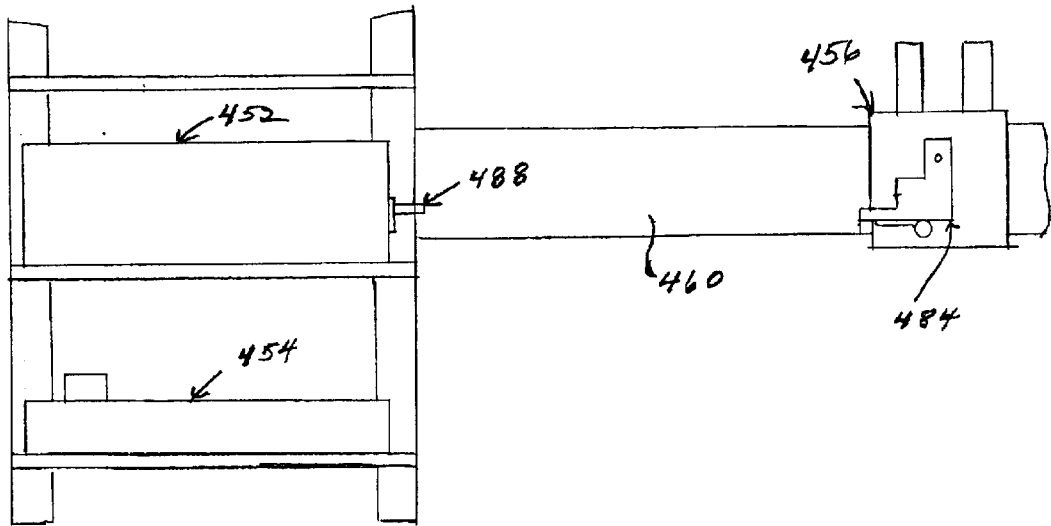
FIG. 48 is a side view showing the robotic arm retracted from the scanning device.
Figure 49:
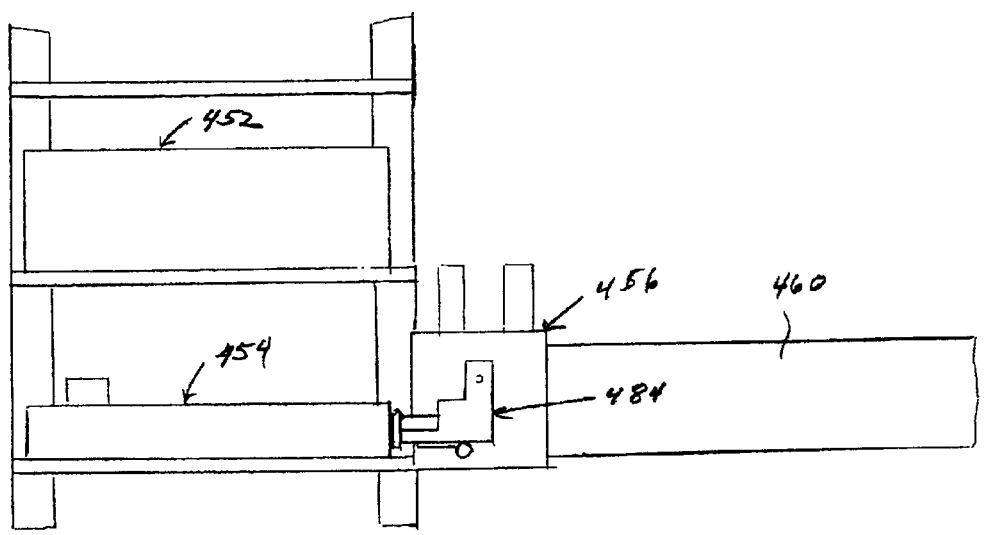
FIG. 49 is a side view of the robotic arm positioning the tray and gel into a cutting device.

After gel 36 and the gel clamp are positioned on tray 488, robotic arm 456 is moved to a position for inserting tray 488 into scanner 452 as shown in FIG. 46. Robotic arm 456 supports tray 488 in a horizontal position and aligns tray 488 with the opening of the scanner 452. Robotic arm 456 and base 458 are moved along horizontal support arm 460 to insert tray 488 and gel 36 into scanner 452 as shown in FIG. 47. Locking pin 198 is moved outwardly and robotic arm 456 releases tray 488 to leave tray 488 in scanner 452 during the scanning process as shown in FIG. 48 while robotic arm 456 can proceed to capture a second tray and repeat the process. Robotic arm 456 is programmed to move locking pin 198 to the unlocked position and then move downwardly to remove pin 198 from tray 488. At the end of the scanning cycle, robotic arm 456 captures tray 488, withdraws tray 488 from scanner 452 and transfers tray 488 to gel spot cutter 454 as shown in FIG. 49. Robotic arm 456 is then available to capture another tray and gel which can be delivered to a scanner or gel cutting device.

Scanner 452 is typically a commercially available scanning and imaging device used for electrophoresis gels to identify the locations of proteins in the gel. The scanner illuminates the gel and captures an image of the stained gel spots on the gel. The scanner then compares the image with a library of images from known proteins or biological samples using known software programs. Scanner 452 is operatively connected to the operating system and computer to identify the stained protein spots and to target certain protein spots according to the selected processing protocol. The information obtained from the scanning, imaging identification and targeting of the protein is stored in the computer and transferred to gel spot cutter 454 in the form of excising or cutting instructions to cut selected spots from the gel. The image signal from the scanner is processed in the computer of the control system and generates a cutting signal for directing and controlling spot cutting assembly 454. The control system is connected to the scanner and receives a signal from the scanner indicating completion of the scanning cycle. The control system actuates robotic arm assembly 592 to capture the tray 488 in the scanner, remove the tray from the scanner and transfer the tray to cutting assembly 454.

In the illustrated embodiment, several scanning devices 452 and gel spot cutting assemblies 454 are placed on a shelf unit in a stacked relation to enable processing of several gels simultaneously. The actual number of the scanning devices and gel spot cutting devices can depend on the desired throughput of the system.

Cutting assembly 454 as shown in FIG. 50 includes a housing 590 supporting a robotic arm assembly 592. Housing 590 includes a base 594 defining a work surface with side walls 596 and an open front end 598.

Base 594 includes a pair of spaced-apart guide rails 600 for receiving tray 488. Guide rails 600 have an upright section and an inwardly extending flange to contain tray 488 and to allow robotic arm 484 to slide tray 488 into and out of the cutting position shown in FIG. 50. In one embodiment of the invention, base 594 includes a recessed area between guide rails 600 to receive tray 488. The recessed area has a depth corresponding substantially to the thickness of tray 488 so that a top edge of tray 488 is substantially in the same plane as base 594.

Robotic arm assembly 592 is mounted on base 594 for movement in a direction substantially parallel to base 594. Robotic arm assembly 592 includes a motor 602 attached to base 594 of housing 590 adjacent the recessed area. A first movable arm 604 has a first end 606 operatively connected to motor 602 for pivoting first arm 604 about an axis substantially perpendicular to the plane of base 594. First arm 604 has a second end 608 having a second motor 610 coupled thereto. A second arm 612 has a first end 614 operatively coupled to second motor 610 for pivoting about an axis of second motor 610 parallel to the axis of rotation of first motor 602. Second arm 612 includes a second end 616 having a cutting head assembly 618 for excising a sample from an electrophoresis gel.

Robotic arm assembly 592 is operatively connected to a computer for directing the movement of first and second arms 604 and 612, respectively, as well as cutting head assembly 618. The computer processes the signals from scanner 452 and generates a signal for actuating first motor 602 to pivot first arm 604 about the axis of motor 602 in the direction of arrow 620. Simultaneously, the computer produces a signal to actuate second motor 610 to rotate the second arm about the axis of motor 610 in the direction of arrow 622. The controlled movement of motors 602 and 610 move cutting head assembly 618 to a selected position with respect to an electrophoresis gel on tray 488 for excising a selected sample from the gel. In a preferred embodiment of the invention, the computer receives the imaging signal from scanning device 452, processes the signal to identify the selected locations on the electrophoresis gel, and produces a cutting signal based on polar coordinates for excising the sample from the gel. In alternative embodiments, the computer can generate a cutting signal to direct robotic arm assembly 592 based on XY coordinates.

In one embodiment, one guide rail 600 includes a spring biased detent 644 to engage a recess of tray 488 to position tray 488 in a specific location in cutting assembly 454. In one embodiment of the invention, detent 644 is a spring biased, pivotally mounted arm 646 having a roller that allows tray 488 to be inserted and removed from guide rails 600. Preferably, detent 644 includes a microswitch 648 which is operatively connected to the computer and produces a positioning signal to indicate that tray 488 is properly positioned in cutting assembly. Once tray 488 is properly positioned in cutting assembly as indicated by microswitch 648, the computer actuates robotic arm assembly 592 to cut and transfer the gel spot to the microtiter plate 624.

Cutting head 618 can be any suitable device capable of excising a selected portion of the gel and transferring the excised portion to a microtiter plate 624. In one embodiment of the invention, the cutting head includes a pneumatic cylinder having a retractable piston rod. The piston rod is coupled to and reciprocates a supporting block that includes an internal passage having a bottom end, a cylindrical internal cavity and a supply passage. A hollow tubular cutting punch extends downwardly from bottom end of the supporting block and is in communication with the cavity and the internal passage. The cutting punch reciprocates to cut and remove a section of the gel. Cutting punch can include an internal piston or fluid pressure source to eject the cut gel spot from the punch into the appropriate well of the microtiter plate.

In operation, cutting head 618 is positioned above the gel to excise the sample identified by scanning and imaging device. The cutting head 618 is actuated to cut and remove a gel sample from the gel on tray 488. The robotic arm assembly then moves the cutting head 618 to a position directly above a selected well 626 of a microtiter plate 624 and the gel sample is ejected. In a preferred embodiment, a wash liquid such as deionized water is introduced through a supply conduit which flows through the cutting punch to assist in ejecting the cut gel piece from the punch and to wash any residue from the punch. The sequence is repeated until each identified sample is cut from the gel and transferred to a respective well in a microtiter plate.

Robotic assembly 592 is primarily programmed and operated by the computer to excise selected portions or samples from the gel and automatically transfer the excised portion to a sample receiving microtiter tray 624. As shown in FIG. 50, microtiter plate 624 is a standard multiwell sample plate as known in the art. Plate 624 typically has a substantially rectangular shape with a top face and side walls. A plurality of spaced-apart wells 626 are formed in the top face and are dimensioned to contain a sufficient volume of a sample, typically about 10 to about 50 microliters. In one embodiment of the invention, microtiter plate 624 contains an array 96 of wells 626 arranged in rows and columns. The number of wells 626 in plate 624 can vary depending on the manufacturer of the tray, the nature of the samples being analyzed and the process for carrying out the analysis of the sample. Preferably, a bar code 628 is provided on the side wall or the top surface to identify the respective plate 624 and the samples contained in wells 626. Bar code 628 can be used to track the location of the microtiter plate within the apparatus and for cataloging the samples cut from the gel slab.

Referring to FIG. 50, a storage assembly 630 is coupled to cutting assembly 454 for sequentially supplying a microtiter plate 624 for receiving gel spots or samples excised from the gel slab. Storage assembly 630 includes a support surface 632 extending from a housing 634. Support surface 632 extends through an opening in side wall 596 of housing 590 of cutting assembly 454. Support 632 has a top surface preferably lying in the same plane as base 594 and is positioned in a recess adjacent the recessed area. In one embodiment, a recess 636 is provided adjacent support surface 632. Recess 636 includes an inclined bottom wall that slopes toward an opening to drain any spilled liquids onto the base. A suitable collection vessel can be placed below the opening to collect the liquids.

Support 632 includes a conveyor 638 extending between housing 634 and an outer end of support 632. In the embodiment illustrated, conveyor 638 is a continuous belt extending from the outer end of support 632 to housing 634 as shown in FIG. 50. Conveyor 638 is typically a motor driven belt having a width that is less than a width of support 632.

The outer end of support 632 defines a work station for receiving a microtiter plate 624 during the cutting and loading operation of cutting assembly 454. Storage assembly 630 includes a supply magazine 640 and a receiving magazine 642 coupled to housing 634. Supply magazine 640 contains a plurality of stacked microtiter plates which can be dispensed sequentially to conveyor 638.

In operation, a microtiter tray is delivered from supply magazine to the conveyor 638. The conveyor motor is actuated to convey plate 624 to the work station. Robotic arm assembly 592 is then actuated by the computer to excise predetermined samples from the gel and sequentially transfer the excised portion to a respective well 626 of sample microtiter plate 624.

After the excised samples from the gel are transferred to sample microtiter plate 626, the conveyor is actuated to convey sample microtiter plate 624 to a position below receiving magazine 642. Plungers are positioned below receiving magazine 642 to push sample microtiter plate 624 upwardly into receiving magazine 642. Detents retain microtiter plate 624 in receiving magazine 642. One example of a suitable storage assembly that can be used in combination with the cutting assembly is available from Packard Biosciences Corporation and is sold under the tradename Platestack.

At the completion of the cutting process, robotic arm 484 is again moved into a position to couple to the tray 488 with the gel and gel clamp. Robotic arm 484 is moved to a position immediately below handle of tray so that locking pin 504 is aligned with triangular opening 554. Robotic arm 484 is then raised upwardly so that locking pin 504 passes through triangular opening 554. Locking pin 504 is then actuated to move to the locking position to capture tray 488. Robotic arm 484 slides tray 488 outwardly from cutting assembly 454 and returns tray 488 to the inclined position shown in FIG. 43. At that time, robotic arm 156 of staining assembly is aligned with and moved into position to insert the coupling pins 198 through the openings in gel clamp 52. Arms 196 of robotic arm 156 are pivoted outwardly to capture the gel clamp. In one embodiment, robotic arm 156 of staining assembly 14 lifts gel clamp 52 upwardly in a substantially vertical direction to separate gel clamp 52 and gel 36 from tray 488. The gel, which is still coupled to the gel clamp 52, slides upwardly along the glass plate until it is lifted completely from tray 488. In an alternative embodiment, robotic arm 156 moves horizontally to pull gel clamp 52 and gel 36 away from tray 488 in a horizontal direction. Tray 488 can be held stationary while robotic arm 156 moves away from tray 488. In still another embodiment, tray 488 and robotic arm 156 can be moved apart in a horizontal direction simultaneously.

After gel clamp 52 and the gel are removed from tray 488, robotic assembly 140 returns the gel and gel clamp 52 to a storage tank of the staining assembly 14. Preferably, the gel is placed in a liquid, such as water, so that the gel can be analyzed or processed further at a later time, if desired. In an alternative embodiment, the gel and the gel clamp 52 are carried to the discarding assembly 402 as shown in FIG. 31 where the gel 36 is separated from the clamp 52. The clamp 52 can be removed from the discard assembly 402 by the robotic assembly 156 and transferred to a storage rack. Alternatively, the gel clamp 52 can be removed manually from the discarding assembly 402 and transferred to a suitable storage rack.

The robotic arm 156 of robotic assembly 140 again captures a gel and gel clamp 52 that has been stained and treated according to the selected protocol. The gel is transferred to the tray 488 and the scanning and cutting process is repeated. In a preferred embodiment, tray 488 is cleaned before a gel is placed on the tray to remove any broken gel pieces, gel or contaminants remaining on tray 488 that could interfere with the scanning or cutting steps.

Referring to FIGS. 51–54, a cleaning assembly 650 is positioned to cooperate with robotic assembly for manipulating tray 488. As shown in FIG. 51, tray 488 is suspended directly above cleaning assembly 650 with tray 488 oriented in a vertical position. Cleaning assembly 650 includes a tank 652 having a bottom wall 654, side walls 656 and end walls 658. Tank 652 has a dimension to receive tray 488 in its vertical orientation.

A spray assembly 660 is coupled to a top end of each side wall 656 of tank 652. Spray assembly 660 includes mounting legs 662 coupled to the respective side wall 656 for supporting a cross member 664 extending between legs 662. Cross member 664 is oriented above the top end of each side wall 656 as shown in FIG. 53. A plurality of spray nozzles 666 are mounted on each cross member 664 facing inwardly toward the center of tank 652. Preferably, spray nozzles 666 are spaced apart a distance to direct a spray of wash liquid onto tray 488 to spray and wash both sides of tray 488 simultaneously. Spray nozzles 666 are connected to a supply conduit 668 for supplying nozzles with a wash liquid. Supply conduit 668 is connected to suitable wash liquid supply source and pump for supplying a wash liquid under sufficient pressure to remove debris from tray 488. Preferably, the pump is operatively connected to the central computer to coordinate the spray washing step with the movement of the robotic assembly and tray 488.

The wash liquid can be any suitable liquid that is able to effectively clean tray 488 to remove residues and the like from the tray 488. A suitable wash liquid can be distilled or deionized water. In one preferred embodiment, the wash liquid contains a volatile liquid or solvent to enable the wash liquid to evaporate quickly and to wash any residual proteins from the tray. In one preferred embodiment, supply conduit 668 is connected to a water supply through line 669 and supply source 671 of a second solvent through a line 673. The wash cycle first directs a spray 675 of water onto tray 488 for a sufficient time to remove debris or gel fragments. The second solvent is preferably ethanol. After a sufficient wash cycle with water, the ethanol is supplied through line 673 to mix with the water to wash the tray with an ethanol/water mixture. The water supply is gradually reduced to increase the ethanol concentration in the wash liquid until the wash liquid contains only ethanol with no added water.

Spray assembly 660 also includes an air knife 670 for directing a jet of drying air to tray 488. Air knife 670 includes a narrow slot 677 for directing a substantially flat air stream 676 onto tray 488. Air knife 670 is mounted on cross member 664 and connect to a conduit 672 for supplying air to nozzles 670. Conduit 672 is connected to a pressured air source which is controlled by the computer to coordinate the air stream with the manipulation of tray 488. In one embodiment, a suitable filter is included to remove particulates from the drying air. The air source typically supplies air at a pressure of about 120 psi to air knife 670. Air knife 670 is a standard air knife that is commercially available from various manufacturers.

In the method of the invention, the robotic arm supports tray 488 vertically above tank 652 as shown in FIG. 51. Tray 488 is then lowered into tank 652 and spray nozzles 660 are actuated to direct a spray 673 of wash liquid onto tray 488. In one embodiment, spray nozzles 660 are actuated while tray is being lowered into tank 652 so that a direct spray is applied to the entire surface of the tray. Alternatively, spray nozzles 660 are actuated after the tray 488 is positioned in the tank. Spray nozzles 660 continuously direct spray 675 of the wash liquid onto tray 488 in a generally downward direction with respect to tank 652 for a sufficient time to remove any gel pieces and residue from tray 488. The wash liquid drains downward into tank 652 and exits through a drain opening 674 where the wash liquid is discharged or recycled.

At the end of the cleaning cycle, spray nozzles 660 discontinue the wash liquid and air nozzles 670 are actuated. Air nozzles 670 direct an air jet 676 onto tray 488 as shown in FIG. 54. Preferably, air jet 676 is directed against tray 488 in a generally downward direction with sufficient force to remove excess wash liquid and dry the surfaces of tray 488.

In a preferred embodiment, the robotic assembly raises tray while the air jet 676 is continuously directed to the tray to dry the surfaces of the tray and blow any remaining droplets of wash liquid downwardly into tank 652. The air jet 676 is applied for a time and with a force sufficient to dry the tray and remove the wash liquid. Tray 488 is then conveyed into position for receiving a gel for scanning and cutting as discussed above.

The electrophoresis gel 36 is very pliable and when wet can stick to most surfaces. As robotic arm 156 moves toward tray 488, gel 36 sticks to plate 578 of tray 488. More notable, the gels frequently exhibit dimensional changes during the staining process. The different liquid reagents cause the gels to shrink or expand depending on the reagent. While the edge of the gel is clamped in the gel clamp, the clamped edge cannot expand or contact with the rest of the gel which cause the gel to distort. At the end of the gel staining process, the gel in the clamp has a wavy, curtain-like appearance. The distorted gel 36 often captures small air bubbles between plate 578 and the gel 36. The bubbles, and particularly large bubbles, prevent the gel 36 from laying flat on plate 578 which can interfere with the scanning of the gel and produce inaccurate or inconsistent results. The scanner in one embodiment illuminates the gel from below with the scanning/imaging detector positioned above the gel. The trapped air bubbles can cause the illuminating light to diffract, which results in an incorrect image being scanned and recorded. In one preferred embodiment, the trapped bubbles are substantially removed or at least flattened to enable the gel to lay substantially flat on the plate 578 of tray 488 so that the remaining air bubbles are sufficiently small to minimize or eliminate interference during scanning and cutting. The air bubbles are removed by applying a localized downward pressure on the bulges of the gel. The applied pressure is sufficient to displace the air bubbles without damaging the gel.

In one embodiment of the invention, a device 710 is provided to remove the air bubbles that are trapped between the gel and tray 488. Referring to FIG. 33, a gel leveling or relaxer device 710 is positioned to receive a tray 488 containing a gel from robotic arm 484. In a preferred embodiment, gel relaxer device is arranged in a stacked relation with scanner and spot cutter so that robotic arm 484 can insert and remove tray 488 from the device.

The gel relaxer device 710 is a stationary device which receives a tray 488 and applies a localized pressure on the bulge caused by the trapped air bubbles to displace or expel the air bubble from between the gel and the plate and to level the gel on the plate. As the tray 488 is inserted into device 710, the air bubbles, are pushed from the bottom end of the gel toward the gel clamp 52 where the air bubbles can escape. After the air bubbles are pushed toward the gel clamp 52, the jaws of the gel clamp 52 are opened to relieve the gripping pressure on the edge of the gel, which then allows the air bubbles to escape, thereby leveling the gel and allowing the gel to lay flat. The jaws are again closed to grip the gel and then tray 488 is carried to the scanner by robotic arm 484. Typically, the jaws of the gel clamp are opened for about 2-3 seconds. The jaws can be opened and closed a number of times as needed to allow the gel to lay flat.

Referring to FIGS. 55–65, gel relaxer device 710 includes a substantially flat base 712 having first end 714 and a second end 716. A pair of parallel guide rails 718 extend between first end 714 and second end 716 and are spaced apart a distance to receive tray 488. As shown in FIG. 56, guide rails 718 have an inwardly facing slot 720 having a dimension to receive the side edges of tray 488. Slot 720 has upper and lower surfaces that diverge outwardly at first end 714 of base 712 to define inclined portions 722 as shown in FIG. 56. Inclined portions 722 are provided at the receiving end of guide rails 718 for guiding tray 488 into slots 720.

Figure 55:
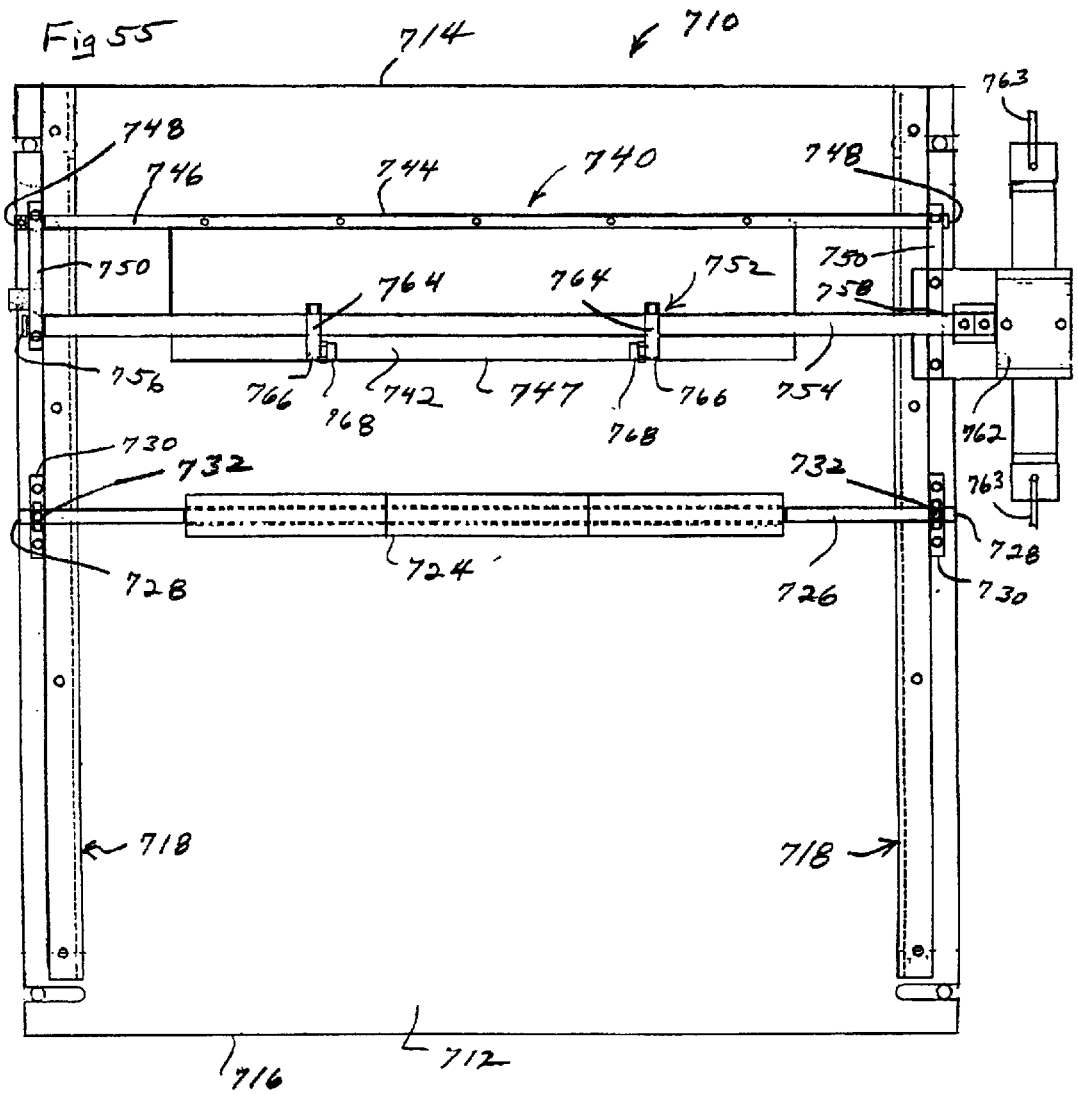
FIG. 55 is a top view of the gel relaxer in a preferred embodiment of the invention.

Preferably, base 712 has a dimension complementing the dimension of tray 488 and is able to receive tray 488 with its associated gel and gel clamp. As shown in FIG. 55, a roller 724 having a substantially cylindrical shape extends between guide rails 718 and is spaced above and parallel to base 712. Preferably, roller 724 is oriented substantially perpendicular to guide rails 712 and perpendicular to the sliding direction of tray 488 within slots 720 of guide rails 712.

Roller 724 defines a pressing member to contact the bulging portions of the gel caused by air bubbles trapped between the gel and plate 578 of tray 488. Roller 724 is mounted on a spindle 726 and is freely rotatable thereon. Spindle 726 includes axial ends 728 having roller bearings 729 that are mounted in a U-shaped recess 731 in brackets 730 adjacent each guide rail 718 to support roller 724 a predetermined distance from base 712. Preferably, brackets 730 include a threaded adjusting screw 732 extending through a threaded hole in the bottom of brackets 730 to adjust the height of each axial end 728 independently with respect to base 712. Referring to FIG. 58, U-shaped recess 731 in each bracket 730 includes a groove 733 dimensioned to receive a respective bearing 729. Bearings 729 are able to slide freely in a vertical direction within the respective groove 733. As shown in FIG. 58, adjusting screws 732 extend into the bottom portion of U-shaped groove 733 to support bearings 729 at each end of spindle 726 and to adjust the height of roller 724 with respect to base 712. Preferably, adjusting screws are independently adjustable to determine the angle of roller 724 with respect to base 712. In preferred embodiments of the invention, adjusting screws 732 position roller 724 to be substantially parallel with the plate 578 of tray 488 and the gel supported thereon when tray 488 is inserted into slots 720 so that roller applies a substantially uniform pressure across the width of the gel.

Figure 55A:
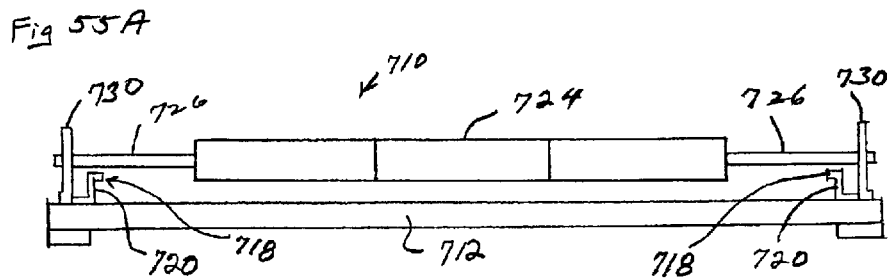
FIG. 55A is an end view of the gel relaxer of FIG. 55.

In one embodiment, bearings 729 are roller bearings having an inner and outer race where spindle 726 is press fitted into the inner race. The outer race fits within groove 733 and spindle 726 can rotate freely with respect to the outer race. In this manner, roller 724 can rotate freely on spindle 726 and spindle 726 can rotate with respect to the outer race of the bearing and brackets 730. In one embodiment, roller 724 is made from a flexible polymeric nylon material that is able to contact the gel without tearing or stretching the gel. In other embodiments, the roller can be made of metal or other materials. In the illustrated embodiment of FIG. 55A, roller 724 is formed in three sections that can rotate independently on spindle 726.

As shown in FIG. 56, roller 724 is positioned between first end 714 of base 712 and second end 716 to cooperate with the gel supported by the tray 488. Preferably, roller 724 is positioned a small distance above the gel on tray 488 so that roller 724 does not normally contact the gel when the gel is laying flat on plate 574 of tray 488. Referring to FIGS. 64 and 65, an air bubble 734 trapped between the gel and plate 574 forms a bulge 736 in the upper surface of the gel. As tray 488 slides along guide rails 718, roller 724 is spaced above the gel to define a gap 738. Preferably, the size of gap 738 defines the minimum size of bubble 734 that can be accepted without air bubble 734 and bulge 736 interfering with the scanning and cutting of the gel. Preferably, the height of roller 724 is adjusted to define a gap between roller 724 and gel 36 of about 1 mm to about 4 mm, and preferably about 1–2 mm. Typically, the gap is about equal to the thickness of the gel. Tray 488 slides below roller 724 as shown in FIG. 65 so that bulge 736 contacts the roller 724. As tray 488 is moved below the stationary roller 724, the roller pushes or squeezes air bubble 734 toward the end of the gel where the air bubble can escape from between the gel and the plate 574 of tray 488. In preferred embodiments of the invention, the bottom end of tray 488 is inserted into slots 720 so that the free edge of the gel slides below roller 724 so that air bubbles 734 are pushed toward the top end where the gel is coupled to the gel clamp.

Roller 724 is freely rotatable so that roller 724 is able to rotate with little resistance when it makes contact with a bulge to minimize damage to the gel. Bearings 729 ride freely in slot 733 so that the weight of rollers 724 applies a substantially constant downward force on the gel. In the event roller 724 engages an obstruction in the gel, such as a large bubble or bulge, the roller is able to slide upward within the slot 731 to prevent the roller from damaging the gel as the gel slides beneath the roller. Preferably, roller 724 has a weight to apply a pressure on the gel that is sufficient to flatten the bulges without damaging the gel.

Gel relaxer device 710 also includes a gel clamp actuating assembly 740 as shown in FIGS. 55 and 56. Assembly 740 includes a clamp actuating plate member 742 having a substantially planar configuration. Actuating member 742 has a first end 744 coupled to a pivot rod 746 and a second free end 747. Pivot rod 746 has axial ends 748 pivotally connected to brackets 750. As shown in FIG. 55, brackets 750 are mounted to base 712 adjacent guide rails 718. In the embodiment illustrated, brackets 750 are spaced between the first end 714 of base 712 and roller 724. Preferably, brackets 750 are positioned so that when tray 488 is fully inserted into slots 720 of guide rails 718, the gel clamp supported by tray 488 is positioned below actuating plate member 742. Actuating plate member 742 is assembled to pivot downwardly to engage and open the gel clamp as discussed hereinafter in greater detail. As shown in FIG. 57, plate member 742 is spring biased in the upward disengaging position by a spring 743 having one end coupled to a fixed post and a second end coupled to rod 746.

Actuating assembly 740 also includes an actuator 752 for operating actuating plate member 742. Actuator 752 includes a rod 754 positioned above second free end 747 of actuating plate 742. Rod 754 includes free ends 756 and 758. Free end 756 of rod 754 is pivotally coupled to a bracket 750, which is coupled to base 712 adjacent one guide rail 718. Free end 758 of rod 754 is coupled to a motor 762 coupled to base 712 adjacent the other guide rail 718. Motor 762 in one embodiment is a pneumatic motor that is able to rotate rod 754 about its axis to move actuating plate member 742. A pump and air control system supply pressurized air through supply lines 763 to operate motor 762 and rotate rod 754 between the disengaged position shown in FIG. 64 and the engaged position shown in FIG. 65. The air control system for operating the air pump is operatively connected to the computer control system for coordinating the operation of the actuating assembly with the operation of robotic assembly 484.

Referring to FIG. 55, two parallel arms 764 are coupled to rod 754 and extend radially outward therefrom. Arms 764 have an outer end 766 with a roller cam member 768 coupled to each arm 764. In the illustrated embodiment, cam members 768 are rollers coupled to each arm 764 by a pin 770. As shown in FIG. 55, arms 764 are spaced apart a distance to engage actuator plate member 742.

Figure 59:
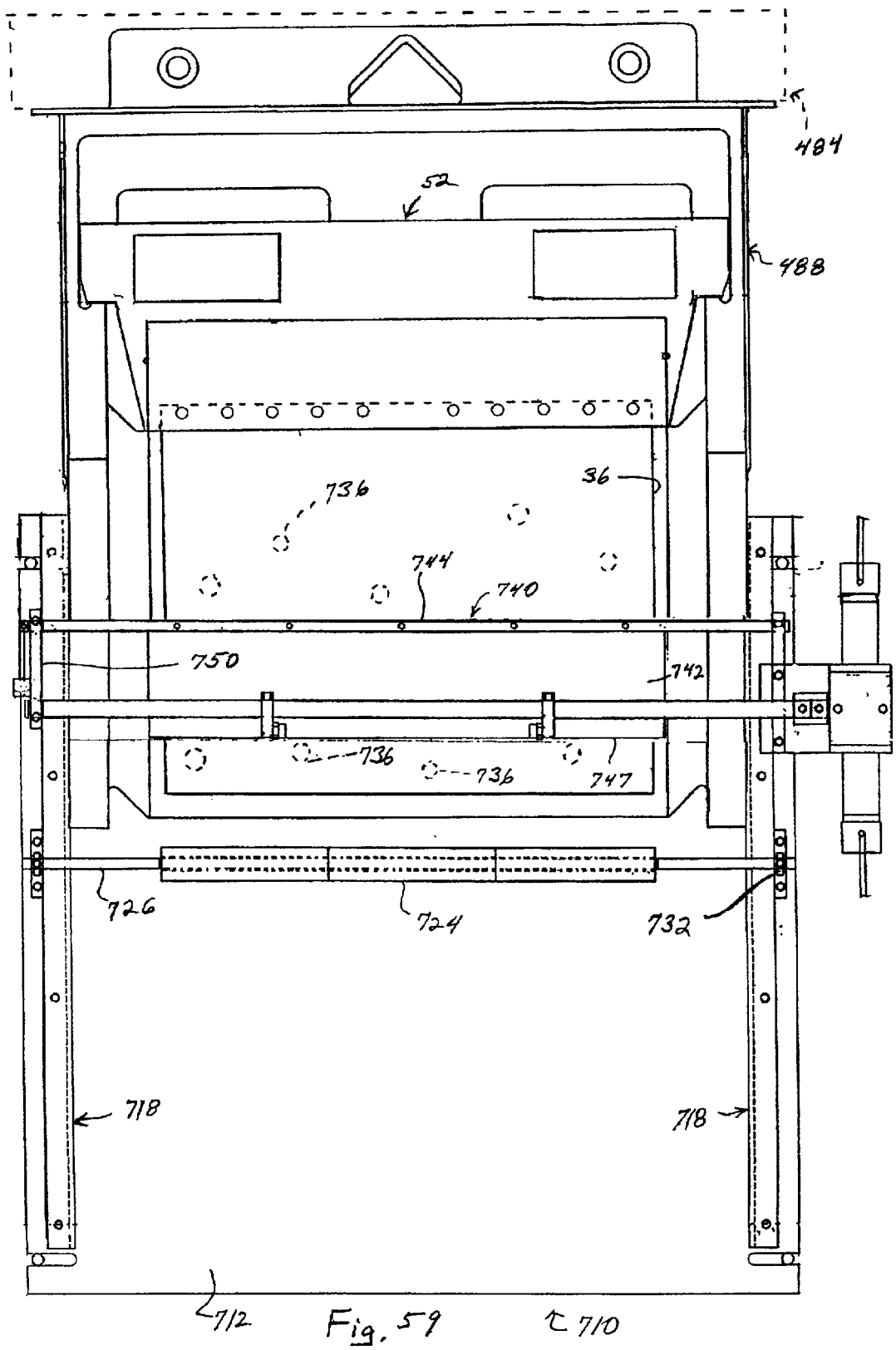
FIG. 59 is a top view of the gel relaxer showing the tray partially inserted.
Figure 60:
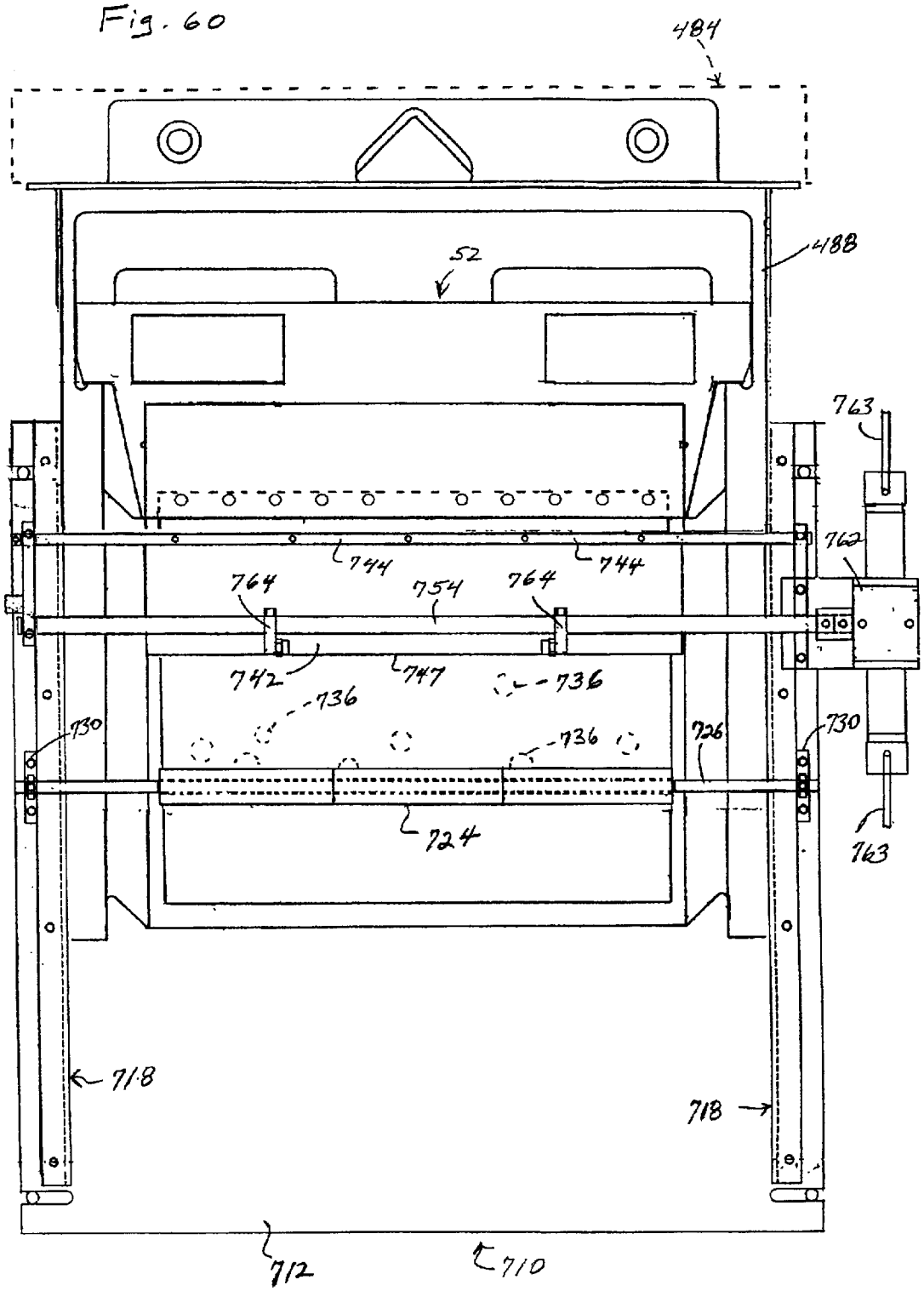
FIG. 60 is a top view of the gel relaxwer showing the roller displacing the air bubbles.
Figure 61:
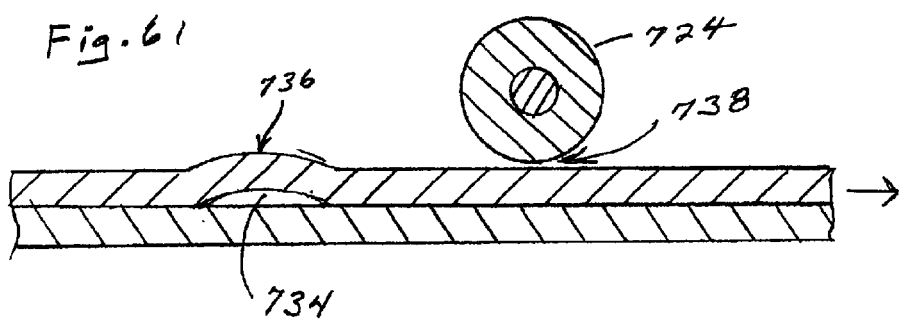
FIGS. 61 and 62 are side view in cross-section showing the air bubble being displaced from the gel.
Figure 62:
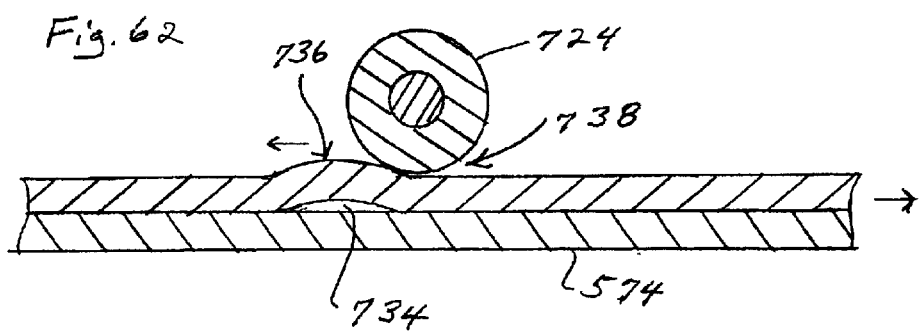

In use, the robotic arm 484 carries a tray 488 with a gel and gel clamp to gel relaxer device 710. Tray 488 is inserted into device 710 so that tray 488 and the gel slide below roller 724. As shown in FIGS. 59 and 60, as the gel and tray are inserted into device 710, the air bubbles trapped below the gel are pushed toward the gel clamp. Rollers 724 are able to rotate freely as the gel slides below the roller 724. Tray 488 is inserted completely into device 710 by the robotic arm as shown in FIGS. 63–65. At that time, motor 762 is actuated to rotate rod 754 and cam members 768 from the horizontal position shown in FIGS. 56 and 63 to the vertical position shown in FIG. 65. As shown in FIG. 65, cam members 768 are pivoted about the axis of rod 754 to engage actuator plate member 742 and pivot actuator plate member 742 about the axis of rod 746 downwardly into contact with the movable jaw of the gel clamp to open the jaws thereby allowing the gel to lay flat on the tray 488. Motor 762 is operatively connected to the central operating computer to coordinate the movement of the motor with the robotic assembly and the location and position of the tray.

Cam members 768 remain in the engaged position shown in FIG. 65 for a predetermined time to allow the gel to lay substantially flat and to enable the air bubbles below the gel to escape. Generally, the jaws of the gel clamp are opened for about 2–4 seconds which has been found sufficient to allow the air bubbles to escape. In one embodiment, motor 768 is actuated to open and close the jaws of the gel clamp two or more times to assist in allowing the gel to lay flat. The entire length of time for the robotic arm to insert tray 488 into gel relaxer 710, flatten the gel, and remove tray 488 is generally about 712 seconds. At the end of the gel relaxing stage, the cam members 768 are rotated upwardly so that the gel clamp again clamps onto the edge of the gel. The robotic assembly then removes tray 488 from device 710 and carries the tray to the scanner for capturing the image with a known stain pattern and identifies spots to be cut from the gel.

Roller 724 preferably does not contact the surface of the gel except in the area of the air bubbles and the bulges to minimize stretching or distortion of the gel as the gel slides below the roller 724. Roller 724 is positioned above the normal dimension of the gel to flatten the bulges and expel excess air from the bubble. It is not necessary to eliminate the air bubbles entirely. Preferably, the roller displaces at least a portion of the air from the bubble and presses the bulges down to enable the gel to lay substantially flat. Contact of the gel with the roller reduces the height and volume of the air bubbles and reduces the height of the bulges to a suitable dimension that do not interfere with the scanning and cutting steps. In the illustrated embodiment, the roller is in a fixed location and the gel is moved past the roller to apply a downward pressure onto the bulges so that air bubbles are displaced toward the trailing edge of the gel. In other embodiments, the gel is in a fixed location and the roller is moved across the surface of the gel. In both arrangements, the localized downward pressure is applied to the gel to displace air bubbles of a predetermined minimum height from a first end to a second end of the gel.

Figure 66:
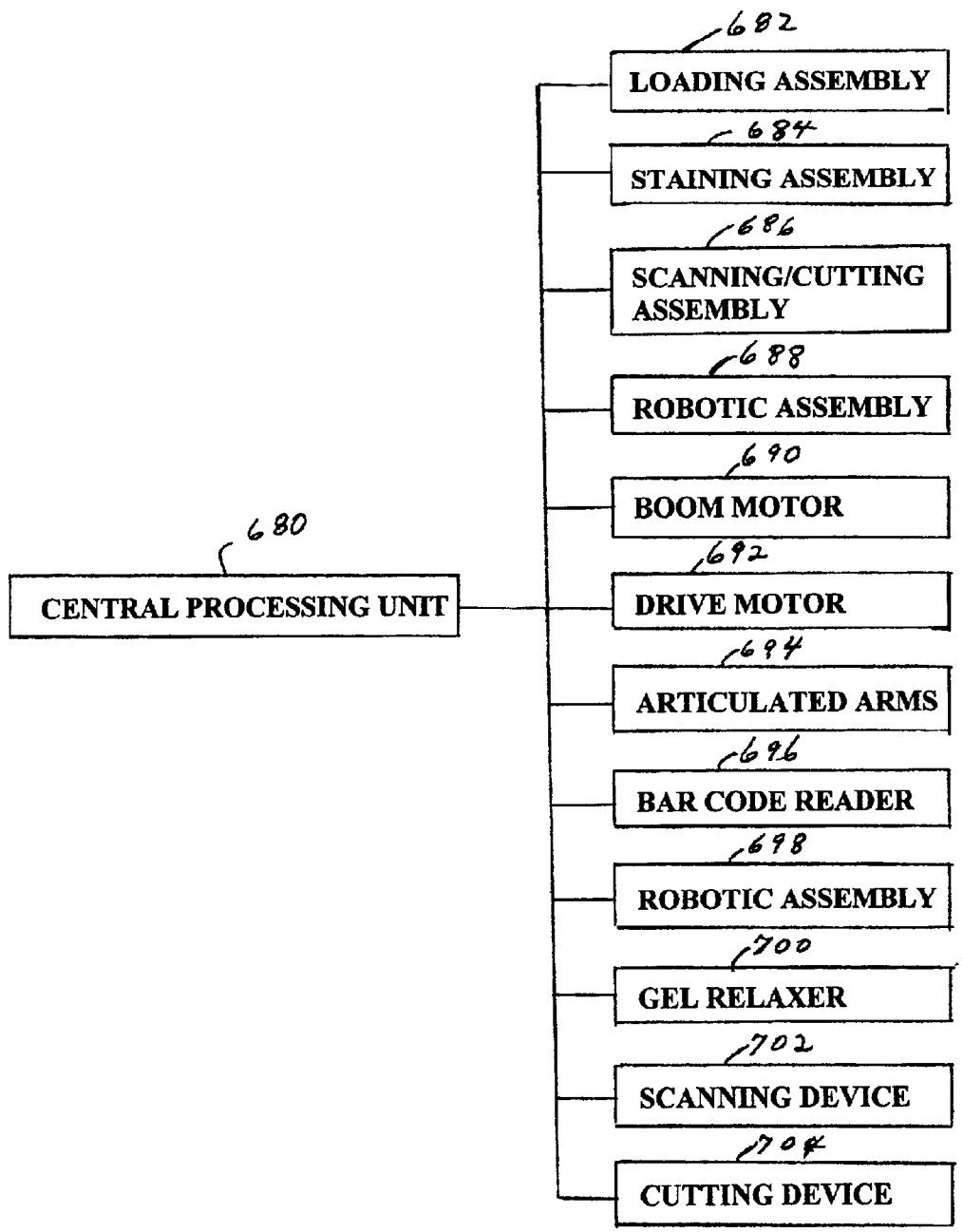
FIG. 66 is a schematic diagram showing the operation of the computer controlled assembly.

The automated apparatus of the invention is controlled and operated by a computer or central processing unit. FIG. 66 represents the control system for the apparatus, which includes a central processing unit indicated by block 680. The central processing unit 680 is operatively coupled to loading assembly 12 indicated by block 682, staining assembly 14 indicated by block 684, and scanning and cutting assembly indicated by block 686. The central processing unit 680 receives a signal from the control unit of loading assembly and stores a record of the identification bar code on the gel clamp and the gel. The central processing unit 680 includes or is connected to a database to identify a biological sample with the gel and gel clamp and selects the appropriate staining, scanning and cutting protocols for the sample. The central processing unit is operatively connected to drive motor 160 for controlling the movement of the robotic assembly along frame 144 indicated by block 688, motor 170 for raising and lowering boom 156 indicated by block 690, motor 184 for moving the articulated arm along the length of boom 156 indicated by block 692 and the actuator device 200 for operating the articulated arms 196 indicated by block 694. The central processing unit is also operatively connected to bar code reader 215 on robotic assembly 176 indicated by block 196 to identify a gel and gel clamp.

The computer controlled operating system of the invention coordinates the various processing steps for treating a plurality of electrophoresis gels. In preferred embodiments of the invention, the computer operating system continuously manipulates a plurality of gels through the apparatus and maintains a record of the location and progress of each gel as it passes through the respective stages. The operation and movement of robotic assembly for capturing a gel from a storage tank, transferring the gel to the various treatment tanks and length of time gels remain in the various tanks are controlled and recorded by a main computer. The computer is also able to record the identification bar code for a selected gel and monitor the location of the gel throughout the processing steps. The computer system also controls the operation of robotic assembly 456 indicated by block 698; gel relaxing assembly 710 indicated by block 700, scanning device 452 indicated by block 702; and cutting device 454 indicated by block 704.

While various embodiments of the invention have been chosen to illustrate the invention, it will be understood by those skilled in the art that additions and modifications can be made without departing from the scope of the invention as defined in the appended claims.

What is claimed is:

1. An automated apparatus for treating an electrophoresis gel slab, said apparatus comprising:

a plurality of liquid treating tanks having a dimension to receive an electrophoresis gel slab;

a first robotic assembly for transporting electrophoresis gel slabs between said liquid treating tanks;

a second robotic assembly for manipulating a support tray having a dimension to support said electrophoresis gel slab and for transporting said support tray and electrophoresis gel slabs between gel processing devices; and a computer operatively connected to said first robotic assembly and said second robotic assembly to coordinate movement of said first robotic assembly with respect to said liquid treating tanks and to coordinate movement of said second robotic assembly with respect to said gel processing devices.

2. The apparatus of claim 1, wherein said computer is programmed to transfer said gel slab between said first robotic assembly and said second robotic assembly.

3. The apparatus of claim 2, wherein said first robotic assembly is movable toward said second robotic assembly to transfer said gel slab from said first robotic assembly onto said support tray.

4. The apparatus of claim 1, wherein said first robotic assembly includes a reader for reading identifying information associated with said gel slab.

5. The apparatus of claim 4, wherein said computer is programmed to move said gel slab between at least two of said liquid treating tanks based on a predetermined protocol for said gel slab.

6. The apparatus of claim 4, wherein said reader is operatively connected to said computer and wherein said computer monitors the location of said gel slab within said apparatus.

7. The apparatus of claim 6, wherein said apparatus receives a plurality of said gel slabs simultaneously and wherein said computer controls said first robotic assembly to transfer each of said gel slabs between said liquid treating tanks according to a predetermined processing protocol and to monitor the location of said gel slabs within said apparatus.

8. The apparatus of claim 1, wherein said each of said liquid treating tanks can receive a gel slab simultaneously and wherein said computer controls said first robotic assembly to move each of said gel slabs between processing stations based on a predetermined protocol.

9. The apparatus of claim 8, further comprising a storage tank dimensioned to receive a plurality of gel slabs, and wherein said computer is programmed to operate said first robotic assembly and transfer a selected gel slab between said liquid treating tanks according to a predetermined processing protocol.

10. The apparatus of claim 1, wherein said gel slab is coupled to a clamp assembly, said clamp assembly comprises opposing clamping jaws having a dimension to grip an edge of said gel slab and to vertically suspend said gel slab.

11. The apparatus of claim 10, wherein said first robotic assembly includes a coupling arm for removably coupling to said clamping assembly and transporting said gel slab between said liquid treating tanks.

12. The apparatus of claim 1, wherein said first robotic assembly includes a robotic arm for removably coupling to an electrophoresis gel and being movable in a vertical direction and in a horizontal direction, and wherein said second robotic assembly includes a movable arm that is movable in a vertical direction and in a horizontal direction.

13. The apparatus of claim 12, wherein said second robotic assembly includes an arm having a coupling assembly for removably coupling with said support tray.

14. The apparatus of claim 13, wherein said coupling assembly includes a movable coupling member for coupling with said support tray and an actuator, said actuator being operatively connected to said computer.

15. The apparatus of claim 14, said coupling assembly further comprising a base and a ledge portion coupled to said base, said coupling member being movable to clamp said support tray between said coupling member and said base and ledge portion.

16. The apparatus of claim 15, wherein said coupling member extends outwardly from said base and is movable in a direction toward and away from said ledge portion.

17. The apparatus of claim 16, wherein said support tray includes an aperture dimensioned to receive said coupling member for removably coupling said support tray to said coupling assembly.

18. The apparatus of claim 17, wherein said coupling member includes a body having a dimension to cooperate with said aperture in said support tray, and an enlarged head coupled to a distal end of said body.

19. The apparatus of claim 14, wherein said actuator is pneumatically operated.

20. The apparatus of claim 12, wherein said second robotic assembly is movable to a first position for cooperating with said first robotic assembly, and wherein said first robotic assembly is movable toward said second robotic assembly to transfer said gel slab onto said support tray.

21. The apparatus of claim 20, wherein said movable arm of said second robotic assembly is pivotable about a horizontal axis for moving said support tray between a substantially vertical orientation and a substantially horizontal orientation.

22. The apparatus of claim 20, wherein said movable arm of said second robotic assembly is pivotal to an inclined position, and wherein said first robotic assembly is movable in a horizontal direction to transfer said gel slab from said first robotic assembly to said support tray.

23. The apparatus of claim 20, wherein said movable arm of said second robotic assembly is pivotable between said inclined position and a horizontal position, said movable arm being movable in a substantially horizontal plane.

24. The apparatus of claim 20, wherein said support tray comprises a substantially flat support surface for receiving said gel slab.

25. The apparatus of claim 24, further comprising a gel clamp having opposing clamping jaws for clamping an edge of said gel slab and suspending said gel slab, and wherein said gel clamp is supported by said support tray with said gel slab.

26. The apparatus of claim 25, further comprising a gel clamp actuating member for opening s aid jaws of said gel clamp while supported on said support tray for a time sufficient to enable said gel slab to lay substantially flat on said support tray.

27. The apparatus of claim 25, wherein said movable arm of said second robotic assembly is movable in a vertical direction, and wherein said gel clamp actuating member is a stop member positioned above said gel clamp, and said movable arm moves said support tray to contact said gel clamp with said stop member to open said gel clamp.

28. The apparatus of claim 26, wherein said second robotic assembly is movable to a position so that said gel clamp actuating member engages said gel clamp to open said gel clamp.

29. The apparatus of claim 1, further comprising a scanning device for optically scanning said get slab on said tray.

30. The apparatus of claim 29, wherein said second robotic apparatus is movable between a first position for positioning said support tray for receiving said gel slab from said first robotic assembly and a second position for operatively positioning said support tray in said scanning device.

31. The apparatus of claim 30, wherein said second position is substantially horizontal and said second robotic assembly is movable in a substantially horizontal plane to said second position.

32. The apparatus of claim 30, said apparatus further comprising a cutting device for cutting selected portions of said gel slab, wherein said second robotic assembly is movable to a third position for operatively positioning said support tray in said cutting device.

33. The apparatus of claim 32, wherein said second robotic assembly comprises a movable arm that is movable in a substantially horizontal direction to said third position.

34. The apparatus of claim 33, wherein said movable arm is pivotable from said first position to said second position.

35. The apparatus of claim 34, wherein said first position orients said support tray at an incline, and wherein said second position orients said support tray in a substantially horizontal position.

* * * * *

UNITED STATES PATENT AND TRADEMARK OFFICE
CERTIFICATE OF CORRECTION

PATENT NO. : 6,932,895 B2
DATED : August 23, 2005
INVENTOR(S) : Anderson et al.

It is certified that error appears in the above-identified patent and that said Letters Patent is hereby corrected as shown below:

Column 1,
Line 27, insert -- This invention was made with Untied States Government support under cooperative agreement number 70NANB5H1075 awarded by the National Institute of Standards and Technology. The government has certain rights in the invention. --.

Column 8,
Line 20, delete "relazer" and insert -- relaxer --.
Line 24, delete "relaxwer" and insert -- relaxer --.

Signed and Sealed this

Twenty-fifth Day of October, 2005

JON W. DUDAS
*Director of the United States Patent and Trademark Office*